US011505586B2

(12) United States Patent
Söllner et al.

(10) Patent No.: US 11,505,586 B2
(45) Date of Patent: Nov. 22, 2022

(54) INTERACTION OF DRAXIN AND γ-NETRINS

(71) Applicant: Max-Planck-Gesellschaft zur Foerderung der Wissenschaften e.V., Munich (DE)

(72) Inventors: Christian Söllner, Nürtingen (DE); Xuefan Gao, Tübingen (DE); Christiane Nüsslein-Volhard, Tübingen-Bebenhausen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 245 days.

(21) Appl. No.: 16/553,536

(22) Filed: Aug. 28, 2019

(65) Prior Publication Data

US 2020/0040047 A1 Feb. 6, 2020

Related U.S. Application Data

(62) Division of application No. 15/113,878, filed as application No. PCT/EP2015/051088 on Jan. 21, 2015, now Pat. No. 10,435,442.

(60) Provisional application No. 62/049,643, filed on Sep. 12, 2014.

(30) Foreign Application Priority Data

Jan. 23, 2014 (EP) .................................... 14152341

(51) Int. Cl.

| | |
|---|---|
| ***C07K 14/47*** | (2006.01) |
| ***C07K 14/475*** | (2006.01) |
| ***C07K 14/46*** | (2006.01) |
| ***C07K 16/18*** | (2006.01) |
| *A61K 38/00* | (2006.01) |

(52) U.S. Cl.

CPC ........ *C07K 14/4703* (2013.01); *C07K 14/461* (2013.01); *C07K 14/47* (2013.01); *C07K 14/475* (2013.01); *C07K 16/18* (2013.01); *A61K 38/00* (2013.01); *C07K 2317/76* (2013.01); *C07K 2319/30* (2013.01)

(58) Field of Classification Search

None

See application file for complete search history.

(56) References Cited

FOREIGN PATENT DOCUMENTS

| | | |
|---|---|---|
| JP | 2007186443 A | 7/2007 |
| WO | 2004035732 A2 | 4/2004 |
| WO | 2004035732 A3 | 4/2004 |

OTHER PUBLICATIONS

UniProtKB-O42140; https://www.uniprot.org/uniprot/042140; accessed Sep. 16, 2021.*

UniProtKB-O95631; https://www.uniprot.org/uniprot/095631; accessed Sep. 16, 2021.*

Guo (Proc Natl Acad Sci USA. Jun. 22, 2004;101(25):9205-10. Epub Jun. 14, 2004).*

Lauderdale et al. (1997, Mol. Cell. Neurosci. 9:293-313).*

Keino-Masu et al. (1996, Cell 87:175-185).*

UniProtKB-Q90922; https://www.uniprot.org/uniprot/Q90922; accessed Sep. 16, 2021.*

Krueger et al (2013, ChemBioChem 14:788-799).*

Méneret et al. (2017, J Clin Invest 127(11):3923-3936).*

Vosberg et al. (2020, Mol Psychiat 25:297-307).*

Ahmed et al., "Draxin Inhibits Axonal Outgrowth through the Netrin Receptor DCC", The Journal of Neuroscience, Sep. 28, 2011, 31 (39), pp. 14018-14023.

Fitamant et al., "Netrin-1 expression confers a selective advantage for tumor cell survival in metastatic breast cancer", PNAS, Mar. 25, 2008, vol. 105, No. 12, pp. 4850-4855.

Kim et al., "Genome sequencing reveals insights into physiology and longevity of the naked mole rat", NATURE, vol. 479, No. 7372, Oct. 12, 2011, pp. 223-227.

Leong et al., "Salmo salar and Esox lucius full-length cDNA sequences reveal changes in evolutionary pressures on a post-tetraploidization genome", BMC Genomics, vol. 11, No. 1, Apr. 30, 2010, p. 279.

Paradisi et al., "Combining chemotherapeutic agents and netrin-1 interference potentiates cancer cell death", EMBO Molecular Medicine, vol. 5 No. 12, Dec. 8, 2013, pp. 1821-1834.

Paradis et al., "Netrin-1 up-regulation in inflammatory bowel diseases is required for colorectal cancer progression", Proceedings of the National Academy of Sciences, vol. 106, No. 40, Oct. 6, 2009, p. 17146-17151.

XP002725360, Human secreted protein SEQ ID #1263., retrieved from EBI accession No. GSP:ADP29265 Database accession No. ADP29265 Aug. 12, 2004.

XP002725361, SubName: Full=Draxin, retrieved from EBI accession No. UNIPROT:G5C510 Database accession No. G5C510, Dec. 14, 2011.

XP002725362, SubName: Full=Clorf187, retrieved from EBI accession No. UNIPROT:COH8J0 Database accession No. COH8J0, May 5, 2009.

Partial European Search Report cited in EP 14 15 2341 dated Jun. 16, 2014, 4 pgs.

(Continued)

*Primary Examiner* — Elizabeth C. Kemmerer

(74) *Attorney, Agent, or Firm* — Rothwell, Figg, Ernst & Manbeck, P.C.

(57) ABSTRACT

This invention relates to extracellular protein-protein interactions and their possible therapeutic uses. More particularly, this invention describes the interaction between Draxin, particularly fragments binding to γ-Netrins comprising SEQ ID NO.:1, 2 or 3, and variants thereof, with γ-Netrins, and the use of this interaction to disrupt γ-Netrin/Netrin receptor interactions. The invention also relates to diagnostic and/or therapeutic uses of Draxin or fragments or variants thereof, as well as to an antibody against Draxin inhibiting binding of Draxin to γ-Netrins. Further, the invention relates to fragments of γ-Netrins, in particular Draxin-binding Netrin1-fragments comprising SEQ ID NO.: 51 and variants thereof, as well as to an antibody against γ-Netrins inhibiting binding of γ-Netrins to Netrin receptors.

8 Claims, 15 Drawing Sheets

Specification includes a Sequence Listing.

(56) References Cited

OTHER PUBLICATIONS

Joseph et al., "The neuroimmune guidance cue netrin-1: a new therapeutic target in cardiovascular disease", Am J Cardiovasc Dis, 2013; 3(3):129-134.
Low et al., "Netrin-1 is a Novel Myelin-Associated Inhibitor to Axon Growth", The Journal of Neuroscience, Jan. 30, 2008, 28(5): 1099-1108.
van Gils et al., "The neuroimmune guidance cue netrin-1 promotes atherosclerosis by inhibiting macrophage emigration from plaques", NAT IMMUNOL.; 13(2): 136-143, 2012.
Delloye-Bourgeois et al., 2009, J. Natl. Cancer Inst. 10:237-247.
Lawrence et al. (1999, Anti-Cancer Drugs 10:655-661).
Hanauske et al. (1995, Investigational New Drugs 13: 43-49).
Kornblith et al. (2003, Anticancer Research 23:543-548).
Depenbrock et al. (1997, European Journal of Cancer 33:2404-2410).
Gabrielson et al. (1999, Clinical Cancer Research 5: 1638-1641).
Georgoulias (2002, Current Medicinal Chemistry 9:869-877).
Burris III et al. (1992, Journal of the National Cancer Institute 84: 1816-1820).
Martin et al. (1994, Journal of the National Cancer Institute 86:608-613).
Izbicka et al. (1999, investigational New Drugs 16:221-225).
Flanagan et al. Alkaline phosphatase fusions of ligands or receptors as in situ probes for staining of cells, tissues, and embryos. Methods Enzymol. 2000;327:19-35.
GenBank Accession AK075558 [online], National Center for Biotechnology Information, Bethesda MD, 20894 USA. [retrieved Aug. 31, 2017]. Retrieved from the internet:<URL: https://www.ncbi.nlm.nih.gov/nuccore/AK075558>.
Guo et al. Protein tolerance to random amino acid change. Proc Natl Acad Sci U SA. Jun. 22, 2004;101(25):9205-10. Epub Jun. 14, 2004.
Haspel et al. System for cleavable Fc fusion proteins using tobacco etch virus (TEV) protease. Biotechniques. Jan. 2001;30(1 ):60, 61 and 64-66.
Islam et al. Draxin, a repulsive guidance protein for spinal cord and forebrain commissures. Science. Jan. 16, 2009;323(5912):388-93, and Supporting Online Material, pp. 1-19.
Ko et al. Netrin-1 as a potential target for metastatic cancer: focus on colorectal cancer. Cancer Metastasis Rev. Mar. 2014;33(1):101-13.

* cited by examiner

Figure 1
A
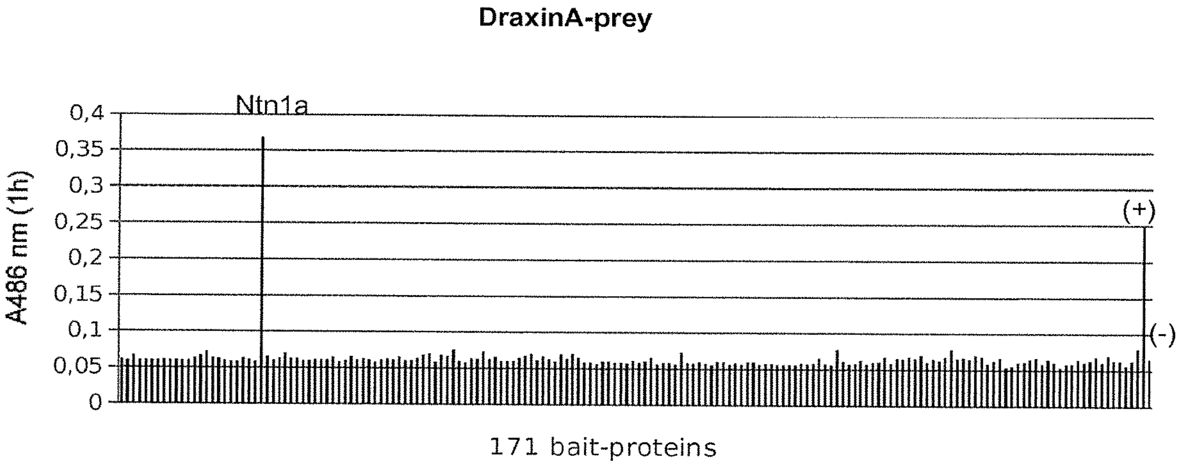
B
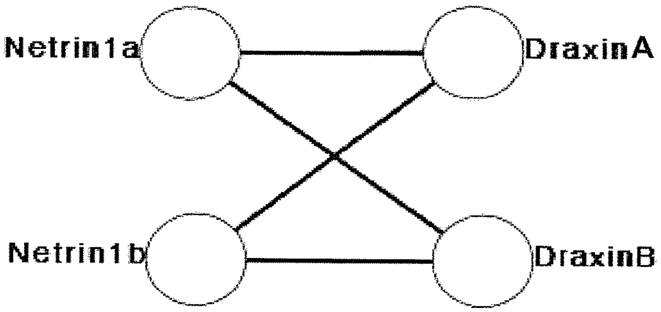

A

| prey \ bait | hNETRIN1 | zNetrin1a | hDRAXIN | zDraxinA | zDraxinB |
|---|---|---|---|---|---|
| hNETRIN1 | 0.068<br>0.061 | 0.071<br>0.067 | 0.289<br>0.276 | 0.272<br>0.227 | 0.131<br>0.174 |
| zNetrin1a | 0.064<br>0.059 | 0.064<br>0.063 | 0.136<br>0.249 | 0.323<br>0.276 | 0.235<br>0.174 |
| human DRAXIN | 0.217<br>0.197 | 0.204<br>0.204 | 0.054<br>0.057 | 0.06<br>0.06 | 0.056<br>0.058 |
| zebrafish DraxinA | 0.369<br>0.373 | 0.349<br>0.395 | 0.056<br>0.06 | 0.062<br>0.06 | 0.057<br>0.059 |
| zebrafish DraxinB | 0.096<br>0.086 | 0.103<br>0.084 | 0.06<br>0.057 | 0.061<br>0.056 | 0.057<br>0.059 |

Binding
Weak binding
No binding

```
Homo sapiens (SEQ ID NO:4)             1 MAGPAIHTAPMLFLVLLLPLELSLAGALAPGTPARNLPENHIDLPGPALWTPQASHHRRR
Mus musculus (SEQ ID NO:52)            1 MAGCPVLRVPTLFLILLLFPELHTAGTLASGSSARNLPETHSHLPSSALWVSQASHHGRR
Gallus gallus (SEQ ID NO:53)           1 MAASSTPFSPSLFLCVLVLIDITLAVSLDTDMKLKSENNNHLQNQETWPQQPRSGHHHKH
Danio rerio DraxinA (SEQ ID NO:5)      1 MVAPG--LCQLFILLLITLSHTSHSSEISSDNFKQSLTTSTTTSKEHPETGLTGGRQQKR
Danio rerio DraxinB (SEQ ID NO:6)      1 -MAVSCWYFALFLIFDLMTMTLGTNTHHNSPMEVFSENIIIPPKPEASTHHHTHQRTDRG

                                      61 GPGKKEWGPG--LPSQAQDGAVVTATRQASRLPEAEGLLP-EQSPAGLLQDKD--LLLGL
                                      61 GLGKKDRGPG--RPSRAQEGAVVTATKQASQMTLGQ-------PPAGLLQNKE--LLLGL
                                      61 GLAKKGRVLA--LPVRGQP-AGEEALRVGSGAPAMEELVP-LGQPAALKQDKDKDVFLGF
                                      59 HWSGKERDSAGLFSQRHMDRLEDDGTSMEGLSPVRLEMGPGDTMKAEVHGEVRASAQMRQ
                                      60 RKERMTASQLRERPRIAIFHTQNEGPDLEGLSPVRLEMEP---ADKRRVMTPRKKTPMGS

                                     116 ALPYPEKENRPPGWERTRKRSREHKR--RRDRLRLHQGRALVRGPS----SLMKKAELSE
                                     110 TLPYPEKEARSPAWERVKKRGREHKR--RRDRLRLHRGRAAIRGPS----SLMKKVEPSE
                                     117 ELPHAERENQSPGSERGKKQNREQRRHSRRDRLKHHRGKTAV-GPS----SLYKKPE-SF
                                     119 GSHPAEGELNRKGRRHSHRLLAEHRK--HGGKKDKGRGKGDLSDPEPELDSLLKDLNAFE
                                     117 DSLIQEKMNISPGAETPEKAMRRPTV---RKVFGGHITRAPHEEES--LASGKKRRVSFD

                                     170 AQVLDAAMEESSTSLAPTMFPLTTFE-AAPATEESLILPVTSLRPQ-QAQPRSDGEVMPT
                                     164 DRMLEGTMEESSTSLAPTMFPLTMTDGATPTTEESRILPVTSLRP--QTQPRSDGEVMPT
                                     171 EQQFQNLQAEEATSPTPTVLPFTALD-LVVSTEEPPVLPATSPRS--QARLRQDGDVMPT
                                     177 DGLHTSPPHYNSVPLNEVPSPLSPILVTTAIKGHPPTLPPASTKPQKSSQGRTQGEVMPT
                                     172 QRLNKASFGSPTEPVLPAATVGTPILPITAAVDGH---PNPSSEP--QVRRYLGGDVAPT

                                     228 LDMALFDWTDYEDLKP-DGWPSAKKK--EKHRGKLSSDGNETSPA-EGEPCDHHQDCLPG
                                     222 LDMALFDWTDYEDLKP-EVWPSAKKK--EKHWSHFTSDGNETSPA-EGDPCDHHQDCLPG
                                     228 LDMALFDWTDYEDLKP-EMWPSAKKK--EKRRSKSSNGGNETSSA-EGEPCDHHLDCLPG
                                     237 LDMTLFDWTDYEDMKPADSWPSNKRK--DKRRSKNKSNGNTTTEAGIVEPCDHHLDCLSG
                                     227 FNMALFDWTDYEDMRPGDKKQYSKKQGSEKQATQSPSTGLVRLTS-ENNVCKHHLDCLPG

                                     284 TCCDLREHLCTPHNRGLNNKCFDDCMCVEGLRCYAKFHRNRRVTRRKGRCVEPETANGDQ
                                     278 TCCDLREHLCTPHNRGLNNKCFDDCMCMEGLRCYAKFHRNRRVTRRKGRCVEPETANGDQ
                                     284 SCCDLREHLCKPHNRGLNNKCVDDCMCTEGLRCYAKFHRNRRVTRRKGRCVEPESANGEQ
                                     295 SCCDLREPHCKPHNRGLNNKCFDDCMCEEGLRCYAKFHRKRRVTRRRGRCVDPESVNSNQ
                                     286 SCCNLRKHVCELMNRGFNNKCYDSCMCEEGLRCYAKSHRHYRITRKKGQCVDPEDLNHAV

                                     344 GSFINV
                                     338 GSFINI
                                     344 GSFINV
                                     355 GAFITV
                                     346 SRWMQM
```

Figure 4
A
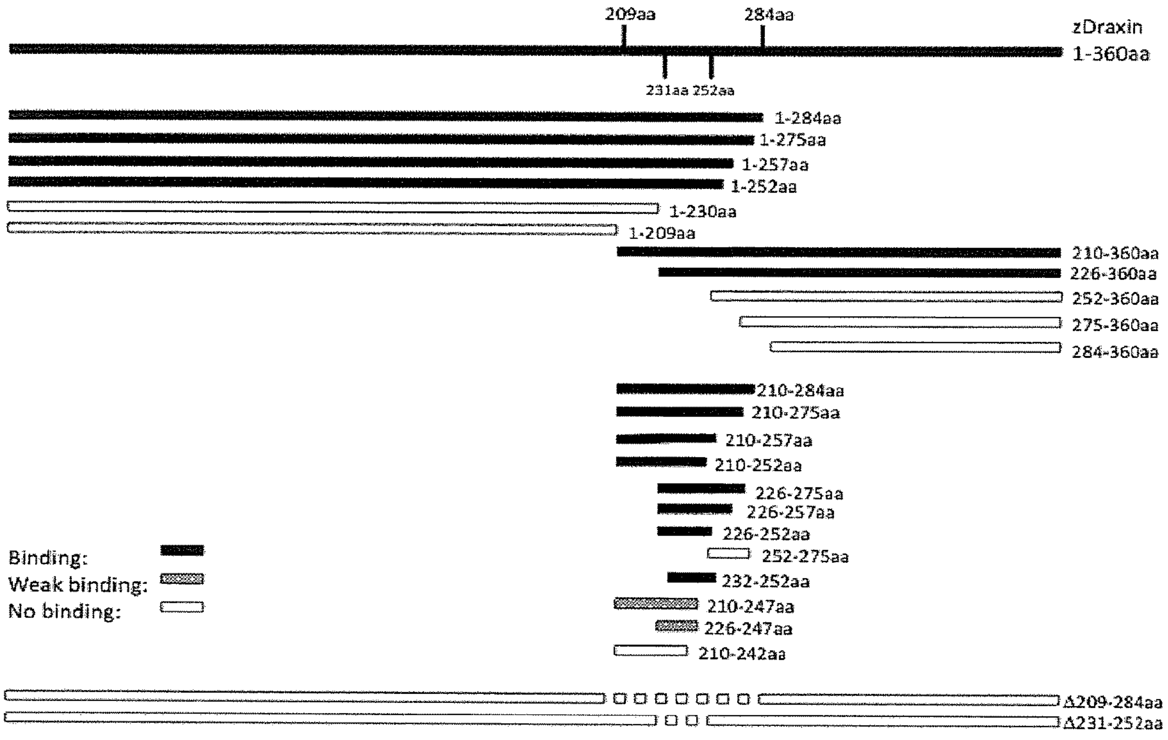
B
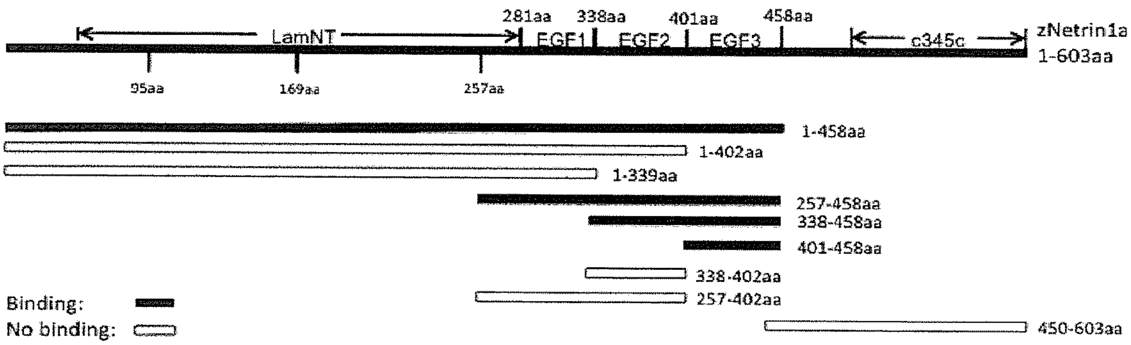

Figure 4 continued c

Figure 5

| | | |
|---|---|---|
| Felis catus (SEQ ID NO:54) | EVMPTLDMALFDWTDYEDLKP | |
| Rattus norvegicus (SEQ ID NO:55) | EVMPTLDMALFDWTDYEDLKP | |
| Mus musculus (SEQ ID NO:56) | EVMPTLDMALFDWTDYEDLKP | |
| Homo sapiens (SEQ ID NO:1) | EVMPTLDMALFDWTDYEDLKP | |
| Equus caballus (SEQ ID NO:57) | EVMPTLDMALFDWTDYEDLKP | |
| Bos Taurus (SEQ ID NO:58) | EVMPTLDMALFDWTDYEDLKP | |
| Sus scrofa (SEQ ID NO:59) | EVMPTLDMALFDWTDYEDLKP | |
| Canis lupus (SEQ ID NO:60) | EVMPTLDMALFDWTDYEDLRP | |
| Gallus gallus (SEQ ID NO:61) | DVMPTLDMALFDWTDYEDLKP | |
| Danio rerio (SEQ ID NO:2) | DVAPTFNMALFDWTDYEDMRP | DraxinB |
| Danio rerio (SEQ ID NO:3) | EVMPTLDMTLFDWTDYEDMKP | DraxinA |
| Takifugu rubripes (SEQ ID NO:62) | EVMPTLDMTLFDWTDYEDMKP | |
| Xenopus tropicalis (SEQ ID NO:63) | DVMPTLDMTLFDWTDYEDMKP | |
| | :* **::*:*********::* | |

A
DraxinA aa232-252-prey
Ntn1a
(+)
141 bait-proteins
A486nm (2h)
0,45
0,4
0,35
0,3
0,25
0,2
0,15
0,1
0,05
0
B
DraxinA aa232-252-bait
Ntn1a
191 prey-proteins
A486nm (2h)
0,45
0,4
0,35
0,3
0,25
0,2
0,15
0,1
0,05
0

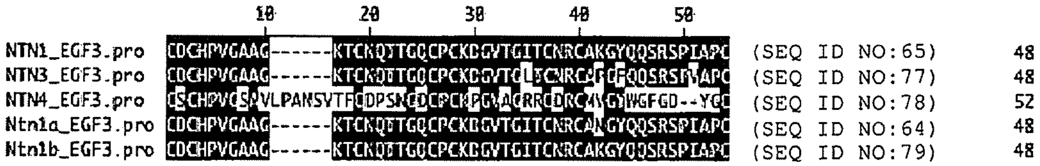

Figure 10

| | | |
|---|---|---|
| NTN1_EGF3.pro  CDCHPVGAAG------KTCKQTTGQCPCKDGVTGITCNRCAKGYQQSRSPIAPC | (SEQ ID NO:65) | 48 |
| NTN3_EGF3.pro  CDCHPVGAAG------KTCKQTTGQCPCKDGVTGLSCNRCGFQQSRSRVAPC | (SEQ ID NO:77) | 48 |
| NTN4_EGF3.pro  CSCHPVCSPVLPANSVTFDPSRCDCPCKPGVACRRCDRCVSGVWGFGD--YGC | (SEQ ID NO:78) | 52 |
| Ntn1a_EGF3.pro CDCHPVGAAG------KTCKQTTGQCPCKDGVTGITCNRCANGYQQSRSPIAPC | (SEQ ID NO:64) | 48 |
| Ntn1b_EGF3.pro CDCHPVGAAG------KTCKQTTGQCPCKDGVTGITCNRCAKGYQQSRSPIAPC | (SEQ ID NO:79) | 48 |

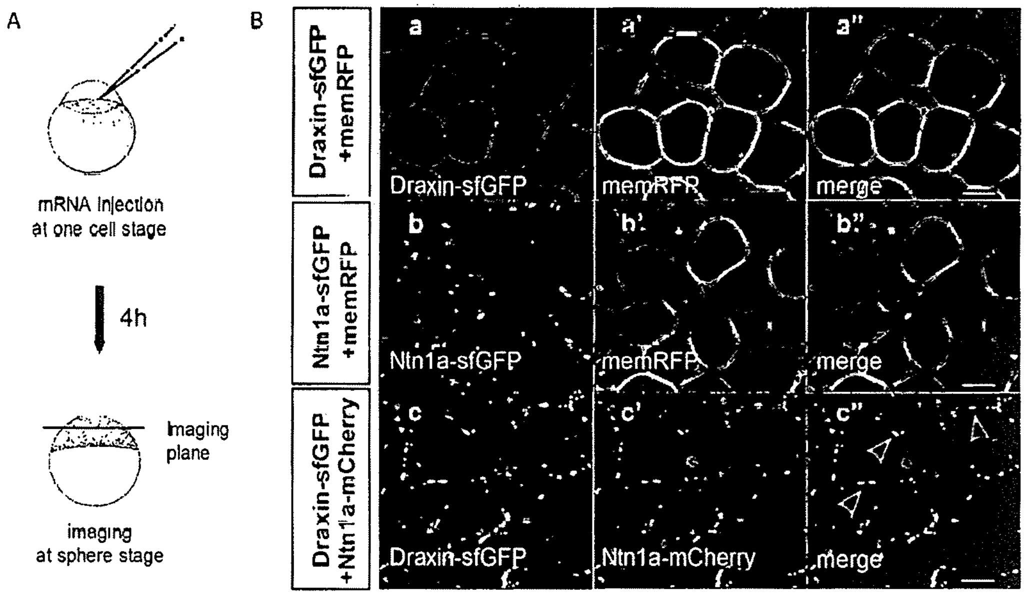

Bait (columns) / Prey (rows)

| Prey \ Bait | NTN1 | NTN3 | NTN4 | NTNG1 | NTNG2 | DRAXIN | DRAXIN 21aa | DCC | UNC5B | CM (-) | Matn4 (+) |
|---|---|---|---|---|---|---|---|---|---|---|---|
| NTN1 | 0.089 | 0.075 | 0.063 | 0.066 | 0.064 | 0.272 | 0.328 | 0.299 | 0.156 | 0.066 | 0.216 |
| NTN3 | 0.068 | 0.068 | 0.064 | 0.069 | 0.060 | 0.110 | 0.191 | 0.067 | 0.066 | 0.063 | 0.224 |
| NTN4 | 0.067 | 0.065 | 0.068 | 0.065 | 0.063 | 0.063 | 0.067 | 0.065 | 0.063 | 0.063 | 0.235 |
| NTNG1 | 0.062 | 0.064 | 0.066 | 0.062 | 0.061 | 0.061 | 0.063 | 0.063 | 0.061 | 0.061 | 0.254 |
| NTNG2 | 0.060 | 0.062 | 0.063 | 0.061 | 0.062 | 0.060 | 0.063 | 0.065 | 0.061 | 0.060 | 0.201 |
| DRAXIN | 0.361 | 0.290 | 0.076 | 0.077 | 0.072 | 0.062 | 0.063 | 0.072 | 0.078 | 0.072 | 0.213 |
| DRAXIN 21aa | 0.342 | 0.261 | 0.063 | 0.066 | 0.062 | 0.063 | 0.059 | 0.06 | 0.062 | 0.058 | 0.252 |
| DCC | 0.377 | 0.076 | 0.064 | 0.065 | 0.061 | 0.064 | 0.062 | 0.065 | 0.062 | 0.063 | 0.278 |
| UNC5B | 0.129 | 0.066 | 0.063 | 0.065 | 0.061 | 0.062 | 0.065 | 0.064 | 0.062 | 0.058 | 0.226 |
| CM (-) | 0.06 | 0.062 | 0.059 | 0.063 | 0.060 | 0.060 | 0.063 | 0.062 | 0.059 | 0.059 | 0.063 |

A486nm

| | |
|---|---|
| > 0.100 | Binding |
| 0.08-0.099 | Weak binding |
| 0.055-0.079 | No binding |

A

B

C

INTERACTION OF DRAXIN AND γ-NETRINS

CROSS REFERENCE TO RELATED APPLICATION

This application is a divisional of U.S. Ser. No. 15/113,878 filed Jul. 25, 2016, which is a 35 U.S.C. 371 National Phase Entry Application from PCT/EP2015/051088, filed Jan. 21, 2015, which claims the benefit of U.S. Patent Application No. 62/049,643 filed on Sep. 12, 2014 and European Patent Application No. 14152341.5 filed Jan. 23, 2014, the disclosure of which are incorporated by reference in their entirety.

FIELD OF THE INVENTION

This invention relates to extracellular protein-protein interactions and their possible therapeutic uses. More particularly, this invention describes the interaction between Draxin, particularly fragments binding to γ-Netrins comprising SEQ ID NO.:1, 2 or 3, and variants thereof, with γ-Netrins, and the use of this interaction to disrupt γ-Netrin/Netrin receptor interactions. The invention also relates to diagnostic and/or therapeutic uses of Draxin or fragments or variants thereof, as well as to an antibody against Draxin inhibiting binding of Draxin to γ-Netrins. Further, the invention relates to fragments of γ-Netrins, in particular Draxin-binding Netrin1-fragments comprising SEQ ID NO.: 51 and variants thereof, as well as to an antibody against γ-Netrins inhibiting binding of γ-Netrins to Netrin receptors.

SEQUENCE LISTING

The instant application contains a Sequence Listing which has been submitted in ASCII format via EFS-Web and is hereby incorporated by reference in its entirety. Said ASCII copy, created on Jan. 16, 2018, filed in the parent application Ser. No. 15/113,878 is named 57261 PUSWO_ST25.txt and is 87,752 bytes in size.

BACKGROUND OF THE INVENTION

The laminin-related netrin protein family in humans comprises 5 members. Three of them, Netrin1, Netrin3, and Netrin4 are secreted proteins. NetrinG1 and NetrinG2 instead are linked to the cell surface by a GPI anchor. The LamNT domain and the EGF domains of Netrin1 and Netrin3 are derived from the γ chain of Laminin1. In the context of the present invention, these Netrins are thus referred to as "γ-Netrins". In contrast, the corresponding domains of Netrin4, NetrinG1 and NetrinG2 are homologous to the domains present in the β chain of Laminin1 (Moore et al., 2007).

Netrin1 is a diffusible, laminin-related protein identified as neuronal guidance cue during development of the nervous system. Netrin1 mediates its biological effects through binding to receptors, which belong to the so-called dependence receptors, e.g. deleted in colorectal cancer (DCC) and uncoordinated-5-homolog (UNCSH). Recently, it has been found that Netrin1 is expressed outside the nervous system and contributes to the patterning of developing epithelial tissues such as mammary gland, pancreas, and lung by regulating diverse processes including adhesion, motility, proliferation, and differentiation of cells.

Numerous tumors have been described to express cell surface receptors belonging to the DCC- and UNC5-family. These receptors are binding to the secreted ligand Netrin1 in the extracellular space and serve, in addition to their well-established neurodevelopmental function, as dependence receptors in cancers (Castets et al., 2012; Mehlen et al., 2011). In tumors they can regulate tumor cell survival in a Netrin1 dependent manner. Netrin1 itself is known to be upregulated by many tumor types and has been suggested to act as an oncogene (Arakawa, 2004; Fitamant et al., 2008). If Netrin1 is not bound to dependence receptors of the DCC- and UNC5-family, the receptors cannot form dimers or multimers, which in turn triggers the activation of a pro-apoptotic pathway.

In several studies, decoy Netrin receptor fragments have been used to disrupt Netrin/Netrin receptor interactions in order to induce pro-apoptotic signaling. For example, such receptor fragments have been used in cancer cell lines (Delloye-Bourgeois et al., 2009; Fitamant et al., 2008) and in animal models (Fitamant et al., 2008; Paradisi et al., 2013; Paradisi et al., 2009) to induce cancer cell death. However, using a fragment of a Netrin receptor causes interference at a relatively late stage of the signaling cascade, namely just before dimerization of the receptor. Moreover, even when using high concentrations of these decoy receptors, a residual binding of Netrin to the full length receptor cannot be prevented.

It was thus an object of the invention to provide compounds that can be used for interfering with the binding of γ-Netrins, in particular Netrin1 to at least one of its receptors, which at least partially overcome the disadvantages of the prior art.

Draxin is a secreted protein described to be involved in axon guidance decisions (Islam et al., 2009). In contrast to Netrins 1-3, which are present in vertebrates and invertebrates, Draxin can only be found in vertebrate genomes. The amino acid sequence of human Draxin is shown as SEQ ID NO.: 4. In zebrafish, there exist two Draxin isoforms (DraxinA and DraxinB); their amino acid sequences are represented by SEQ ID NO.: 5 and SEQ ID NO.: 6.

By using an extracellular protein-protein interaction screen assay (AVEXIS), the present inventors identified Draxin as a novel direct binding partner for Netrin1. Furthermore, by using an AVEXIS based competition assay, the inventors were able to show that Draxin or Draxin protein fragments can compete with Netrin receptors for binding to Netrin1.

The present invention therefore provides specific peptides binding to γ-Netrins ("γ-Netrin-binding peptides"), particularly to Netrin1, as well as antibodies directed against γ-Netrins ("γ-Netrin-binding antibodies"), particularly against Netrin1, which may be used for interfering with γ-Netrin/Netrin receptor binding, in particular Netrin1/Netrin receptor binding. The invention further provides Draxin-binding peptides as well as Draxin-binding antibodies inhibiting binding of Draxin to γ-Netrins, in particular to Netrin1.

DETAILED DESCRIPTION OF THE INVENTION

In one aspect, the present invention relates to peptides which bind to at least one γ-Netrin, with a high specificity and a high affinity. Importantly, the affinity of Draxin to the γ-Netrins, in particular to Netrin1, is significantly higher than the affinity of γ-Netrins, in particular of Netrin1 to Netrin receptors.

Accordingly, the invention provides a γ-Netrin-binding peptide, comprising (i) the sequence EVMPTLDMALFDWTDYEDLKP (SEQ ID NO.: 1), or (ii) the sequence DVAPTFNMALFDWTDYEDMRP (SEQ ID NO.: 2), or (iii) the sequence EVMPTLDMTLFDWTDYEDMKP (SEQ ID NO.: 3), or (iv) a variant thereof having a sequence identity of at least 70%, at least 80%, at least 85%, at least 90%, or at least 95% to SEQ ID NO.: 1, 2 and/or 3, wherein said peptide has a length of up to 328 amino acids and is optionally fused to a heterologous peptide or polypeptide. Preferably, the γ-Netrin is Netrin1.

The γ-Netrin-binding peptide is characterized in that it binds with high affinity to Netrins derived from the γ chain of Laminin1, comprising in particular human Netrin1 and human Netrin3 as well as Netrins 1a, 1b and 2 from zebrafish (*Danio rerio*). In particular, the γ-Netrin-binding peptide of the invention binds to human Netrin1 and to zebrafish Netrin1a (also referred to as Ntn1a) and Netrin1b (also referred to as Ntn1b). In preferred embodiments, it is therefore referred to as "Netrin1-binding peptide".

In some embodiments, the peptide with a length of up to 328 amino acids comprises any one of SEQ ID NO.: 1, 2, 3 or a variant thereof having a sequence identity of at least 70%, at least 80%, at least 85%, at least 90%, or at least 95% to SEQ ID NO.: 1, 2 and/or 3 and is free of any further heterologous peptides.

In other embodiments, the peptide with a length of up to 328 amino acids comprises any one of SEQ ID NO.: 1, 2, 3 or a variant thereof having a sequence identity of at least 70%, at least 80%, at least 85%, at least 90%, or at least 95% to SEQ ID NO.: 1, 2 and/or 3 and is fused to a heterologous peptide or polypeptide as defined below.

The minimal sequence of the γ-Netrin-binding peptide, in particular Netrin1-binding peptide is represented by

```
                                SEQ ID NO.: 1
   EVMPTLDMALFDWTDYEDLKP,

                                SEQ ID NO.: 2
   DVAPTFNMALFDWTDYEDMRP,
   and

                                SEQ ID NO.: 3
   EVMPTLDMTLFDWTDYEDMKP, respectively.
```

In some embodiments, the peptide has a length of up to 328 amino acids, up to 324 amino acids, up to 320 amino acids, up to 250 amino acids, up to 200 amino acids, up to 100 amino acids, up to 50 amino acids, or up to 30 amino acids. According to other embodiments, the peptide has a length of up to 150 amino acids or up to 125 amino acids. Fragments comprising up to 50 amino acids are preferred according to some embodiments.

In certain preferred embodiments, a variant of SEQ ID NO.: 1, SEQ ID NO.: 2 or SEQ ID NO.: 3 have a sequence identity of at least 70% to SEQ ID NO.: 1, 2 and/or 3. In further embodiments the level of sequence identity may be at least 90%, or even at least 95% to SEQ ID NO.: 1, 2 and/or 3.

A "variant" in the context of the present invention is any peptide whose amino acid sequence varies in at least one position from the respective reference peptide, but retains the biological activity of the reference peptide; for example, a variant of SEQ ID NO.: 1 differs in at least one amino acid therefrom, and retains the γ-Netrin-, particularly Netrin1-binding activity. In particular, variants of SEQ ID NO.: 1, 2 and 3 differ in 1, 2, 3, 4, 5, 6 or 7 amino acids from SEQ ID NO.: 1, SEQ ID NO.: 2 and/or SEQ ID NO.: 3, provided they retain the γ-Netrin-, particularly Netrin1-binding activity. Variations will usually be generated by amino acid substitutions. Particularly, a variant according to the invention will be characterized in that it has been changed to contain at least one non-naturally occurring substitution modification relative to the respective reference peptide.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. Any amino acid of the sequences disclosed herein may be replaced either by an unmodified canonical proteinogenic L-amino acid, or by an unmodified canonical proteinogenic D-amino acid. Also envisaged are substitutions with non-canonical proteinogenic amino acids, in particular with ornithine, 2,4-diamino butyric acid, 2,3-diamino propionic acid, selenocysteine, pyrrolysine, hydroxyproline, O-phosphoserine, O-phosphotyrosin, γ-carboxyglutamic acid, γ-aminobutyric acid, norleucine, ε-aminohexanoic acid, and with other posttranslationally modified amino acids, e.g. amino acids with amidated carboxyl groups (at C-termini of peptides), amino acids with alkylated (e.g. methylated) side chains, amino acids with an amino side chain group (such as lysine and ornithine) with modifications at one or both of the hydrogen atoms of the amino side chain group, for example with a lipophilic moiety attached via a carboxamide bond, etc.

The percent sequence identity may be determined according to the following formula:

$$I=n:L$$

wherein I is the identity in percent, n is the number of identical amino acids between a given sequence and a comparative sequence as shown e.g. in SEQ ID NOs.: 1, 2 and 3, and L is the length of the comparative sequence. Importantly, when calculating the percent sequence identity according to this formula, an alignment of the two sequences shall be carried out without gaps between complementary portions and over the whole length of the comparative sequence.

In specific embodiments, the invention provides a γ-Netrin-binding peptide, comprising (i) the sequence EVMPTLDMALFDWTDYEDLKP (SEQ ID NO.: 1), or (ii) the sequence DVAPTFNMALFDWTDYEDMRP (SEQ ID NO.: 2), or (iii) the sequence EVMPTLDMTLFDWTDYEDMKP (SEQ ID NO.: 3), or (iv) a variant thereof having a sequence identity of at least 70%, at least 80%, at least 85%, at least 90%, or at least 95% to SEQ ID NO.: 1, 2 and/or 3, wherein said peptide has a length of up to 100 amino acids and is optionally fused to a heterologous peptide or polypeptide.

According to some embodiments, the γ-Netrin-binding peptide, in particular the Netrin1-binding peptide, comprises any one of SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14 or SEQ ID NO.: 15 or a corresponding fragment of another species. Preferably, the peptide comprises any one of SEQ ID NO.: 10, SEQ ID NO.: 11, SEQ ID NO.: 12, SEQ ID NO.: 13, SEQ ID NO.: 14, and SEQ ID NO.: 15 or a corresponding fragment of another species, more preferably SEQ ID NO.: 15 or a corresponding fragment of another species.

In some preferred embodiments, the γ-Netrin-binding peptide, in particular the Netrin1-binding peptide, comprises a sequence which has a length of 22 amino acids. This 22-amino-acid (22aa) sequence may for example be SEQ ID NO.:16, or it may be SEQ ID NO.: 14, or it may be SEQ ID NO.: 17, or it may be a variant of any of these sequences, e.g.

a corresponding fragment from another species with an additional amino acid residue, preferably glycine (Gly) at the N-terminus. Variants of SEQ ID NO.: 16, 14, 17 have a sequence identity of at least 70% to SEQ ID NO.: 16, 14 and/or 17. In further embodiments, the level of sequence identity may be at least 90%, or even at least 95% to SEQ ID NO.: 16, 14 and/or 17. In particular, a variant of SEQ ID NO.: 16, 14, 17 may differ in 1, 2, 3, 4, 5, 6 or 7 amino acids from SEQ ID NO.: 16, SEQ ID NO.: 14 and/or SEQ ID NO.: 17, provided they retain the γ-Netrin-binding activity.

Also encompassed by the invention is any variant of any one of SEQ ID NOs.: 7-15 or a corresponding fragment of another species having a sequence identity of at least 50%, at least 60%, at least 70%, at least 80%, at least 85%, at least 90%, or at least 95% thereto, as long as the binding activity to γ-Netrins, preferably to Netrin1, is maintained. In some preferred embodiments, the level of sequence identity is at least 70%. In further preferred embodiments, the level of sequence identity is at least 90%.

In some embodiments, the γ-Netrin-binding peptide, in particular the Netrin1-binding peptide, according to the invention is fused to a heterologous peptide or polypeptide. A "heterologous peptide or polypeptide" in the context of the invention is any peptide with a length of at least 4 amino acids, which originates from another species as compared to the γ-Netrin-binding peptide or which is an artificial, i.e. non-naturally occurring peptide or polypeptide. Examples of such heterologous (poly)peptides are protein tags, in particular epitope tags such as the Myc-tag and the HA-tag, affinity tags such as FLAG, poly(His), chitin binding protein (CBP), maltose binding protein (MBP) and glutathione-S-transferase (GST), enzymes such as alkaline phosphatase, luciferase, horseradish peroxidase and β-galactosidase, or fluorescent proteins such as GFP, RFP and the like. Other examples are sequences that direct peptides attached thereto to specific locations inside cells or to the extracellular space (signal sequences); specific examples of such sequences are represented by SEQ ID NOs.: 70 and 71.

Further preferred examples of heterologous (poly)peptides are immunoglobulins (Ig) or functional fragments of immunoglobulins, such as Fv, scFv, Fab, Fab', F(ab')2, Fc, diabodies, minibodies, domain antibodies (dAb), camelid antibodies, nanobodies (VHH), disulfide stabilized Fv fragments (dsFv) and CDR-comprising peptides. The immunoglobulins or fragments thereof may be of any isotype, e.g. of the IgA-, IgD-, IgE, IgG or IgM-type. A functional structure analogous to the isotype G of immunoglobulins (IgG) is preferred. Among these, immunoglobulins or fragments thereof of the IgG1-, IgG2-, IgG3-, or IgG4-type are preferred.

In particularly preferred embodiments, the heterologous peptide or polypeptide is an Ig Fc fragment, for example an Fc fragment from mouse, rat, chicken, rabbit or human, with human Ig Fc fragments being preferred. Still more preferably, the human Ig Fc fragment is a human IgG Fc fragment, e.g. a human IgG1, IgG2, IgG3, or IgG4 Fc fragment.

The heterologous (poly)peptide may be conjugated to the γ-Netrin-binding peptide directly or via a spacer of suitable length. Suitable spacers are e.g. heterologous peptide linkers having a length of from 10 to 50, preferably from 10 to 30 amino acid residues. It is further preferred for the peptide linkers to be flexible linkers without a secondary structure. For example, suitable peptide linkers consist of at least 80% or at least 90%, preferably at least 95% or completely of glycine and/or serine residues. Particularly suitable are peptide linkers which contain a plurality of sequences SGGGG (SEQ ID NO 82).

In some preferred embodiments of the invention, the inventive γ-Netrin-binding peptides, particularly the Netrin1-binding peptides, are competitive with Netrin receptors and can even release a γ-Netrin, e.g. human Netrin1 or zebrafish Netrin1a or 1 b, bound to a Netrin receptor.

In a further aspect, the invention relates to a γ-Netrin-binding peptide as defined herein for use in medicine. A "use in medicine" in the context of the invention may be a use in therapy and/or a use in diagnostics. Preferably, the γ-Netrin-binding peptide, in particular the Netrin1-binding peptide, according to the invention is for use in human medicine, but it may also be used for veterinary purposes.

In particular, a γ-Netrin-binding peptide comprising (i) the sequence EVMPTLDMALFDWTDYEDLKP (SEQ ID NO.:1), or (ii) the sequence DVAPTFNMALFDWTDYEDMRP (SEQ ID NO.:2), or (iii) the sequence EVMPTLDMTLFDWTDYEDMKP (SEQ ID NO.:3), or (iv) a variant thereof having a sequence identity of at least 70%, at least 80%, at least 85%, at least 90%, or at least 95% to SEQ ID NO.:1, 2 and/or 3, which is optionally fused to a heterologous peptide or polypeptide, is for use in the prevention or treatment of a condition associated with, accompanied by or mediated by pathologic, particularly increased, γ-Netrin expression or activity. Preferably, the γ-Netrin is Netrin1.

A "pathologic expression or activity" of γ-Netrin, in particular Netrin1, as referred to herein is generally meant to encompass all situations, in which the ratio of expression and/or activity between Draxin and γ-Netrin and/or between γ-Netrin and at least one Netrin receptor is abnormal.

In particular, a "pathologic expression" means any level of expression, either on the DNA or the protein level, that differs from that of a normal healthy subject. Preferably, a pathologic γ-Netrin expression may be or may lead to a decreased γ-Netrin protein level or, more preferably, an increased γ-Netrin protein level, particularly an increased Netrin1 protein level, in a given (extracellular) environment of an organism. In accordance with preferred embodiments of the invention, the presence of an increased γ-Netrin level, particularly protein level, more particularly Netrin1 protein level, is defined as lying between 1 and 2 standard deviations above the average of healthy adults. Similarly, the presence of a decreased γ-Netrin protein level is defined as lying between 1 and 2 standard deviations below the average of healthy adults. For example, the γ-Netrin level in patient samples may be increased or decreased by a factor of at least 1,3 as compared to control samples from healthy adults.

A "pathologic activity" as referred to herein means in particular any activity of a protein that is abnormal. Preferably, a pathologic γ-Netrin activity may be a decreased or increased activity, e.g. binding to Netrin receptors with a lower or higher affinity. In accordance with preferred embodiments of the invention, the presence of an increased γ-Netrin activity, particularly Netrin1 activity, is defined as lying between 1 and 2 standard deviations above the average of healthy adults. Similarly, the presence of a decreased γ-Netrin activity is defined as lying between 1 and 2 standard deviations below the average of healthy adults. For example, the γ-Netrin activity in patient samples may be increased or decreased by a factor of at least 1,3 as compared to control samples from healthy adults.

A control group of "healthy adults" according to the invention can be determined by the skilled person with routine experimentation. For example, "healthy adults" for use as a possible control group herein may be healthy persons between 25 and 65 years of age, having a body mass index of 20-25, which may be sex-matched, if applicable.

The γ-Netrin-binding peptide for use as defined above may e.g. be a full-length Draxin from any vertebrate species, in particular human Draxin, rat Draxin, mouse Draxin, zebrafish Draxin A or zebrafish Draxin B. It may also be a variant of a full-length Draxin protein, characterized in that the variant differs in at least one, at least five, at least ten, at least 20 or even more amino acids from the complete sequence of the respective full-length Draxin protein, provided it retains the γ-Netrin-, in particular the Netrin1-binding activity. In preferred embodiments, the peptide is however significantly shorter as compared to full-length Draxin. For example, the peptide may have a length of up to 328, up to 324, up to 320, up to 300, up to 250, up to 200, up to 150, up to 100, up to 75 or up to 50 amino acids. In some preferred embodiments, the peptide has a length of up to 50 amino acids, e.g. 21 amino acids or 22 amino acids and is derived from zebrafish DraxinA. The peptide may or may not be fused to a heterologous peptide or polypeptide. Suitable peptides or polypeptides for fusion with the γ-Netrin-binding peptide are those described herein above, preferably protein tags, immunoglobulins (Ig) or functional fragments of immunoglobulins, wherein Ig Fc fragments, particularly human Ig Fc fragments are preferred. Still more preferably, the human Ig Fc fragment is a human IgG Fc fragment, e.g. a human IgG1, IgG2, IgG3, or IgG4 Fc fragment.

In some embodiments of the invention, the condition associated with, accompanied by or mediated by pathologic, particularly increased, γ-Netrin, preferably Netrin1 expression or activity is a hyperproliferative disease. A hyperproliferative disease according to the invention may be a tumor disease, a premalignant, non-neoplastic or non-malignant hyperproliferative disorder. In particular, the condition is a tumor disease.

An exemplary hyperproliferative disease which may be prevented or treated using the γ-Netrin-binding peptides, particularly Netrin1-binding peptides according to the invention is neoplastic lesions found in human inflammatory bowel disease (IBD).

Exemplary tumor diseases, which may be prevented or treated using the γ-Netrin-binding peptides, particularly Netrin1-binding peptides according to the invention, are selected from the group consisting of breast cancer, renal cancer, liver cancer, prostate cancer, colorectal cancer, lung cancer, neuroblastoma, meningioma of the brain, pituitary adenoma, glioma, glioblastoma, acute myeloid leukemia, sarcoma, melanoma, ovarian adenocarcinoma, renal adenocarcinoma, uterus adenocarcinoma, stomac adenocarcinoma, kidney adenocarcinoma and rectal adenocarcinoma, pancreatic cancer, inflammation driven cancers, particularly colorectal cancer, colorectal cancer associated with IBD, colorectal cancer associated with ulcerative colitis, colorectal cancer associated with Crohn's disease, and tumors derived from inflammatory bowel disease, including metastatic and particularly aggressive forms of these tumor diseases.

According to one embodiment, the tumor disease is neuroblastoma.

Preferably, the tumor disease is selected from the group consisting of pancreatic cancer, colorectal cancer, breast cancer, particularly metastatic breast cancer, and lung cancer, particularly non-small cell lung cancer.

In other embodiments of the invention, the condition associated with, accompanied by or mediated by pathologic γ-Netrin, particularly Netrin1 expression or activity is a cardiovascular disease, in particular atherosclerosis.

In still other embodiments of the invention, the condition associated with, accompanied by or mediated by pathologic γ-Netrin, particularly Netrin1 expression or activity is a neurological disorder, e.g. spinal cord injury.

The γ-Netrin-binding peptide, particularly Netrin1-binding peptide for use according to the invention may, according to a further aspect of the invention, also be present as an active agent in a pharmaceutical composition together with at least one pharmaceutically acceptable carrier. The present invention thus relates to a pharmaceutical composition comprising a γ-Netrin, particularly Netrin1-binding peptide or a salt or solvate thereof and at least one pharmaceutically acceptable carrier. Optionally, the pharmaceutical composition further comprises pharmaceutically acceptable excipients and/or adjuvants. Concentrations of these carriers, excipients and/or adjuvants, if used, are in a range that is physiologically acceptable.

A "carrier" as used herein must be physiologically acceptable and retain the therapeutic properties of the substance with which it is administered. Standard acceptable pharmaceutical carriers and their formulations are known to the skilled person. The carriers used will differ according to the administration route. Examples are magnesium carbonate, magnesium stearate, talc, sugar, lactose, pectin, dextrin, starch, gelatine, tragacanth, methylcellulose, sodium carboxymethylcellulose, a low melting-point wax, cocoa butter, water, alcohols, polyols, glycerol, vegetable oils, buffers etc.

As exemplary excipients, disintegrators, binders, fillers, and lubricants may be mentioned. Examples of disintegrators include agar-agar, algins, calcium carbonate, cellulose, colloid silicon dioxide, gums, magnesium aluminium silicate, methylcellulose, and starch. Examples of binders include microcrystalline cellulose, hydroxymethyl cellulose, hydroxypropylcellulose, and polyvinylpyrrolidone. Examples of fillers include calcium carbonate, calcium phosphate, tribasic calcium sulfate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, ethyl oleate, ethyl laureate, glycerin, glyceryl palmitostearate, hydrogenated vegetable oil, magnesium oxide, stearates, mannitol, poloxamer, glycols, sodium benzoate, sodium lauryl sulfate, sodium stearyl, sorbitol, and talc.

Usual stabilizers, preservatives, wetting and emulsifying agents, consistency-improving agents, flavour-improving agents, salts for varying the osmotic pressure, buffer substances, solubilizers, diluents, emollients, colorants and masking agents and antioxidants come into consideration as pharmaceutical adjuvants.

In yet a further aspect of the invention, the γ-Netrin-binding peptide, particularly Netrin1-binding peptide for use according to the invention may be widely combined with other therapeutically active agents, especially to achieve a synergistic effect in therapy and/or to be able to reduce the dosage of one or more active ingredients. Thus, the peptide is, in some embodiments, for use together with at least one additional therapeutically active agent, wherein the additional therapeutically active agent is particularly selected from the group consisting of decoy Netrin receptors, cytostatic agents, cytotoxic agents, statins, antihyperlipidemic agents, anti-coagulant agents, kinase inhibitors and angiogenesis modulators. Especially preferred therapeutic agents for combination with the γ-Netrin-binding peptide are cytostatic agents and cytotoxic agents.

A combination of a γ-Netrin-binding peptide, particularly a Netrin1-binding peptide, with at least one additional therapeutically active agent can be applied either by separate administration of the active ingredients to the patient or in the form of combination products in which a plurality of active ingredients are present in one pharmaceutical preparation. When the active ingredients are administered by separate administration of the active ingredients, this can be done simultaneously or consecutively.

The peptides according to the invention, either in an isolated form or as a pharmaceutical composition will typically be administered to a subject in need thereof, in particular a human subject. They will typically also be administered in a therapeutically effective amount, i.e. in an amount sufficient to achieve the desired effect. For example, one desired effect to be achieved by administration of γ-Netrin-binding peptides or anti-γ-Netrin antibodies or fragments or derivatives described herein may be to block, inhibit and/or neutralize one or more biological function of γ-Netrins, in particular of Netrin1, such as the binding to one or more Netrin receptor(s).

Administration of suitable compositions may be effected in different ways, e.g., by intravenous, intraperitoneal, subcutaneous, intramuscular, topical, oral, intradermal, intranasal or intrabronchial administration. Administration may also be conducted directly at the target site.

The necessary amount to be effective depends on a number of factors, such as the choice of the specific compound, the intended use, the administration route and the clinical condition of the patient. An appropriate "effective" amount in any individual case may be determined by a skilled person in the art, e.g. a skilled physician, using routine experimentation. An exemplary "therapeutically effective amount" of a peptide according to the invention may be about 0.01 mg to 50 mg/dose, preferably 0.1 mg to 10 mg/dose.

In yet a further aspect, the invention relates to an antibody or fragment or derivative thereof directed against Draxin, which inhibits binding of Draxin to γ-Netrins, in particular to Netrin1.

In yet a further aspect, the invention relates to an antibody or fragment or derivative thereof directed against Netrin1, which inhibits binding of at least one γ-Netrin, in particular of Netrin1, to at least one Netrin receptor, and which is directed against an epitope between amino acids 285-451 of human Netrin1. In particular, the antibody inhibits binding of at least one γ-Netrin, preferably Netrin1 to at least one of DCC (Deleted in colorectal cancer), DSCAM, DSCAM-L1, PTPRF (protein tyrosine phosphatase, receptor-type F), NEO (Neogenin), ADORA2B (adenosine A2B), Nope (Neighbor Of Punc E1 1), and members of the UNCSH family (Uncoordinated-5 homologues; UNC5H1, UNC5H2, UNC5H3, UNC5H4).

The term "antibody" as used herein particularly refers to molecules comprising at least one immunoglobulin heavy chain and at least one immunoglobulin light chain. Each heavy and light chain may comprise a variable and a constant domain. The antigen-binding site may be formed from the variable domains of a heavy and a light chain. A variable region (also referred to as variable domain) comprises complementarity determining regions (CDRs), e.g. a CDR1, a CDR2 and a CDR3 region, and framework regions (FRs) flanking the CDRs. The term "complementarity determining region" is readily understood by the skilled person (see, for example, Harlow and Lane (eds.), Antibodies: A Laboratory Manual, CSHL Press, Cold Spring Harbor, N.Y., 1988; incorporated herein by reference in its entirety) and refers to the stretches of amino acids within the variable domain of an antibody that primarily make contact with the antigen and determine antibody specificity. This region is also known as the hypervariable region.

The term "(functional) antibody fragment or derivative thereof" as used herein encompasses fragments of antibodies, especially of human or humanized antibodies, such as portions of the above-mentioned antibodies which comprise at least one antigen-binding site. Examples of antibody fragments according to the invention include Fab fragments, Fab' fragments, $F(ab')_2$ fragments, Fv fragments, diabodies or single chain antibody molecules and other fragments as long as they exhibit the desired capability of binding to their target antigen, e.g. Draxin or at least one γ-Netrin. As exemplary single chain antibody molecules, scFv and nanobodies (VHH) are mentioned.

In case of antibodies or fragments or derivatives thereof directed against Draxin, only those antibodies, fragments and derivatives which inhibit the binding of Draxin to at least one γ-Netrin, preferably to Netrin1 are encompassed by the invention.

Likewise, in case of antibodies or fragments or derivatives thereof directed against γ-Netrin(s), only those antibodies, fragments and derivatives which inhibit the binding of at least one γ-Netrin, preferably Netrin1, to at least one Netrin receptor are encompassed by the invention.

Such inhibition can be determined by the skilled person via routine experimentation, e.g. via binding assays.

The term "bind" or "binding" of e.g. an antibody as used herein means an at least temporary interaction or association with or to e.g. a target antigen, e.g. Draxin or a γ-Netrin, comprising fragments thereof containing an epitope.

In preferred embodiments, the antibody directed against Draxin (i.e. the anti-Draxin antibody) according to the invention binds to an epitope on Draxin, which is located between amino acid residues 209-284, preferably between amino acid residues 226-257, of a zebrafish Draxin, preferably zebrafish DraxinA. More preferably, the antibody binds to an epitope between amino acids 232-252 of zebrafish DraxinA.

In further preferred embodiments, the anti-Draxin antibody according to the invention binds to an epitope on Draxin, which is located in a region of human Draxin corresponding to amino acid residues 209-284, preferably between amino acid residues 226-257, of zebrafish Draxin, preferably zebrafish DraxinA. More preferably, the antibody binds to an epitope between amino acids 222-243 of human Draxin.

In preferred embodiments, the antibody directed against γ-Netrin (i.e. the anti-γ-Netrin antibody) according to the invention binds to an epitope on Netrin1, which is located between amino acid residues 285-451 (i.e. EGF1-3), preferably between amino acid residues 341-451 (i.e. EGF2-3), of human Netrin1 or a corresponding epitope in another γ-Netrin and/or another species, preferably to an epitope located in the EGF1-3 domains, preferably the EGF2-3 domains of zebrafish Netrin1a and/or Netrin1b. More preferably, the antibody binds to an epitope between amino acids 404-451 (i.e. EGF3) of a human γ-Netrin, preferably human Netrin1 or to an epitope located in the EGF3 domain of a zebrafish γ-Netrin, preferably zebrafish Netrin1a or Netrin1b.

The antibody or fragment or derivative thereof according to the invention may be derived from any antibody-producing animal species. Preferably, it is a mouse, rat or human antibody or functional antibody fragment or antibody derivative. The antibody may be a polyclonal antibody, a monoclonal antibody, a chimeric antibody, and/or a recombinant antibody. Monoclonal antibodies, in particular human or humanized monoclonal antibodies are preferred.

A monoclonal antibody (also referred to as mAB) is a single molecular species of antibody and is usually produced by creating hybrid antibody-forming cells from a fusion of nonsecreting myeloma cells with immune spleen cells. Polyclonal antibodies, by contrast, are produced by injecting an animal (such as a rodent, rabbit or goat) with an antigen, and extracting serum from the animal. A chimeric antibody is an antibody in which the variable domain of e.g. a murine antibody is combined with the constant region of a human antibody. Recombinant antibodies are obtained via genetic engineering without having to inject animals. Human antibodies according to the invention may be prepared using transgenic mice or by phage display; these methods are well known in the art.

In yet a further aspect, the antibodies or fragments or derivatives thereof according to the invention are for use in medicine (as defined above), particularly human medicine. For example, they may be used in diagnostics to determine qualitatively or quantitatively their respective antigens; they may also be used as a diagnostic agent for diseases with pathologic, in particular increased target expression.

In certain embodiments of yet a further aspect, the anti-γ-Netrin antibody (including its functional fragments and derivatives as defined herein) is for use in the prevention or treatment of a condition associated with, accompanied by or mediated by pathologic, particularly increased, γ-Netrin, particularly Netrin1 expression or activity, as defined herein above. This condition is preferably a hyperproliferative disease, in particular a tumor disease.

Exemplary tumor diseases, which may be prevented or treated using the anti-γ-Netrin antibody, preferably anti-Netrin1-antibody, or fragments or derivatives thereof according to the invention, are selected from the group consisting of breast cancer, renal cancer, liver cancer, prostate cancer, colorectal cancer, lung cancer, neuroblastoma, meningioma of the brain, pituitary adenoma, glioma, glioblastoma, acute myeloid leukemia, sarcoma, melanoma, ovarian adenocarcinoma, renal adenocarcinoma, uterus adenocarcinoma, stomac adenocarcinoma, kidney adenocarcinoma and rectal adenocarcinoma, pancreatic cancer, inflammation driven cancers, particularly colorectal cancer, colorectal cancer associated with IBD, colorectal cancer associated with ulcerative colitis, colorectal cancer associated with Crohn's disease, and tumors derived from inflammatory bowel disease, including metastatic and particularly aggressive forms of these tumor diseases.

Preferably, the tumor disease is selected from the group consisting of pancreatic cancer, colorectal cancer, breast cancer, particularly metastatic breast cancer, and lung cancer, particularly non-small cell lung cancer. In another embodiment, the tumor disease is neuroblastoma.

The anti-γ-Netrin antibody, preferably anti-Netrin1-antibody or fragment or derivative thereof may also be present in the form of a pharmaceutical composition as defined above, and may also be used in combination with further pharmaceutically active agents, particularly one or more agent selected from the group consisting of decoy Netrin receptors, cytostatic agents, cytotoxic agents, statins, antihyperlipidemic agents, anti-coagulant agents, kinase inhibitors and angiogenesis modulators. Especially preferred therapeutic agents for combination with the anti-γ-Netrin-antibody are cytostatic agents and cytotoxic agents.

In certain embodiments of yet a further aspect, the anti-Draxin antibody (including its functional fragments and derivatives as defined herein) is for use in the prevention or treatment of a condition associated with, accompanied by or mediated by pathologic, particularly decreased, γ-Netrin, particularly Netrin1 expression or activity, as defined herein above. Likewise, the anti-Draxin antibody (including its functional fragments and derivatives as defined herein) may be used in the prevention or treatment of a condition associated with, accompanied by or mediated by pathologic, particularly increased, Draxin expression or activity.

This condition may be a cardiovascular disorder, in particular a cardiovascular disorder which can be prevented or treated by increasing γ-Netrin, in particular Netrin1 expression and/or activity. Exemplary cardiovascular disorders are selected from ischemia/reperfusion (I/R) injury, e.g. renal I/R injury, I/R injury of cardiac tissue; myocardial infarction, particularly infarcts resulting from I/R injury; mitochondrial damage; neointimal formation and restenosis; vascular injury or vascular dysfunction; vascular smooth muscle cell migration and proliferation; apoptosis of endothelial progenitor cells, procure induced restenosis; and hypertension.

A "pathologic expression or activity" of Draxin is generally meant to encompass all situations, in which the ratio of expression and/or activity between Draxin and any γ-Netrin is abnormal. Particularly, a pathologic Draxin expression may be or may lead to a decreased Draxin protein level or, preferably, an increased Draxin protein level in a given (extracellular) environment of an organism. A pathologic Draxin activity may be an decreased or increased activity, e.g. binding to a γ-Netrin, particularly Netrin1 with a lower or higher affinity.

In yet a further aspect, the present invention relates to peptides which bind to Draxin, in particular to human Draxin and/or zebrafish DraxinA and/or zebrafish DraxinB, with a high specificity and a high affinity.

Accordingly, the invention provides a Draxin-binding peptide comprising (i) at least consecutive amino acids from the sequence KACDCHPVGAAGKTCNQTTGQCPCKDGVTGITCNRCANGYQQSRSPIAPCIKIPIA PP (SEQ ID NO.: 51) or (ii) a variant thereof having a sequence identity of at least 70%, at least 80%, at least 85%, at least 90%, or at least 95% to SEQ ID NO.:51, wherein said peptide has a length of up to 580 amino acids and is optionally fused to a heterologous peptide or polypeptide.

In particular, the Draxin-binding peptide comprises at least 20, at least 30, at least 40, at least 50 consecutive amino acids from SEQ ID NO.:51 or the complete SEQ ID NO.: 51 or a variant thereof having a sequence identity of at least 70%, at least 80%, at least 85%, at least 90%, or at least 95% to SEQ ID NO.:51.

In some embodiments, the peptide has a length of up to 580 amino acids, up to 500 amino acids, up to 400 amino acids, up to 300 amino acids, up to 250 amino acids, up to 200 amino acids, up to 100 amino acids, up to 75 amino acids, or up to 60 amino acids. Fragments comprising up to 60 amino acids are preferred according to some embodiments.

In some embodiments, the peptide with a length of up to 580 amino acids comprises SEQ ID NO.: 51 or a variant thereof having a sequence identity of at least 70%, at least 80%, at least 85%, at least 90%, or at least 95% to SEQ ID NO.: 51 and is free of any further heterologous peptides.

In other embodiments, the peptide with a length of up to 580 amino acids comprises SEQ ID NO.: 51 or a variant thereof having a sequence identity of at least 70%, at least 80%, at least 85%, at least 90%, or at least 95% to SEQ ID NO.: 51 and is fused to a heterologous peptide or polypeptide as defined above, preferably protein tags, immunoglobulins (Ig) or functional fragments of immunoglobulins, wherein Ig Fc fragments, particularly human Ig Fc fragments are preferred. Still more preferably, the human Ig Fc fragment is a human IgG Fc fragment, e.g. a human IgG1, IgG2, IgG3, or IgG4 Fc fragment.

In some embodiments, the peptide may also be fused to a heterologous signal sequence, e.g. a human Netrin1-fragment comprising SEQ ID NO.: 51 may be fused to a zebrafish signal sequence (comprising e.g. SEQ ID NO.: 70 or 71), as shown in SEQ ID NOs.: 68 and 69.

In a further aspect, the invention relates to a Draxin-binding peptide as defined herein for use in medicine, particularly human medicine.

In certain embodiments of yet a further aspect, the Draxin-binding peptide described herein is for use in the prevention or treatment of a condition associated with, accompanied by or mediated by pathologic, particularly decreased, γ-Netrin, in particular Netrin1 expression or activity, as defined herein above. Likewise the Draxin-binding peptide may be used in the prevention or treatment of a condition associated with, accompanied by or mediated by pathologic, particularly increased, Draxin expression or activity.

This condition may be a cardiovascular disorder, in particular a cardiovascular disorder which can be prevented or treated by increasing γ-Netrin, in particular Netrin1 expression and/or activity. Exemplary cardiovascular disorders are selected from ischemia/reperfusion (I/R) injury, e.g. renal I/R injury, I/R injury of cardiac tissue; myocardial infarction, particularly infarcts resulting from I/R injury; mitochondrial damage; neointimal formation and restenosis; vascular injury or vascular dysfunction; vascular smooth muscle cell migration and proliferation; apoptosis of endothelial progenitor cells, procure induced restenosis; and hypertension.

The Draxin-binding peptide for use according to the invention may, according to a further aspect of the invention, also be present as an active agent in a pharmaceutical composition together with at least one pharmaceutically acceptable carrier. The present invention thus relates to a pharmaceutical composition comprising an Draxin-binding peptide thereof and at least one pharmaceutically acceptable carrier and, optionally, pharmaceutically acceptable excipients and/or adjuvants.

Still a further aspect of the present invention is a method for the treatment of a condition associated with, accompanied by or mediated by pathologic, particularly increased or decreased γ-Netrin, in particular Netrin1 expression or activity, comprising administering a γ-Netrin-binding peptide, a Draxin-binding peptide, an anti-γ-Netrin antibody and/or an anti-Draxin antibody as described herein above to a subject, particularly a human subject in need thereof. In particular, this subject suffers from a hyperproliferative disorder as defined above.

The invention also refers to a nucleic acid molecule, preferably an isolated nucleic acid molecule, encoding a γ-Netrin-binding peptide, particularly the Netrin1-binding peptide, the Draxin-binding peptide, and the antibodies or fragments or derivatives thereof directed against γ-Netrin, in particular Netrin1, and/or Draxin as described above. The term "nucleic acid molecule" encompasses a natural DNA or RNA or a recombinantly or synthetically produced DNA, RNA or LNA or a recombinantly produced chimeric nucleic acid molecule comprising any of these nucleic acids either alone or in combination. For example, the nucleic acid may be cDNA or genomic DNA corresponding to an entire gene or a substantial portion thereof or to fragments and derivatives thereof. The nucleotide sequence may correspond to the naturally occurring nucleotide sequence or may contain single or multiple nucleotide substitutions, deletions or additions. The nucleic acid may also be fused to another nucleic acid. The nucleic acid molecule of the invention may be in operative linkage to an expression control sequence, i.e. to a sequence which is necessary to effect the expression of coding nucleic acid sequences. Such expression control sequences may include promoters, enhancers, ribosomal binding sites and/or transcription termination sequences. Specific examples of suitable expression control sequences are known in the art.

The nucleic acid molecule of the invention may be located on a vector which may additionally contain a replication origin and/or a selection marker gene. Examples of vectors are plasmids, cosmids, phages, viruses etc.

Further, the invention refers to a recombinant cell, which comprises the nucleic acid molecule as described above. The nucleic acid molecule may be introduced into the recombinant cell by transformation, transfection or transduction according to any method known in the art. The recombinant cell may e.g. be a prokaryotic or eukaryotic cell. Preferably, the cell is a mammalian cell, e.g. a hamster, rabbit, or human cell. Preferably, the cell is a human cell.

The γ-Netrin-binding peptide, the Draxin-binding peptide, and the antibodies or fragments or derivatives thereof directed against γ-Netrin and/or Draxin of the invention may be prepared by a method, wherein the cell as described above is cultured under conditions which allow expression of the antibody encoding nucleic acid molecule. The antibody may be collected from the cultured cell or the culture supernatant. Preferably, the antibody is prepared from a mammalian, particularly from a human cell.

Also encompassed by the invention are salts and solvates, preferably pharmaceutically acceptable salts and solvates of the disclosed peptides, in particular of the γ-Netrin-, preferably Netrin1-binding peptides and the Draxin-binding peptides.

Pharmaceutically acceptable salts may include, but are not limited to, acid addition salts and basic salts. Examples of acid addition salts include chloride, sulfate, hydrogen sulfate, (hydrogen) phosphate, acetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts.

A "solvate" is a complex of a peptide of the invention or a salt thereof with solvent molecules, e.g. organic solvent molecules and/or water.

BRIEF DESCRIPTION OF THE FIGURES

FIG. 1. Draxin directly binds Netrin1.

A) AVEXIS screen results showing that the DraxinA prey protein, in addition to the positive control bait Matn4 (+), only binds to Netrin1a in a protein library consisting of 171 bait proteins. B) Interaction network of the zebrafish Netrin1 and Draxin paralogs. Consecutive screen results show that the interaction is also conserved for the paralogs.

Figure 2:
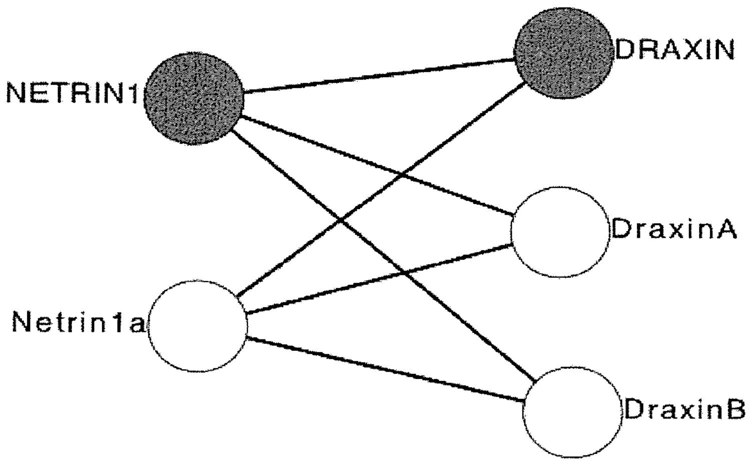

FIG. 2. The binding of Draxin to Netrin1 is conserved for the human homologs and detectable across human and zebrafish proteins.

Heatmap showing results from the AVEXIS assay. The screen has been performed in both bait-prey orientations using pentameric prey proteins. Absorbance at 486 nm (A486 nm) has been measured after 1-hour incubation (black: A486 nm>0.1=binding, grey: A486 nm 0.08-0.1=weak binding, 2 repeats). B) Network view of the results.

FIG. 3. Draxin protein alignment using the Clustal W method.

The alignment of human, mouse, chick, and zebrafish DraxinA and DraxinB protein shows that the N-terminal half of the protein is poorly conserved. In the most C-terminal part of the protein a conserved 10-cysteine containing region can be found, which resembles the cysteine-rich region present in Dickkopf proteins.

FIG. 4. A conserved 21aa DraxinA derived peptide is sufficient for the binding to Netrin1a.

A) By using a set of truncated and deletion containing monomeric DraxinA preys the binding interface of DraxinA to Netrin1a has been mapped down to a 21 amino acid region (aa232-aa252). The protein fragments binding to Netrin1a are indicated in black, weak binding ones in grey, and non binding fragments are depicted in white. B) and C): Using a similar approach the DraxinA binding interface in Netrin1a has been narrowed down to the third EGF-domain containing region (aa401-aa458).

FIG. 5. Multiple species alignment of the Draxin derived 21 aa peptide sequence.

The figure shows that the Netrin1 binding peptide is highly conserved in vertebrates.

Figure 6:
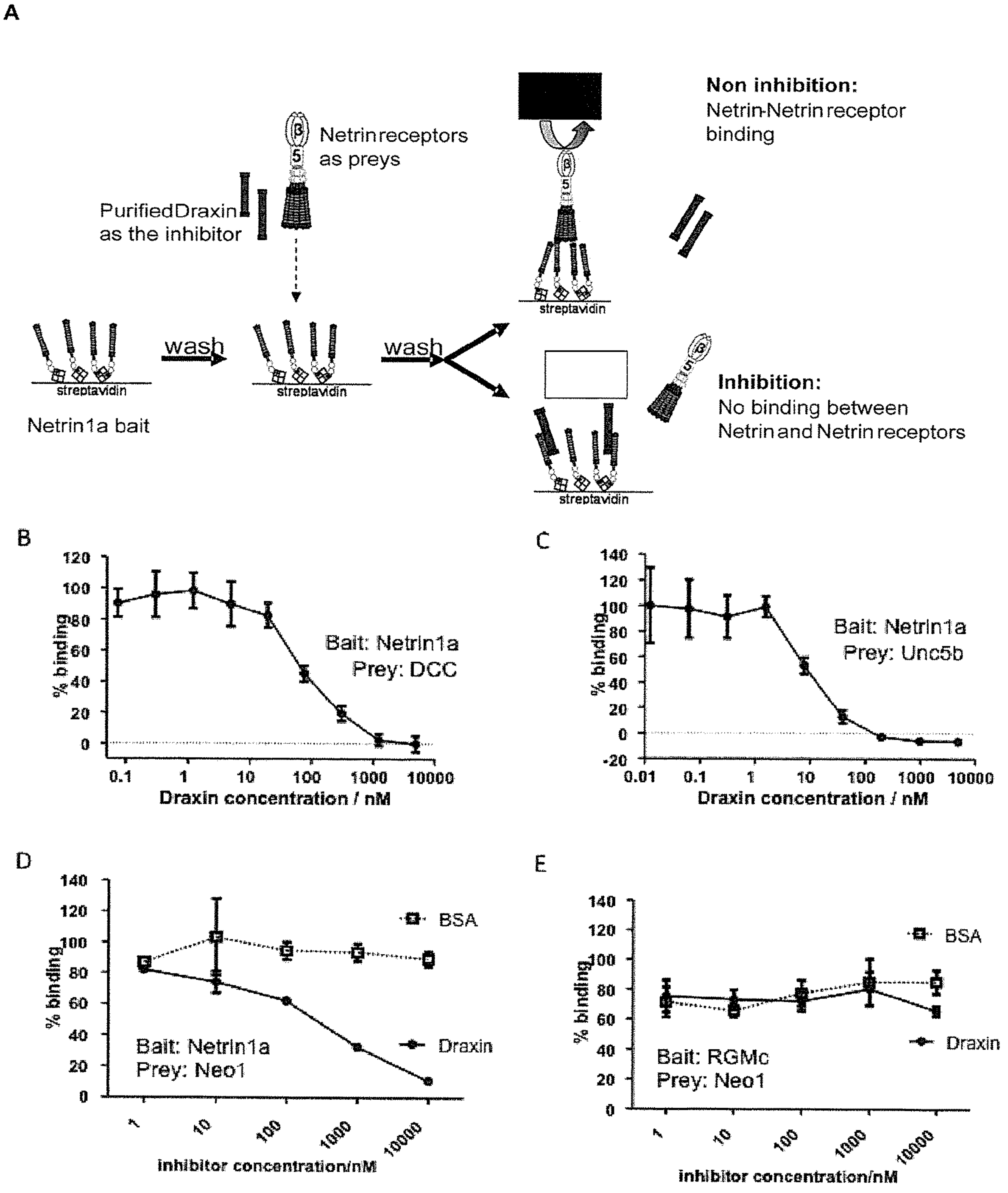

FIG. 6. DraxinA inhibits the binding of Netrin1a to Netrin receptors.

A) Schematic representation of the AVEXIS based competition assay. B) Purified full-length Draxin inhibits the binding of of the Netrin1a bait to the DCC-prey proteins. C) This effect can also be seen for the Unc5b and Neo1 (D) netrin receptors. Equal amounts of BSA (D) are not able to inhibit the binding between Netrin and Neo1. E) Draxin is not able to interfere with the binding of RGMc to Neo1. RGMc is another known Neo1 ligand. (% binding: binding with inhibitor/binding without inhibitor ×100%, error bars indicate mean±s.d.; n=4)

Figure 7:
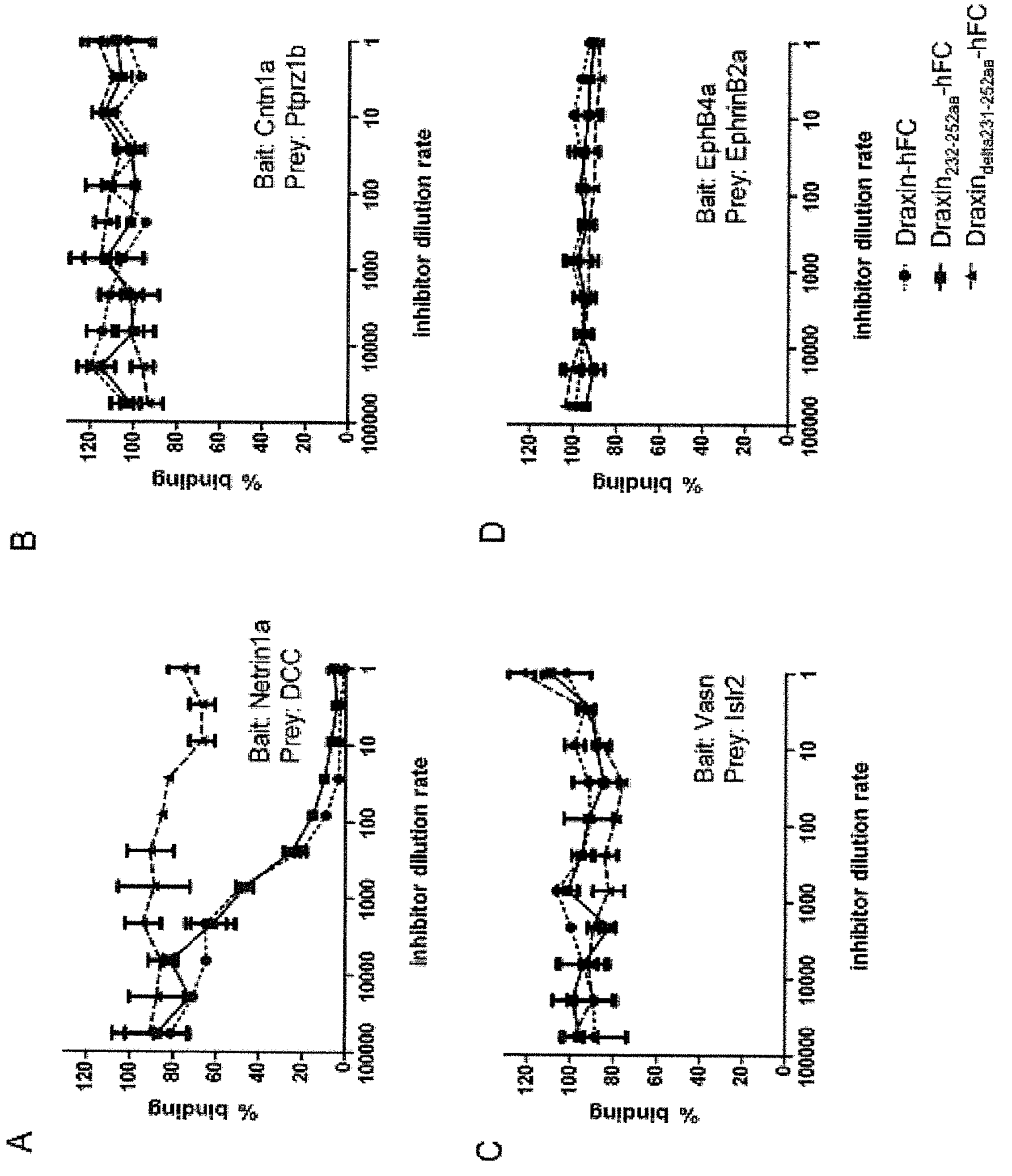

FIG. 7. A 21 amino acid fragment of Draxin is sufficient to outcompete Netrin/Netrin receptor interactions.

A) Full-length DraxinA-hFc and the 21aa peptide fused to the hFc region are able to outcompete DCC for binding to Netrin1a. In contrast the hFc fusion of full-length DraxinA with a deletion of aa231-252 is not able to compete for binding. None of the 3 DraxinA-hFc fusion protein versions is able to block the binding between other known tested receptor-ligand pairs: (B) Cntn1a/Ptprz1b, (C) Vasn/Islr2, and (D) EphB4a/EphrinB2a. (% binding: binding with inhibitor/binding without inhibitor ×100%, error bars show mean±s.d.; n=3)

Figure 8:
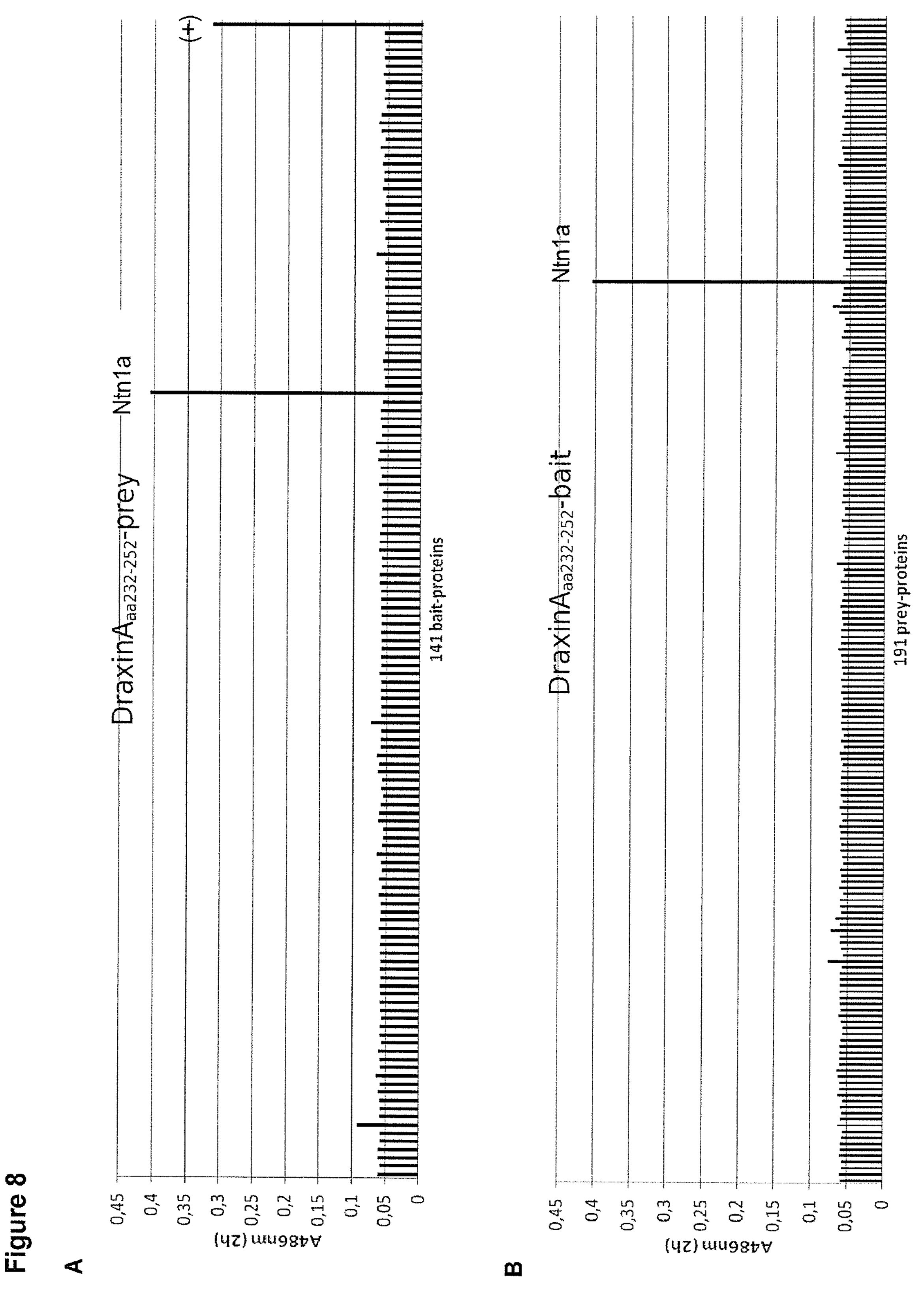

FIG. 8. The binding of the 21aa DraxinA derived peptide is highly specific.

A) A pentameric DraxinA aa232-252-prey protein has been screened against a library consisting of 141 bait proteins. We only observed binding to the Netrin1a-bait. The positive control (+) corresponds to Matn4. B) The DraxinA aa232-252-bait has been screened against 191 pentameric prey proteins and only showed binding to the Netrin1a prey.

Figure 9:
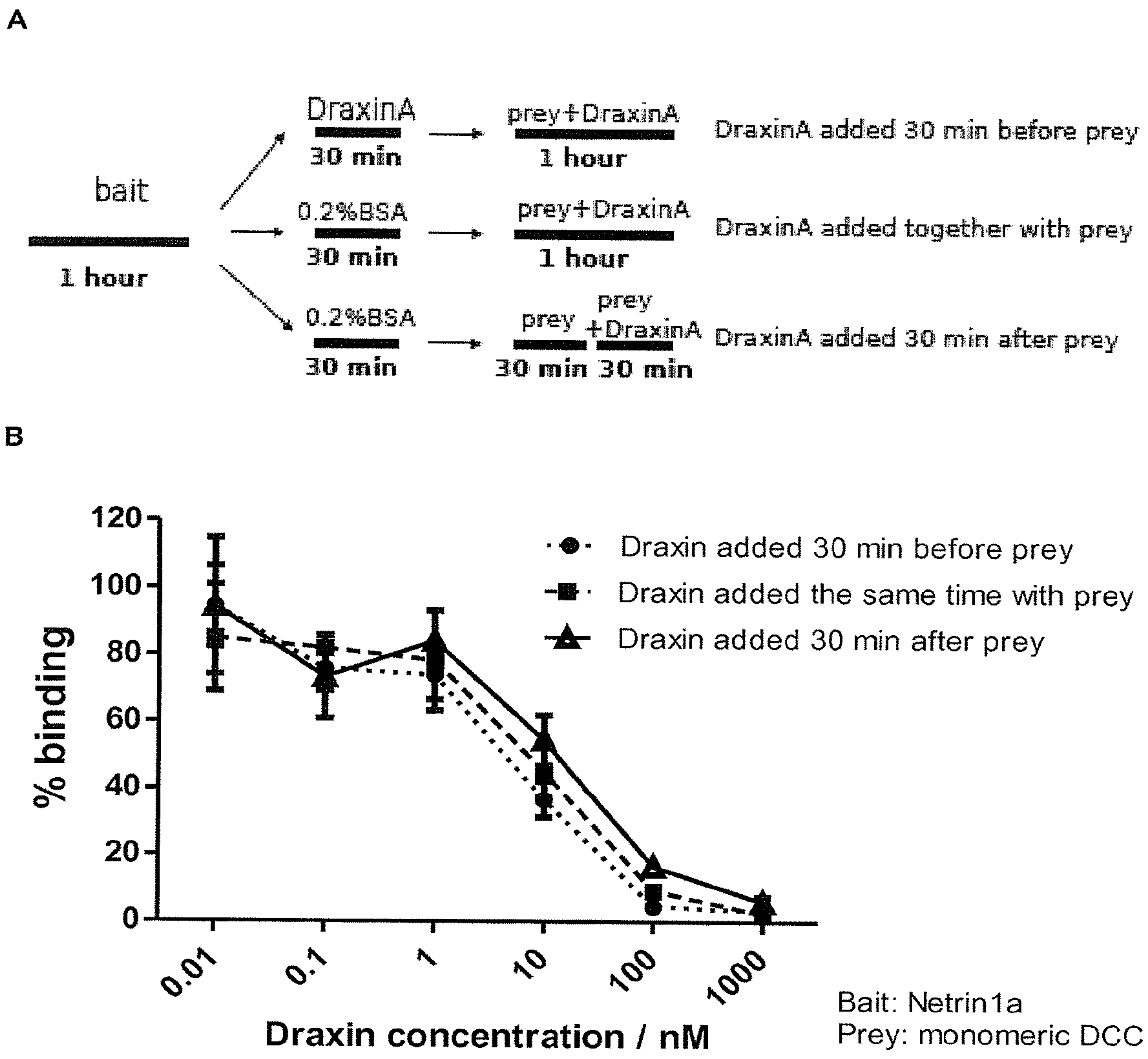

FIG. 9. Draxin outcompetes receptor bound Netrin1a.

A) Scheme of the experimental design. B) The inhibitory effect of DraxinA is not decreased by already preformed Netrin1a/DCC complexes.

FIG. 10: Protein alignment of the third EGF domain of Netrins.

Protein alignment of the third EGF domain of human Netrin1, Netrin3, Netrin4 and zebrafish Netrin1a and Netrin1b shows that this domain is highly conserved for the γ-chain netrins but not for Netrin4 which belongs to the laminin1 β-chain derived netrins. In agreement with the protein alignment data our AVEXIS binding data indicate that only γ-chain derived Netrins can bind to Draxin.

FIG. 11: In vivo detection of the Draxin-Netrin1a interaction in zebrafish embryos.

A) Schematic illustration of the assay design. mRNAs encoding the indicated fluorophore tagged genes were injected into one-cell stage zebrafish embryos and imaged at sphere stage (4 hours post fertilization (hpf)). The imaging plane corresponded to a region approximately 15 μm beneath the enveloping layer of the embryos.

B) Single section confocal images of the embryos. (Ba, Ba', Ba") embryos injected with 100 pg Draxin-super folder GFP (sfGFP) mRNA displayed uniform distribution of Draxin-sfGFP protein in the extracellular space. In contrast injection of 100 pg of Netrin1a-sfGFP mRNA (Bb, Bb', Bb") resulted in dense membrane associated speckles positive for Netrin1a-sfGFP protein. In (Ba) and (Bb) memRFP has been used to label the cell surface. Upon co-injections of 200 pg Draxin-sfGFP mRNA and 200 pg of Netrin1a-mCherry mRNA (Bc, Bc', Bc") Draxin-sfGFP and Netrin1a-mCherry proteins co-localize into membrane associated spots. (n=7; arrowheads point to examples of co-localization; scale bars correspond to 10 μm).

Figure 12:
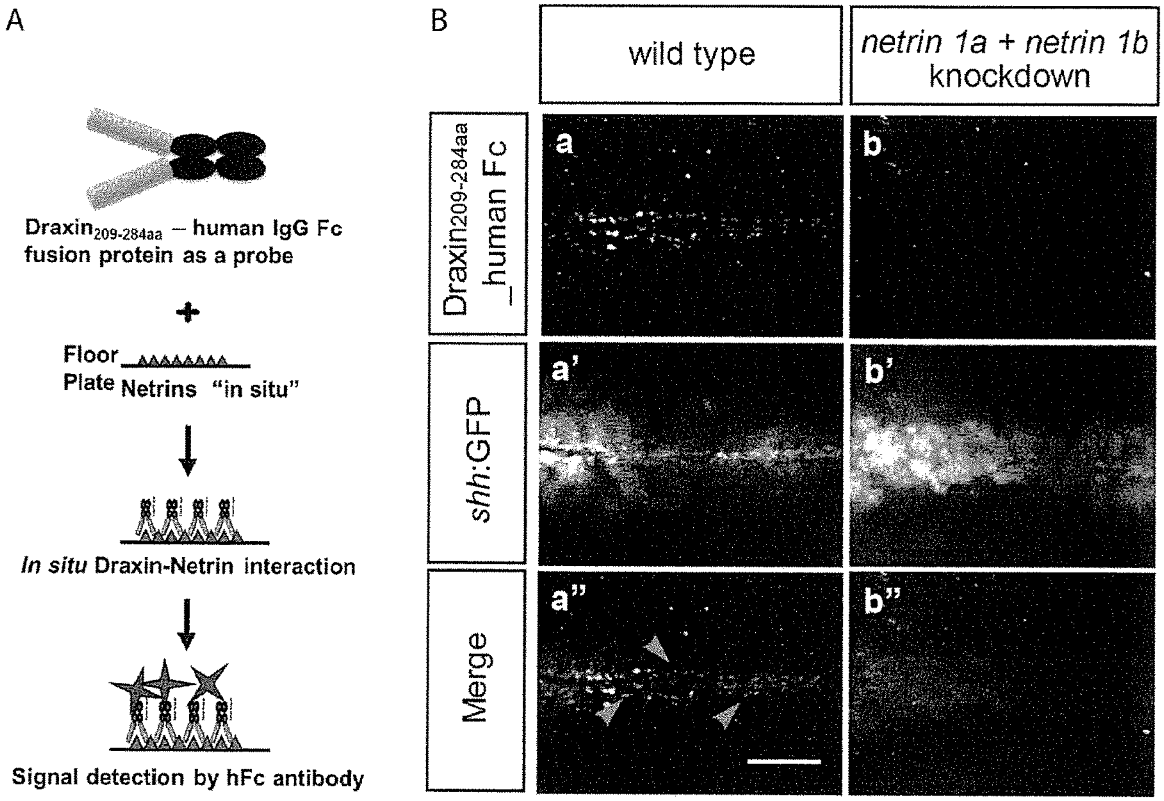

FIG. 12: In situ detection of the Draxin-Netrin1a interaction in zebrafish using an affinity probe.

A) Schematic illustration of the experiment. A $Draxin_{aa209-284}$-hFc-fusion protein was generated in HEK293-6E cells as a probe to detect endogenous netrins. Mildly fixed 48 hpf embryos were incubated with the affinity probe ($Draxin_{aa209-284}$-hFc) and the signal detection has been carried out by using a fluorophore tagged anti human IgG antibody.

B) Results of the in situ detection experiments. The signal from $Draxin_{aa209-284}$-hFc-fusion probe was detectable in the floor plate region in wild type (also abbreviated as wt) fish (Ba), and was not detectable in netrinla and netrinlb double-knockdown embryos (Bb). The shh:GFP transgenic line has been used for the experiments to visualize floor plate cells. Arrowheads point to the $Draxin_{aa209-284}$-hFc derived signal. Scale bar in (Ba"), 20 μm; applies to all panels. (n>10)

FIG. 13: Heatmap depicting binding results between human DRAXIN and Netrin signaling system members.

AVEXIS was used to test pairwise binding events in both bait/prey orientations between human DRAXIN, the derived 21 amino acid peptide, human Netrin family members, and two representative Netrin receptors (DCC, UNC5B). The Matn4-bait served as an internal prey-protein control and was used for normalization of the A486 nm values; conditioned medium (CM) serves as negative control; n=3.

Figure 14:
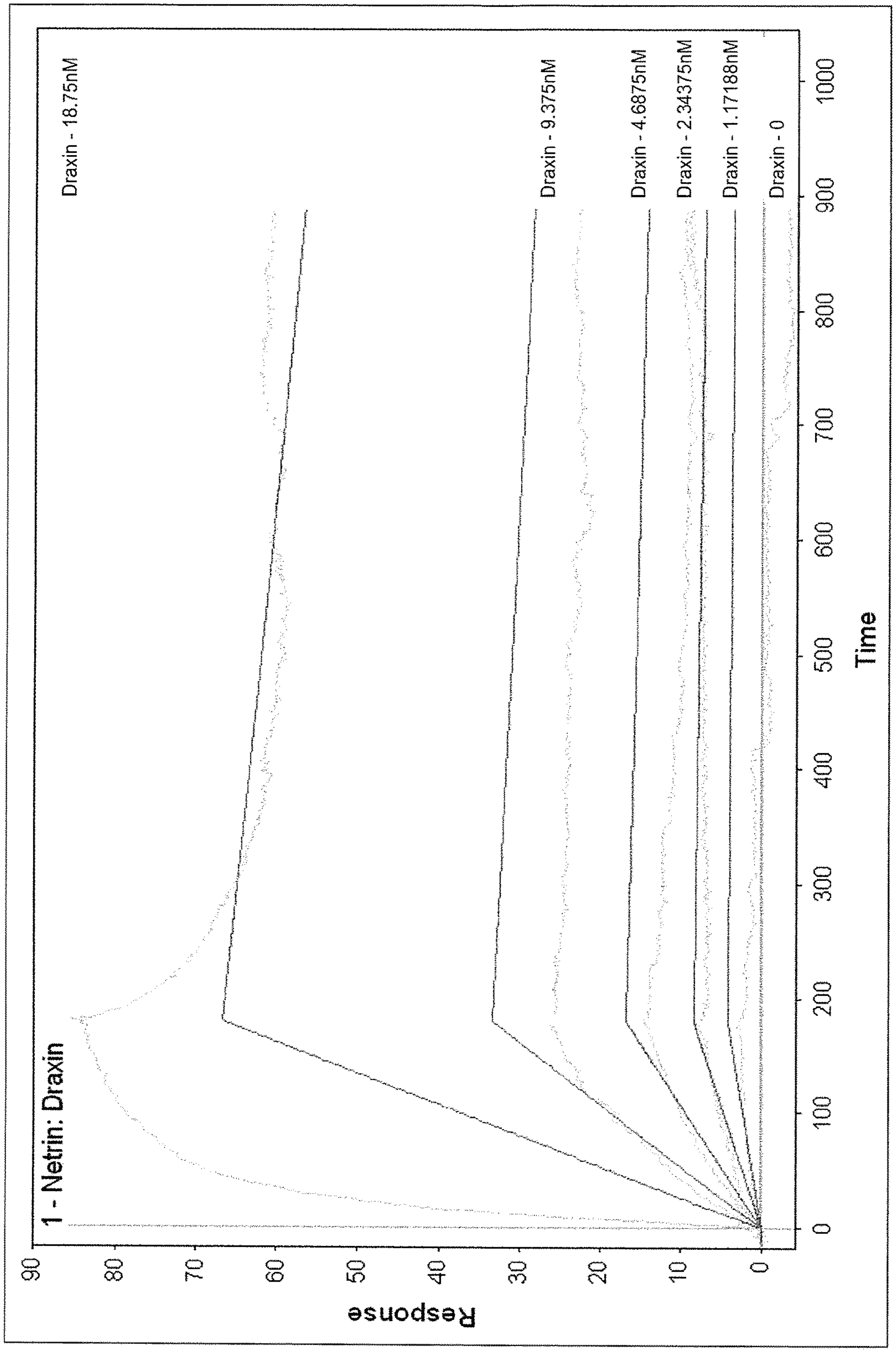
Figure 14:
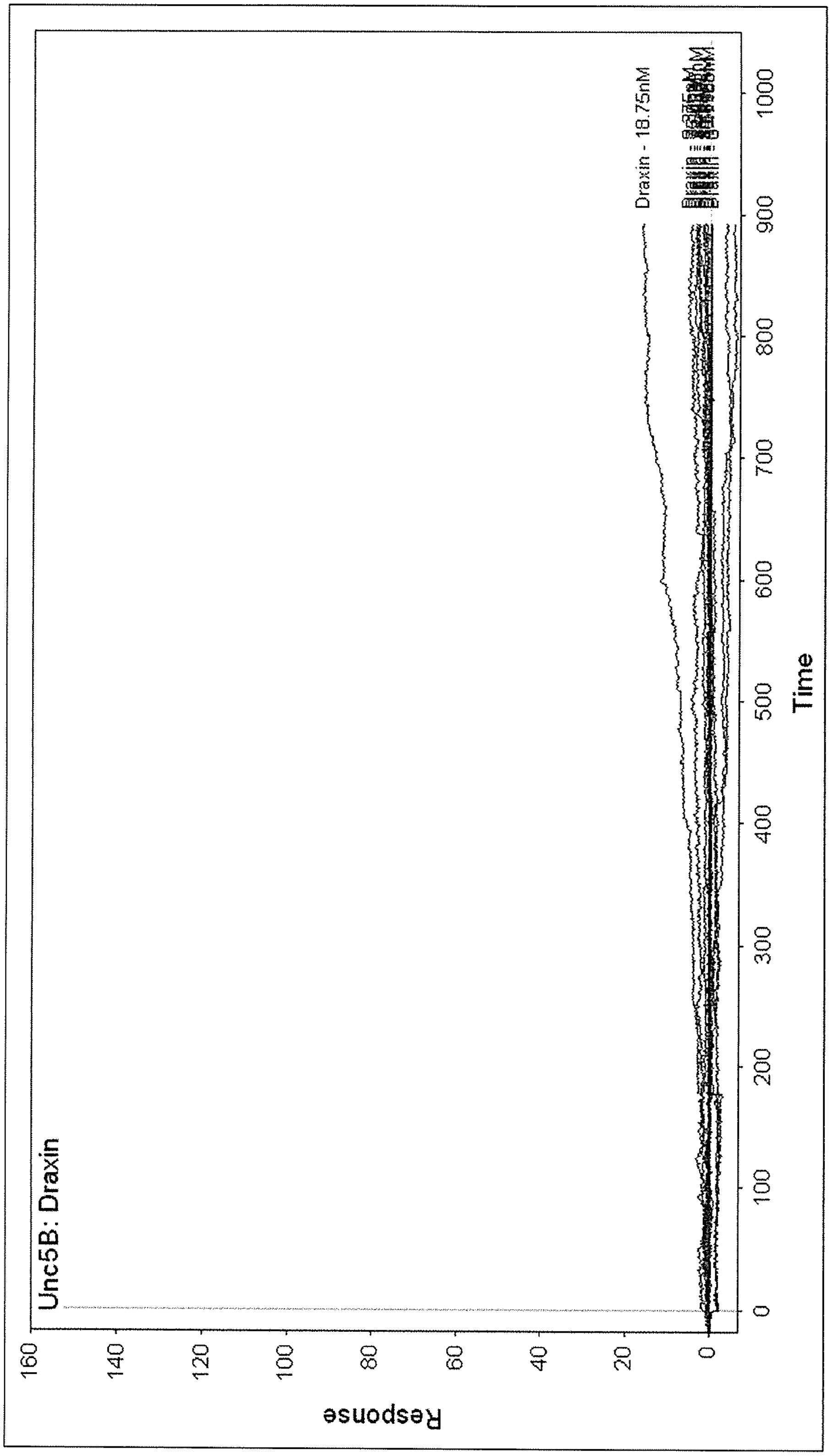
Figure 14:
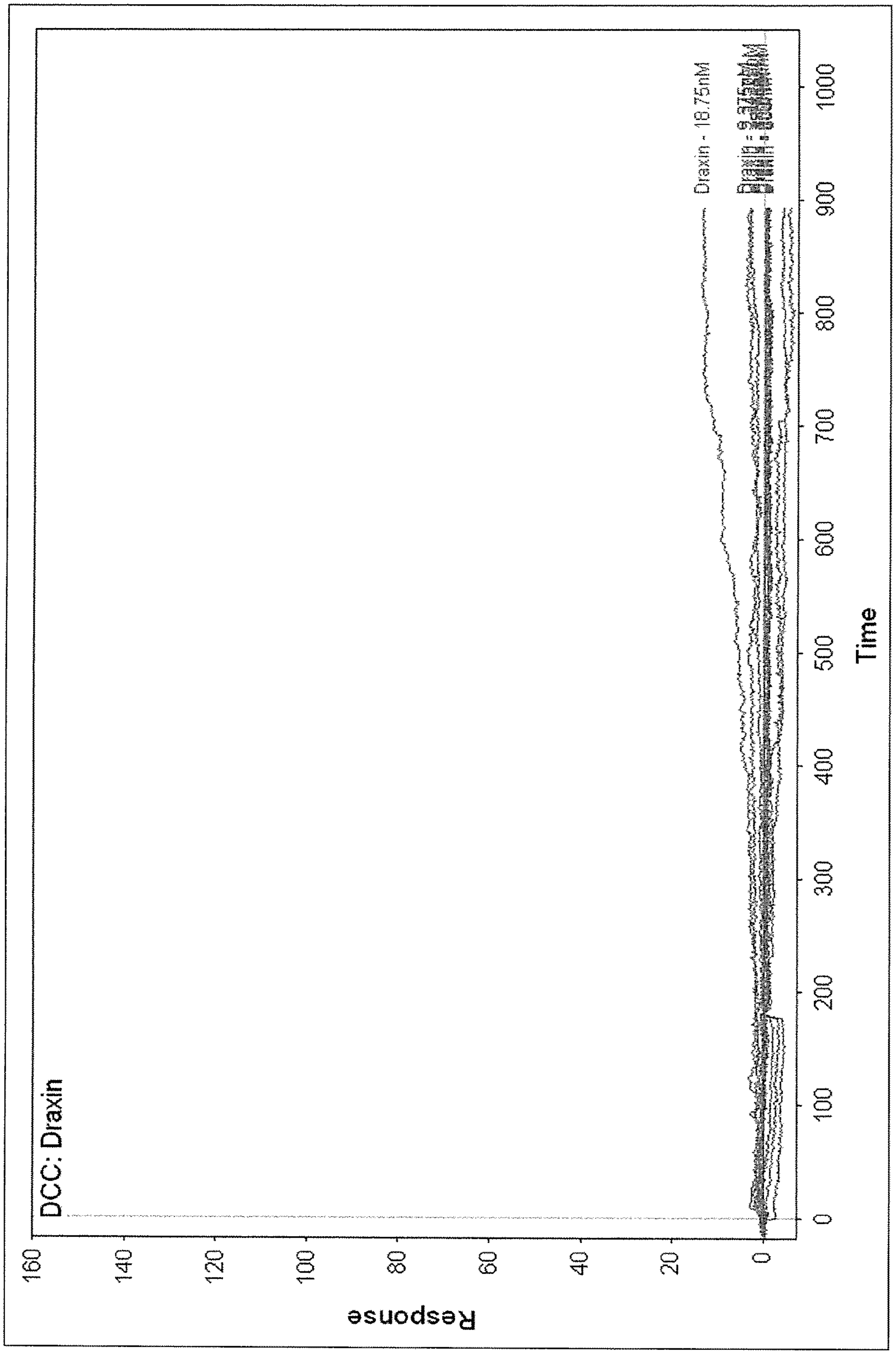

FIG. 14: Surface Plasmon Resonance Analysis of Draxin Binding.

Binding of Draxin to immobilised recombinant human Netrin1, UNC5B, and DCC was monitored using Surface Plasmon Resonance experiments on a Siacore 3000 instrument. See text for details.

The invention will be further illustrated by the following examples.

EXAMPLES

Methods

AVEXIS Based Library Screen

To detect extracellular protein-protein interactions in a high-throughput manner we used the AVEXIS assay as described in Bushell et al. (Bushell et al., 2008) with minor modifications.

In brief: A zebrafish protein library enriched for mainly in neuronal tissues expressed secreted proteins and extracellular domains of cell surface proteins has been assembled. The library consists of prey and bait proteins. Preys are composed of the extracellular domain (ECD) of interest followed by a CD4 tag (rat Cd4d3+4) and a pentamerization domain derived from the rat Comp protein followed by β-lactamase. For the bait proteins the ECDs are fused to a CD4 tag and a biotinylation peptide. All proteins for the screen have been expressed by transient transfection of Human Embryonic Kidney (HEK293-6E) cells (Durocher et al., 2002) grown in Freestyle medium (Invitrogen) containing 1% FCS. Supernatants have been harvested 6 days post transfection. The bait proteins have been dialyzed against HBS (140 mM NaCl, 5 mM KCl, 2 mM $CaCl_2$), 1 mM MgCl2, 10 mM HEPES, pH 7.4) to remove free biotin. The proteins in the supernatants have been quantified and normalized.

For the AVEXIS screen the supernatant dilution factors have been adjusted to values allowing faithful detection of the interaction between Vasn (Slit-like2) and Islr2 (Söllner and Wright, 2009) with determined KD of 12 μM and a very short half-life (t1/2 0.16 s) (in preparation). The bait proteins have been immobilized on streptavidin coated 96 well microtiter plates (one bait/well) and incubated for 1 hour at room temperature. After 3 wash steps using HBS as wash buffer the baits have been probed by 50 μl of normalized prey proteins. After one-hour incubation the non-bound preys have been washed away by 2 washes with HBST (0.05% Tween) followed by two HBS washes. Then 50 μl of nitrocefin/well (0.1 mg/ml) has been added and incubated for 1 h at room temperature. Then the absorbance at 486 nm of each well has been measured using a μQuant spectrophotometer (BIO-TEK Instruments, INC). As a positive control for the prey proteins we used the Matn4 ECD as mono-biotinylated bait protein. Matn4 has been shown to bind to the coiled-coil pentamerization domain of Comp (Mann et al., 2004), which is present in all recombinant pentameric prey proteins of our AVEXIS library.

In the primary screen interactions were 'called' if the absorbance (at 486 nm) of a well after 1 h of incubation was ≥0.1 and 3 Sigma above the standard deviations of the mean of all wells. All interactions detected in the primary screen have been retested in a validation screen by using independently produced batches of proteins.

Domain Mapping Experiments

For the binding interface mapping experiments we used monomeric prey proteins. The concentration of the monomeric preys has been determined as described for the AVEXIS assay (β⎿lactamase enzymatic activity). After normalization, the monomeric preys have been screened against a set of proteins from the library to identify and remove promiscuous binders caused for example through improper domain boundary design. Both prey and bait orientations were tested in the domain mapping screen and two repeats for each orientation had been carried out.

Protein Purification

His-tagged full-length zebrafish Draxin protein (Draxin⎿CD4d3+4⎿6×His) has been expressed in HEK293-6E cells and affinitiy purified from tissue culture supernatants using HisTrap HP columns (GE healthcare). The correct size of the purified protein has been checked on a protein gel.

AVEXIS Based Competition Assay

The procedure of the competition assay is based on the AVEXIS assay. Netrin1 receptors were used as prey proteins together with 6×His⎿tagged purified Draxin (potential antagonist), and probed against Netrin1a bait proteins. The indicated concentrations of the potential inhibitors have been added together with prey proteins. For the competition tests with purified Draxin the concentration of the Netrin receptor prey proteins has been adjusted to an identical threshold binding concentration.

hFc Fusion Protein Normalization for the Competition Assay

We determined the concentration of ECD-hFc fusion proteins in tissue culture supernatants by ELISA, using the human IgG Fc fragment (Calbiochem) as a reference. Dilution series of the ECD-hFc containing supernatants have been incubated over night at 4° C. on 96 well Maxisorp plates (Nunc). After 3 PBS washes the plates were blocked with 0.5% BSA containing PBS (1 h). After additional 2 PBS washes and 1-hour incubation with an anti-human IgG (Fc specific) antibody fused to alkaline phosphatase (SIGMA) the plates have been washed 3 times with PBS. The detection has been carried out by addition of 50 μl/well of the AP substrate p-nitrophenylphosphate (SouthernBiotech). The substrate turnover has been determined by measuring the absorbance at 405 nm.

In Vivo Binding Assay

To reveal whether the interaction between Draxin and Netrin1a is detectable in vivo, an mRNA overexpression assay was designed to visualize the localization of the two proteins in zebrafish embryos. Constructs of full-length zebrafish Draxin and Netrin1a fused with fluorescent proteins were generated by using the Gateway® cloning system (Life Technologies).

Before used in the in vivo detection assay, the coding sequences of the generated fusion proteins were cloned into AVEXIS plasmids, expressed as preys and tested for activity against bait proteins of the corresponding binding partner. Following constructs were selected for the in vivo binding test: Draxin and Netrin1a C-terminally fused to superfolder-GFP (Draxin-sfGFP, Ntn1a-sfGFP) and Netrin1a C-terminally fused with mCherry (Ntn1a-mCherry). The corresponding capped mRNAs were synthesized using the mMESSAGE mMACHINE SP6 or T7 Transcription Kit (Ambion) according to manufacturer instructions. For the injections, zebrafish embryos were dechorionated using 1 mg/ml Pronase (Roche, 11459643001) and then injected with 1 nl mRNA into the cell center at one cell stage. Draxin-sfGFP or Netrin1a-sfGFP mRNAs were injected at 100 pg/embryo in combination with 10-15 pg/embryo of membrane-tagged RFP (mRFP) to label the cell membranes. The same amount of mRNA (100-200 pg/embryo) was injected in the Draxin-sgGFP and Netrin1a-mCherry coexpression experiments. The injected embryos have been cultured at 28.5° C. in agarose-coated dishes. At sphere stage (4 hpf), embryos were immobilized in 1% low-melting-point agarose in glass-bottom Petri dishes with the animal pole facing the coverslip. The imaging plane corresponded to a region approximately 15 μm beneath the enveloping layer of the embryos. Single plane confocal images of the embryos were taken using a Zeiss LSM 780 NLO microscope.

In Situ Detection of Draxin Binding Partners

A netrin binding fragment of Draxin (aa209-284) fused to the Fc region of human IgG ($Draxin_{aa209-284}$-hFc) has been expressed in HEK293-6E cells and used as an affinity probe to detect binding partners in zebrafish embryos. Draxin$_{aa209-284}$-hFc in situ staining has been done in whole mount wild type and netrin-1 knockdown zebrafish embryos. At 46 hpf wild type zebrafish embryos were dechorionated by for 2 hours at RT incubation in 0.1 mg/ml Pronase. At 48 hpf embryos were prefixed for 10 min at RT in 4% (w/v) paraformaldehyde (PFA) containing 1% Triton X-100 (v/v). After 3 washes (each 20 min) with PBS+1% Triton X-100 the embryos were blocked for 4 h at RT in PBS containing 0.2% BSA and 0.5% Triton X-100. Overnight incubation at 4° C. with HEK293-6E supernatant containing the Draxin-hFc fusion protein was followed by 3 short washes (10 min each) with PBST. Subsequently the embryos were post-fixed in 4% PFA (4 h at RT or overnight at 4° C.), rinsed shortly 3 times with PBST and incubated for 4 h at RT with an Alexa Fluor 568 goat anti human IgG antibody (Invitrogen, 1:250 dilution). After 3 washes (30 min each) in PBST the embryos were mounted in glycerol for visualization using a Zeiss LSM 510 microscope. A shorter version of Draxin containing the Netrin1a binding site had to be used because the full-length version of Draxin-hFc caused uniform background staining in zebrafish embryos probably by unspecific binding to glycosaminoglycans (GAGs) present on cell surfaces. A series of additional control ECD-hFc proteins have been tested, only Draxin$_{aa209-284}$-hFc displayed binding to the extracellular space of the floor plate.

Knockdown of netrin1a and netrin1b in Zebrafish Embryos

Morpholino antisense oligonucleotides (Gene-Tools) have been used to generate zebrafish with reduced netrin protein expression levels. The following morpholino sequences have been used to knockdown ntn1a ATGATGGACTTACCGACACATTCGT-3', SEQ ID NO.: 80) and ntn1b (5'-CGCACGTTACCAAAATCCTTATCAT-3', SEQ ID NO.: 81). In previous studies both morpholinos had been shown to efficiently knockdown the corresponding genes (Kastenhuber et aL, 2009; Suli et al.; 2006).

Surface Plasmon Resonance (SPR)

Surface Plasmon Resonance (SPR) experiments were performed on a Biacore 3000 (GE Healthcare) at 25° C. using a SA sensor chip in 0.01 M HEPES, pH 7.4, 0.15 M NaCl, 0.005% Surfactant P20 (HBS-P) running buffer at a flow rate of 30 µl/min. The instrument was used according to manufacturer's instructions.

Example 1: DraxinA Physically Interacts with Netrin1a

Using a protein-protein interaction screen assay, designed to identify direct interactions within a protein library consisting of secreted proteins and extracellular domains of cell surface proteins (Bushell et al., 2008), we carried out a large-scale screen involving more than 40,000 binding experiments. The library we used for the screen was strongly enriched for zebrafish proteins known to be expressed in the developing nervous system. During this screen we identified a novel interaction between two secreted proteins with known function in axon guidance, Netrin1a and DraxinA. In the primary screen a DraxinA prey protein has been tested for binding against a library consisting of 171 bait proteins, including a positive control. The DraxinA prey protein specifically bound to the Netrin1a bait (FIG. 1A) and did not bind to any additional proteins of the library. The interaction has been confirmed in both bait-prey orientations in a validation screen using new protein samples. Interestingly, both netrin1 and draxin are duplicated in zebrafish. In subsequent binding assays we were able to show that the Netrin1/Draxin interaction is also conserved for the paralogs Netrin1b and DraxinB (FIG. 1B).

The AVEXIS assay is able to detect very transient and weak interactions due to the avidity effect caused by the use of pentameric prey proteins. Hence, in order to test whether the interaction between Netrin1a and Draxin is transient or rather stable we used monomeric prey proteins and probed them against the corresponding binding partners. Using this approach, we confirmed the interaction between Netrin1a and Draxin suggesting that this interaction is based on strong binding between the two proteins.

Example 2: The Interaction Between Draxin and Netrin1 is Conserved for the Human Homologs Next we asked the question whether the interaction between Netrin1 and Draxin is conserved. By using the corresponding human homologs NTN1 and DRAXIN we were able to show that the interaction is indeed conserved. In addition, we observed that zebrafish Netrin1a was able to bind to human Draxin and vice versa (FIG. 2). This strongly indicates that this newly identified interaction is conserved within vertebrate species underscoring the biological relevance of this interaction.

Example 3: The Netrin1 Binding Region of Draxin has been Mapped Down to a 21Aa Motif Next, we narrowed down the region in DraxinA required for binding to Netrin1a. Zebrafish DraxinA consists of 360 amino acids (aa). The first 23 aa are part of the signal peptide. This sequence is followed by a poorly conserved N-terminal half of the protein (FIG. 3). In contrast, the C-terminal half of the protein is highly conserved and ends with a 10 cysteine-containing domain (aa285-aa360). In terms of cyteine spacing this domain is similar to domains present in the Wnt antagonist Dkk1 (Glinka et al., 1998).

To map down the Netrin1a binding region in DraxinA we generated a series of DraxinA truncations and deletions and tested them for binding against Netrin1a (FIG. 4). Using this approach we were able to narrow down the binding region to a 21aa DraxinA protein fragment. In addition, a full-length version of DraxinA lacking these 21aa completely lost the ability to bind to Netrin1a. Additional removal of 5aa from the N-terminal or C-terminal end of the 21aa stretch caused a dramatic reduction of the binding ability to Netrin1a. Interestingly, the Netrin-binding 21aa stretch (aa232-252) of DraxinA is highly conserved cross vertebrate species (FIG. 5). It is noteworthy that, this conserved 21aa region is also highly specific for Draxin and cannot be found in other proteins.

Example 4: Netrin1a Domain Mapping

Netrin1a is a multi-domain containing protein composed of 603 amino acids. It consists of a laminin N-terminal domain (LamNT) encoded by amino acid 44-282 followed by 3 laminin-type epidermal growth factor-like domains (aa284-450), and a C-terminal domain (C345C) encoded by amino acid 486 to 594. In order to map the DraxinA binding region in Netrin1a we generated a set of truncated Netrin1a fragments and probed them in the AVEXIS assay for binding against DraxinA. Using this approach we were able to narrow down the binding region to a fragment consisting of amino acid 401-458 (FIG. 4B). This fragment encodes the third laminin-type EGF domain. The third EGF-domain of Netrin1a is highly conserved in vertebrate Netrin1 homologs. For example, only a single amino acid exchange is present in this domain between zebrafish Netrin1a (CDCHPVGAAGKTCNQTTGQCPCKDGV TGITCNRCANGYQQSRSPIAPC; SEQ ID NO: 64) and human Netrin1 (CDCHPVGAAGKTCNQTTGQCPCKDGVTGITCNRCAKGYQQSRSPIAPC; SEQ ID NO: 65) proteins, Interestingly, the third EGF domain of Netrin1 has recently been shown to be required for Netrin receptor binding (Finci et al., 2014; Xu et al., 2014). These findings offer a mechanistic explanation for our observed competition assay results.

Example 5: DraxinA is Able to Inhibit the Binding of Netrin1a to Netrin Receptors By using an AVEXIS-based competition assay (FIG. 6 A) we tested whether the binding of DraxinA to Netrin1a has an influence on Netrins ability to bind to Netrin receptors. First we confirmed that we reliably detected the binding of Netrin1a to Netrin receptors of the DCC/Neo1 and Unc5 families with the AVEXIS method. We also tested whether Draxin is able to bind to the corresponding Netrin receptors. Contrary to previous findings (Ahmed et al., 2011), we were not able to detect direct binding between Draxin and any of the tested Netrin receptors using the AVEXIS platform. This has also been confirmed by a recent publication (Haddick et al. 2014). In the competition assay the extracellular domains (ECDs) of Netrin receptors have been used as prey proteins together with purified full length DraxinA and probed for binding against Netrin1a bait proteins. Using this strategy, we observed a DraxinA concentration dependent inhibition of the binding between Netrin1a and Netrin receptors (FIG. 6B,C,D). The inhibition is specific for DraxinA. Furthermore, DraxinA (FIG. 6 E) is not able to block the binding of RGMc to Neo1, another reported ligand of the corresponding receptor (Bell et al., 2013).

Example 6: The 21Aa DraxinA Fragment Fused to the Human Fc Region of IgG is Sufficient to Block the Binding of Netrin1a to Netrin Receptors Next we assayed whether the 21aa DraxinA fragment fused to the human Fc tag (Draxin$_{aa232-252}$-hFc) is sufficient to outcompete Netrin/Netrin receptor interactions.

We compared the effect of Draxin$_{aa232-252}$-hFc with full-length Draxin-hFc and a version of DraxinA where the 21aa Netrin1 binding motif has been deleted (DraxinAΔ$_{aa231-252}$-hFc) in the competition assay for their ability to interfere with the binding of Netrin1a to Dcc. The results show that Draxin$_{aa232-252}$-hFc has a similar efficiency in inhibiting the binding of Netrin1a to Dcc as the DraxinA full-length version (Draxin-hFc). The DraxinA version with the 21 aa deletion (DraxinAΔ$_{aa231-252}$-hFc) is not able to compete for binding to Netrin1a (FIG. 7). In addition we used our set of different Draxin-hFc proteins to test whether they have an effect on other known interactions (Cntn1a/Ptprz1b, Vasn/Islr2, EphB4a/EphrinB2a). None of the 3 Draxin-hFc versions was able to inhibit any of the tested interactions (FIG. 7 B,C,D).

Taken together, our results show that the 21aa region is necessary for the competition and that the Draxin$_{aa232-252}$-hFc fusion protein is also sufficient to outcompete Netrin receptors for Netrin1a binding.

Example 7: The Binding of the 21Aa DraxinA Fragment to Netrin1a is Highly Specific In order to determine the binding specificity of the 21aa DraxinA peptide we used the AVEXIS assay and screened the 21aa fragment as bait and prey against proteins from our library. In this screen against a set of 141 bait proteins the DraxinA$_{aa232-252}$-prey only bound to the Ntn1a-bait and to the positive control bait Matn4 (FIG. 8A). Similar results we obtained for the DraxinA$_{aa232-252}$-bait protein, which only interacted with the Ntn1a-prey in a screen against a set of 191 different prey proteins (FIG. 8B). These findings indicate that the binding of this short 21 aa peptide to Netrin1a is highly specific.

Example 8: DraxinA Outcompetes Receptor Bound Netrin 1a

Netrin1 binds with high affinity ($K_d$'s in the low nM range) to its receptors of the DCC- and Unc5-family (Leonardo et al., 1997). Hence, we asked the question whether already bound Netrin1a could be displaced from the receptors by DraxinA. In order to do so we carried out an AVEXIS based competition assay and tested three different settings (FIG. 9A). In one experimental setting Netrin1a-baits were preincubated with purified DraxinA before addition of the DCC prey. In the second set of experiments the Netrin1a-baits were incubated with a mixture of DraxinA and DCC prey proteins, and in the third set of experiments Netrin1a-baits have been preincubated with DCC preys followed by the addition of purified DraxinA as inhibitor. We did not observe a difference in the %-binding response between these 3 sets of experiments. These findings show that already formed DCC/Netrin1a complexes can be disrupted by the addition of DraxinA. These findings indicate that DraxinA has a higher affinity for Netrin1a than the Netrin receptor DCC.

Example 9: In Vivo Detection of the Draxin-Netrin Interaction in Zebrafish Embryos To independently confirm the Draxin/Netrin1a interaction and to test whether both proteins are able to interact in vivo, we made use of transient protein overexpression experiments in zebrafish embryos. mRNAs encoding Draxin fused to superfolder GFP (Draxin-sfGFP) and Netrin1a tagged with mCherry (Netrin1a-mCherry) or superfolder GFP (Netrin1a-sfGFP) have been injected into one-cell stage zebrafish embryos. The distribution of the corresponding fluorophore tagged proteins has been analyzed in sphere stage zebrafish embryos (4 hours post fertilization) (FIG. 11A). At this developmental stage the extracellular space width between the cells is very large, ideally suited to visualize the localization of secreted proteins. Upon injection of mRNA encoding Draxin-sfGFP we observed an evenly distributed signal outside the cells in the extracellular milieu of 4 hpf zebrafish embryos (FIG. 11 Ba). In contrast thereto, the distribution of Netrin1a-sfGFP was restricted to cell surface sub-domains (FIG. 11 Bb).

When Draxin-sfGFP was coexpressed with Netrin1a-mCherry, Draxin-sfGFP re-located to Netrin1a-mCherry positive membrane associated densities (FIG. 11 Bc). This indicated that localized Netrin1a-mCherry was able to capture diffusible Draxin-sfGFP.

The mRNA overexpression experiments showed that Draxin and Netrin1a are able to interact with each other in vivo. To further support this we used another strategy aiming to detect the distribution of endogenous Draxin interaction partners at developmental stages relevant for axon guidance decisions. From our binding assay with monomeric prey proteins we already had hints that the interaction between Draxin and Netrin is of high-affinity. Thus, we fused a netrin-binding fragment of the Draxin-E CD (aa209-284) to the human Fc region to generate an affinity probe. First, we tested this probe on zebrafish embryos from different developmental stages. After very gentle fixation the embryos were incubated with HEK293-6E cell supernatants containing the recombinant soluble $Draxin_{aa209-284}$-hFc protein.

Using an Alexa-Fluor 568 anti human IgG antibody to detect in situ bound $Draxin_{aa209-284}$-hFc we only detect a signal in close proximity to the floor plate (FIG. 12A, 12Ba). Because floor plate cells express Netrin1a and Netrin1b, we had indications that the signal detected by using the Draxin affinity probe indeed corresponds to in the extracellular space localized netrin. To prove this observation, we compared 48 hpf wt embryos with netrinla and netrinlb double-knockdown embryos (FIG. 12Ba, 12Bb). In double-knockdown embryos the signal from the bound affinity probe was barely detectable compared to non-injected siblings, indicating that the $Draxin_{aa209-284}$-hFc probe indeed detected netrin. Taken together, the results from our mRNA overexpression and Draxin affinity probe experiments provide strong evidence that Draxin and Ntn1a are able to interact in vivo in zebrafish embryos.

Example 10: Human DRAXIN/Netrin-Signaling Network

To determine the binding specificity of DRAXIN/Netrin interactions, we carried out a pairwise binding screen between human DRAXIN and human Netrin family members. Except Netrin-5, we included all human Netrin family members consisting of two secreted γ-Netrins (Netrin-1 and Netrin-3) and one secreted (Netrin-4) and two GPI-linked β-Netrins (Netrin-G1 and Netrin-G2) in our binding study. Human DRAXIN and a 21 amino acid Netrin binding fragment derived thereof (SEQ ID NO.: 1) bound to Netrin-1 and Netrin-3 but not to human β-Netrin family members (FIG. 13).

These experiments confirm for human proteins the Draxin/γ-Netrin binding specificity within the Netrin family and showed that the human 21 amino acid DRAXIN fragment (SEQ ID NO.: 1), like its zebrafish counterpart (SEQ ID NOs.: 3), is sufficient for binding.

Example 11: Validation of the Draxin/Netrin1 Interaction by Surface Plasmon Resonance Recombinant human Draxin was purchased from R&D systems. Biotinylated recombinant human UNC5B, Netrin1 and DCC were produced recombinantly using the described mammalian expression system (HEK293-6E). Biotinylated proteins were immobilised on the SA coated sensor chip and Draxin was injected sequentially in increasing concentrations (0 nM, 1.2 nM. 2.3 nM, 4.7 nM, 9.4 nM, 18.8 nM) for 3 min. Dissociation was allowed for 5 min in HBS-P. Binding was monitored and an interaction of Draxin to immobilised Netrin-1 was observed with a binding constant KO of approximately 20 to 100 nM. No binding of Draxin to UNC5B and DCC was detected (FIG. 14).

REFERENCES

Ahmed G, Shinmyo Y, Ohta K, Islam S M, Hossain M, Naser I B, Riyadh M A, Su Y, Zhang S, Tessier-Lavigne M, Tanaka H: Draxin inhibits axonal outgrowth through the netrin receptor DCC. J Neurosci. 2011 Sep. 28; 31(39):14018-23.

Arakawa H: Netrin-1 and its receptors in tumorigenesis. Nat Rev Cancer. 2004 December; 4(12):978-87.

Bell C H, Healey E, van Erp S, Bishop B, Tang C, Gilbert R J, Aricescu A R, Pasterkamp R J, Siebold C: Structure of the repulsive guidance molecule (RGM)-neogenin signaling hub. Science. 2013 Jul. 5; 341(6141):77-80.

Bushell K M, Söllner C, Schuster-Boeckler B, Bateman A, Wright G J: Large-scale screening for novel low-affinity extracellular protein interactions. Genome Res. 2008 April; 18(4):622-30.

Castets M, Broutier L, Molin Y, Brevet M, Chazot G, Gadot N, Paquet A, Mazelin L, Jarrosson-Wuilleme L, Scoazec J Y, Bernet A, Mehlen P: DCC constrains tumour progression via its dependence receptor activity. Nature. 2012; 482(7386):534-7.

Delloye-Bourgeois C, Brambilla E, Coissieux M M, Guenebeaud C, Pedeux R, Firlej V, Cabon F, Brambilla C, Mehlen P, Bernet A: Interference with netrin-1 and tumor cell death in non-small cell lung cancer. J Natl Cancer Inst. 2009 Feb. 18; 101(4):237-47.

Durocher Y, Perret S, Kamen A: High-level and high-throughput recombinant protein production by transient transfection of suspension-growing human 293-EBNA1 cells. Nucleic Acids Res. 2002 Jan. 15; 30(2):E9.

Finci L I, Kruger N, Sun X, Zhang J, Chegkazi M, Wu Y, Schenk G, Mertens H D, Svergun D I, Zhang Y, et al.: The Crystal Structure of Netrin-1 in Complex with DCC Reveals the Bifunctionality of Netrin-1 As a Guidance Cue. Neuron 2014; 83(4):839-849.

Fitamant J, Guenebeaud C, Coissieux M M, Guix C, Treilleux I, Scoazec J Y, Bachelot T, Bernet A, Mehlen P: Netrin-1 expression confers a selective advantage for tumor cell survival in metastatic breast cancer. Proc Natl Acad Sci USA. 2008 Mar. 25; 105(12):4850-5.

Glinka A, Wu W, Delius H, Monaghan A P, Blumenstock C, Niehrs C: Dickkopf-1 is a member of a new family of secreted proteins and functions in head induction. Nature. 1998 Jan. 22; 391(6665):357-62.

Islam S M, Shinmyo Y, Okafuji T, Su Y, Naser I B, Ahmed G, Zhang S, Chen S, Ohta K, Kiyonari H, Abe T, Tanaka S, Nishinakamura R, Terashima T, Kitamura T, Tanaka H: Draxin, a repulsive guidance protein for spinal cord and forebrain commissures. Science. 2009 Jan. 16; 323(5912):388-93.

Haddick P C, Tom I, Luis E, Quinones G, Wranik B J, Ramani S R, Stephan J P, Tessier-Lavigne M, Gonzalez L C: Defining the Ligand Specificity of the Deleted in Colorectal Cancer (DCC) Receptor. PLoS One. 2014 Jan. 6; 9(1):e84823.

Kastenhuber E, Kern U, Bonkowsky J L, Chien C B, Driever W, and Schweitzer J: Netrin-DCC, Robo-Slit, and heparan sulfate proteoglycans coordinate lateral positioning of longitudinal dopaminergic diencephalospinal axons. J Neurosci 2009; 29:8914-8926.

Kwan K M, Fujimoto E, Grabher C, Mangum B D, Hardy M E, Campbell D S, Parant J M, Yost H J, Kanki J P, and Chien C B: The Tol2kit: a multisite gateway-based construction kit for Tol2 transposon transgenesis constructs. Dev Dyn 2007; 236:3088-3099.

Leonardo E D, Hinck L, Masu M, Keino-Masu K, Ackerman S L, Tessier-Lavigne M: Vertebrate homologues of *C. elegans* UNC-5 are candidate netrin receptors. Nature. 1997 Apr. 24; 386(6627):833-8.

Mann H H, Ozbek S, Engel J, Paulsson M, Wagener R:Interactions between the cartilage oligomeric matrix protein and matrilins. Implications for matrix assembly and the pathogenesis of chondrodysplasias. J Biol Chem. 2004 Jun. 11; 279(24):25294-8.

Mehlen P, Delloye-Bourgeois C, Chédotal A: Novel roles for Slits and netrins: axon guidance cues as anticancer targets? Nat Rev Cancer. 2011 March; 11(3):188-97.

Moore S W, Tessier-Lavigne M, Kennedy T E: Netrins and their receptors. Adv Exp Med Biol. 2007; 621:17-31.

Paradisi A, Creveaux M, Gibert B, Devailly G, Redoulez E, Neves D, Cleyssac E, Treilleux I, Klein C, Niederfellner G, Cassier P A, Bernet A, Mehlen P: Combining chemotherapeutic agents and netrin-1 interference potentiates cancer cell death. EMBO Mol Med. 2013 December; 5(12):1821-34.

Paradisi A, Maisse C, Coissieux M M, Gadot N, Lépinasse F, Delloye-Bourgeois C, Delcros J G, Svrcek M, Neufert C, Fléjou J F, Scoazec J Y, Mehlen P: Netrin-1 up-regulation in inflammatory bowel diseases is required for colorectal cancer progression. Proc Natl Acad Sci USA. 2009 Oct. 6; 106(40):17146-51

Söllner C, Wright G J: A cell surface interaction network of neural leucine-rich repeat receptors. Genome Biol. 2009; 10(9):R99.

Suli A, Mortimer N, Shepherd I, and Chien C B: Netrin/DCC signaling controls contralateral dendrites of octavolateralis efferent neurons. J Neurosci 2006; 26:13328-13337.

Xu K, Wu Z, Renier N, Antipenko A, Tzvetkova-Robev D, Xu Y, Minchenko M, Nardi-Dei V, Rajashankar K R, Himanen J, et al.: Neural migration. Structures of netrin-1 bound to two receptors provide insight into its axon guidance mechanism. Science 2014; 344: 1275-1279.

The invention claimed is:

1. Draxin-binding peptide comprising (i) at least 20 consecutive amino acids from the sequence KACD-CHPVGAAGKTCNQTTGQCPCKDGVTGITCNR-CANGYQQSRSP IAPCIKIPIAPP (SEQ ID NO.: 51) or (ii) a variant thereof having a sequence identity of at least 90%, or at least 95% to SEQ ID NO.: 51; wherein said peptide has a length of up to about 200 amino acids and is fused to a heterologous peptide or polypeptide.

2. The peptide according to claim 1, wherein said peptide comprises a sequence selected from the group consisting of SEQ ID NO.: 45, SEQ ID NO.: 48, SEQ ID NO.: 65 and SEQ ID NO.: 77, or a variant thereof having a sequence identity of at least 90%, or at least 95% thereto.

3. The peptide according to claim 1, in combination with a carrier suitable for use in medicine.

4. The peptide according to claim 1, wherein said variant contains at least one non-naturally occurring substitution modification relative to SEQ ID NO.:51.

5. The peptide according to claim 1, wherein said peptide is fused to a functional fragment of an immunoglobulin (Ig).

6. The peptide according to claim 5, wherein said functional fragment of an immunoglobulin (Ig) is an Ig Fc fragment.

7. The peptide according to claim 6, wherein said Ig Fc fragment is a human Ig Fc fragment.

8. The peptide according to claim 7, wherein said human Ig Fc fragment is a human IgG Fc fragment.

* * * * *

SEQUENCE LISTING

```
<160> NUMBER OF SEQ ID NOS: 82

<210> SEQ ID NO 1
<211> LENGTH: 21
<212> TYPE: PRT
<213> ORGANISM: Homo sapiens

<400> SEQUENCE: 1

Glu Val Met Pro Thr Leu Asp Met Ala Leu Phe Asp Trp Thr Asp Tyr
1               5                   10                  15

Glu Asp Leu Lys Pro
            20


<210> SEQ ID NO 2
<211> LENGTH: 21
<212> TYPE: PRT
<213> ORGANISM: Danio rerio

<400> SEQUENCE: 2

Asp Val Ala Pro Thr Phe Asn Met Ala Leu Phe Asp Trp Thr Asp Tyr
1               5                   10                  15

Glu Asp Met Arg Pro
            20


<210> SEQ ID NO 3
<211> LENGTH: 21
<212> TYPE: PRT
<213> ORGANISM: Danio rerio

<400> SEQUENCE: 3

Glu Val Met Pro Thr Leu Asp Met Thr Leu Phe Asp Trp Thr Asp Tyr
1               5                   10                  15

Glu Asp Met Lys Pro
            20


<210> SEQ ID NO 4
<211> LENGTH: 349
<212> TYPE: PRT
<213> ORGANISM: Homo sapiens

<400> SEQUENCE: 4

Met Ala Gly Pro Ala Ile His Thr Ala Pro Met Leu Phe Leu Val Leu
1               5                   10                  15

Leu Leu Pro Leu Glu Leu Ser Leu Ala Gly Ala Leu Ala Pro Gly Thr
            20                  25                  30
```

```
Pro Ala Arg Asn Leu Pro Glu Asn His Ile Asp Leu Pro Gly Pro Ala
        35                  40                  45

Leu Trp Thr Pro Gln Ala Ser His His Arg Arg Arg Gly Pro Gly Lys
    50                  55                  60

Lys Glu Trp Gly Pro Gly Leu Pro Ser Gln Ala Gln Asp Gly Ala Val
65                  70                  75                  80

Val Thr Ala Thr Arg Gln Ala Ser Arg Leu Pro Glu Ala Glu Gly Leu
                85                  90                  95

Leu Pro Glu Gln Ser Pro Ala Gly Leu Leu Gln Asp Lys Asp Leu Leu
            100                 105                 110

Leu Gly Leu Ala Leu Pro Tyr Pro Glu Lys Glu Asn Arg Pro Pro Gly
        115                 120                 125

Trp Glu Arg Thr Arg Lys Arg Ser Arg Glu His Lys Arg Arg Arg Asp
    130                 135                 140

Arg Leu Arg Leu His Gln Gly Arg Ala Leu Val Arg Gly Pro Ser Ser
145                 150                 155                 160

Leu Met Lys Lys Ala Glu Leu Ser Glu Ala Gln Val Leu Asp Ala Ala
                165                 170                 175

Met Glu Glu Ser Ser Thr Ser Leu Ala Pro Thr Met Phe Phe Leu Thr
            180                 185                 190

Thr Phe Glu Ala Ala Pro Ala Thr Glu Glu Ser Leu Ile Leu Pro Val
        195                 200                 205

Thr Ser Leu Arg Pro Gln Gln Ala Gln Pro Arg Ser Asp Gly Glu Val
    210                 215                 220

Met Pro Thr Leu Asp Met Ala Leu Phe Asp Trp Thr Asp Tyr Glu Asp
225                 230                 235                 240

Leu Lys Pro Asp Gly Trp Pro Ser Ala Lys Lys Lys Glu Lys His Arg
                245                 250                 255

Gly Lys Leu Ser Ser Asp Gly Asn Glu Thr Ser Pro Ala Glu Gly Glu
            260                 265                 270

Pro Cys Asp His His Gln Asp Cys Leu Pro Gly Thr Cys Cys Asp Leu
        275                 280                 285

Arg Glu His Leu Cys Thr Pro His Asn Arg Gly Leu Asn Asn Lys Cys
    290                 295                 300

Phe Asp Asp Cys Met Cys Val Glu Gly Leu Arg Cys Tyr Ala Lys Phe
305                 310                 315                 320

His Arg Asn Arg Arg Val Thr Arg Arg Lys Gly Arg Cys Val Glu Pro
                325                 330                 335

Glu Thr Ala Asn Gly Asp Gln Gly Ser Phe Ile Asn Val
            340                 345


<210> SEQ ID NO 5
<211> LENGTH: 360
<212> TYPE: PRT
<213> ORGANISM: Danio rerio

<400> SEQUENCE: 5

Met Val Ala Pro Gly Leu Cys Gln Leu Phe Ile Leu Leu Leu Ile Thr
1               5                   10                  15

Leu Ser His Thr Leu His Ser Ser Glu Ile Ser Ser Asp Asn Phe Lys
            20                  25                  30

Gln Ser Leu Thr Pro Ser Thr Thr Thr Ser Lys Glu His Pro Glu Thr
        35                  40                  45

Gly Leu Thr Gly Gly Arg Gln Gln Lys Arg His Trp Ser Gly Lys Glu
```

```
    50                  55                  60

Arg Asp Ser Ala Gly Leu Phe Ser Gln Arg His Met Asp Arg Leu Glu
65                  70                  75                  80

Asp Asp Gly Thr Ser Met Glu Gly Leu Ser Pro Val Arg Leu Glu Met
                85                  90                  95

Gly Pro Gly Asp Thr Met Lys Ala Glu Val His Gly Glu Val Arg Ala
            100                 105                 110

Ser Ala Gln Met Arg Gln Gly Ser His Pro Ala Glu Gly Glu Leu Asn
        115                 120                 125

Arg Lys Gly Arg Arg His Ser His Arg Leu Leu Ala Glu His Arg Lys
    130                 135                 140

His Gly Gly Lys Lys Asp Lys Gly Arg Gly Lys Gly Asp Leu Ser Asp
145                 150                 155                 160

Pro Glu Pro Glu Leu Asp Ser Leu Leu Lys Asp Leu Asn Ala Phe Glu
                165                 170                 175

Asp Gly Leu Asn Thr Ser Pro Pro Asn Tyr Asn Ser Val Pro Leu Asn
            180                 185                 190

Glu Val Pro Ser Pro Leu Ser Pro Ile Leu Val Thr Thr Ala Ile Lys
        195                 200                 205

Gly His Pro Pro Thr Leu Pro Pro Ala Ser Thr Lys Pro Gln Lys Ser
    210                 215                 220

Ser Gln Gly Arg Thr Gln Gly Glu Val Met Pro Thr Leu Asp Met Thr
225                 230                 235                 240

Leu Phe Asp Trp Thr Asp Tyr Glu Asp Met Lys Pro Ala Asp Ser Trp
                245                 250                 255

Pro Ser Asn Lys Arg Lys Asp Lys Arg Arg Ser Lys Asn Lys Ser Asn
            260                 265                 270

Gly Asn Thr Thr Thr Glu Ala Gly Ile Val Glu Pro Cys Asp His His
        275                 280                 285

Leu Asp Cys Leu Ser Gly Ser Cys Cys Asp Leu Arg Glu Phe Glu Cys
    290                 295                 300

Lys Pro His Asn Arg Gly Leu Asn Asn Lys Cys Phe Asp Asp Cys Met
305                 310                 315                 320

Cys Glu Glu Gly Leu Arg Cys Tyr Ala Lys Phe His Arg Lys Arg Arg
                325                 330                 335

Val Thr Arg Arg Arg Gly Arg Cys Val Asp Pro Glu Ser Val Asn Ser
            340                 345                 350

Asn Gln Gly Ala Phe Ile Thr Val
        355                 360


<210> SEQ ID NO 6
<211> LENGTH: 351
<212> TYPE: PRT
<213> ORGANISM: Danio rerio

<400> SEQUENCE: 6

Met Ala Val Ser Cys Trp Tyr Phe Ala Leu Phe Leu Ile Phe Asp Leu
1               5                   10                  15

Met Thr Met Thr Leu Gly Thr Asn Thr His His Asn Ser Pro Met Glu
            20                  25                  30

Val Phe Ser Glu Asn Ile Ile Ile Pro Pro Lys Pro Glu Ala Ser Ile
        35                  40                  45

His His His Thr His Gln Arg Thr Asp Arg Gly Arg Lys Glu Arg Met
    50                  55                  60
```

-continued

```
Thr Ala Ser Gln Leu Arg Glu Arg Pro Arg Ile Ala Ile Phe His Thr
65                  70                  75                  80

Gln Asn Glu Gly Pro Asp Leu Glu Gly Leu Ser Pro Val Arg Leu Glu
                85                  90                  95

Met Glu Pro Ala Asp Lys Arg Arg Val Met Thr Pro Arg Lys Lys Thr
            100                 105                 110

Phe Met Gly Ser Asp Ser Leu Ile Gln Glu Lys Met Asn Ile Ser Pro
        115                 120                 125

Gly Ala Glu Thr Pro Glu Lys Ala Met Arg Arg Pro Thr Val Arg Lys
    130                 135                 140

Val Phe Gly Gly His Ile Thr Arg Ala Pro His Glu Glu Glu Ser Leu
145                 150                 155                 160

Ala Ser Gly Lys Lys Arg Arg Val Ser Phe Asp Gln Arg Leu Asn Lys
                165                 170                 175

Ala Ser Phe Gly Ser Pro Thr Glu Pro Val Leu Pro Ala Ala Thr Val
            180                 185                 190

Gly Thr Phe Ile Leu Pro Ile Thr Ala Ala Val Asp Gly Asn Pro Asn
        195                 200                 205

Pro Ser Ser Glu Pro Gln Val Arg Arg Tyr Leu Gly Gly Asp Val Ala
    210                 215                 220

Pro Thr Phe Asn Met Ala Leu Phe Asp Trp Thr Asp Tyr Glu Asp Met
225                 230                 235                 240

Arg Pro Gly Asp Lys Lys Gln Tyr Ser Lys Lys Gln Gly Ser Glu Lys
                245                 250                 255

Gln Ala Thr Gln Ser Pro Ser Thr Gly Leu Val Arg Leu Thr Ser Glu
            260                 265                 270

Asn Asn Val Cys Lys His His Leu Asp Cys Leu Pro Gly Ser Cys Cys
        275                 280                 285

Asn Leu Arg Lys His Val Cys Glu Leu His Asn Arg Gly Phe Asn Asn
    290                 295                 300

Lys Cys Tyr Asp Ser Cys Met Cys Glu Glu Gly Leu Arg Cys Tyr Ala
305                 310                 315                 320

Lys Ser His Arg His Tyr Arg Ile Thr Arg Lys Lys Gly Gln Cys Val
                325                 330                 335

Asp Pro Glu Asp Leu Asn His Ala Val Ser Arg Trp Met Gln Met
            340                 345                 350
```

<210> SEQ ID NO 7
<211> LENGTH: 75
<212> TYPE: PRT
<213> ORGANISM: Danio rerio

<400> SEQUENCE: 7

```
His Pro Pro Thr Leu Pro Pro Ala Ser Thr Lys Pro Gln Lys Ser Ser
1               5                   10                  15

Gln Gly Arg Thr Gln Gly Glu Val Met Pro Thr Leu Asp Met Thr Leu
            20                  25                  30

Phe Asp Trp Thr Asp Tyr Glu Asp Met Lys Pro Ala Asp Ser Trp Pro
        35                  40                  45

Ser Asn Lys Arg Lys Asp Lys Arg Arg Ser Lys Asn Lys Ser Asn Gly
    50                  55                  60

Asn Thr Thr Thr Glu Ala Gly Ile Val Glu Pro
65                  70                  75
```

<210> SEQ ID NO 8

<211> LENGTH: 66
<212> TYPE: PRT
<213> ORGANISM: Danio rerio

<400> SEQUENCE: 8

His Pro Pro Thr Leu Pro Pro Ala Ser Thr Lys Pro Gln Lys Ser Ser
1               5                   10                  15

Gln Gly Arg Thr Gln Gly Glu Val Met Pro Thr Leu Asp Met Thr Leu
            20                  25                  30

Phe Asp Trp Thr Asp Tyr Glu Asp Met Lys Pro Ala Asp Ser Trp Pro
        35                  40                  45

Ser Asn Lys Arg Lys Asp Lys Arg Arg Ser Lys Asn Lys Ser Asn Gly
    50                  55                  60

Asn Thr
65

<210> SEQ ID NO 9
<211> LENGTH: 48
<212> TYPE: PRT
<213> ORGANISM: Danio rerio

<400> SEQUENCE: 9

His Pro Pro Thr Leu Pro Pro Ala Ser Thr Lys Pro Gln Lys Ser Ser
1               5                   10                  15

Gln Gly Arg Thr Gln Gly Glu Val Met Pro Thr Leu Asp Met Thr Leu
            20                  25                  30

Phe Asp Trp Thr Asp Tyr Glu Asp Met Lys Pro Ala Asp Ser Trp Pro
        35                  40                  45

<210> SEQ ID NO 10
<211> LENGTH: 43
<212> TYPE: PRT
<213> ORGANISM: Danio rerio

<400> SEQUENCE: 10

His Pro Pro Thr Leu Pro Pro Ala Ser Thr Lys Pro Gln Lys Ser Ser
1               5                   10                  15

Gln Gly Arg Thr Gln Gly Glu Val Met Pro Thr Leu Asp Met Thr Leu
            20                  25                  30

Phe Asp Trp Thr Asp Tyr Glu Asp Met Lys Pro
        35                  40

<210> SEQ ID NO 11
<211> LENGTH: 50
<212> TYPE: PRT
<213> ORGANISM: Danio rerio

<400> SEQUENCE: 11

Gln Gly Arg Thr Gln Gly Glu Val Met Pro Thr Leu Asp Met Thr Leu
1               5                   10                  15

Phe Asp Trp Thr Asp Tyr Glu Asp Met Lys Pro Ala Asp Ser Trp Pro
            20                  25                  30

Ser Asn Lys Arg Lys Asp Lys Arg Arg Ser Lys Asn Lys Ser Asn Gly
        35                  40                  45

Asn Thr
    50

<210> SEQ ID NO 12
<211> LENGTH: 32
<212> TYPE: PRT

<213> ORGANISM: Danio rerio

<400> SEQUENCE: 12

Gln Gly Arg Thr Gln Gly Glu Val Met Pro Thr Leu Asp Met Thr Leu
1               5                   10                  15

Phe Asp Trp Thr Asp Tyr Glu Asp Met Lys Pro Ala Asp Ser Trp Pro
            20                  25                  30

<210> SEQ ID NO 13
<211> LENGTH: 27
<212> TYPE: PRT
<213> ORGANISM: Danio rerio

<400> SEQUENCE: 13

Gln Gly Arg Thr Gln Gly Glu Val Met Pro Thr Leu Asp Met Thr Leu
1               5                   10                  15

Phe Asp Trp Thr Asp Tyr Glu Asp Met Lys Pro
            20                  25

<210> SEQ ID NO 14
<211> LENGTH: 22
<212> TYPE: PRT
<213> ORGANISM: Danio rerio

<400> SEQUENCE: 14

Gly Glu Val Met Pro Thr Leu Asp Met Thr Leu Phe Asp Trp Thr Asp
1               5                   10                  15

Tyr Glu Asp Met Lys Pro
            20

<210> SEQ ID NO 15
<211> LENGTH: 21
<212> TYPE: PRT
<213> ORGANISM: Danio rerio

<400> SEQUENCE: 15

Glu Val Met Pro Thr Leu Asp Met Thr Leu Phe Asp Trp Thr Asp Tyr
1               5                   10                  15

Glu Asp Met Lys Pro
            20

<210> SEQ ID NO 16
<211> LENGTH: 22
<212> TYPE: PRT
<213> ORGANISM: Homo sapiens

<400> SEQUENCE: 16

Gly Glu Val Met Pro Thr Leu Asp Met Ala Leu Phe Asp Trp Thr Asp
1               5                   10                  15

Tyr Glu Asp Leu Lys Pro
            20

<210> SEQ ID NO 17
<211> LENGTH: 22
<212> TYPE: PRT
<213> ORGANISM: Danio rerio

<400> SEQUENCE: 17

Gly Asp Val Ala Pro Thr Phe Asn Met Ala Leu Phe Asp Trp Thr Asp
1               5                   10                  15

Tyr Glu Asp Met Arg Pro
            20

<210> SEQ ID NO 18
<211> LENGTH: 1047
<212> TYPE: DNA
<213> ORGANISM: Homo sapiens

<400> SEQUENCE: 18
atggctgggc ctgccatcca caccgctccc atgctgttcc tcgtcctcct gctgcccctg 60
gagctgagcc tggcaggcgc ccttgcacct gggacccctg cccggaacct ccctgagaat 120
cacattgacc tcccaggccc agcgctgtgg acgcctcagg ccagccacca ccgccggcgg 180
ggcccgggca agaaggagtg ggcccaggc ctgcccagcc aggcccagga tggggctgtg 240
gtcaccgcca ccaggcaggc ctccaggctg ccagaggctg aggggctgct gcctgagcag 300
agtcctgcag gcctgctgca ggacaaggac ctgctcctgg gactggcatt gccctacccc 360
gagaaggaga accgacctcc aggttgggag aggaccagga aacgcagcag ggagcacaag 420
agacgcaggg acaggttgag gctgcaccaa ggccgagcct tggtccgagg tcccagctcc 480
ctgatgaaga aggcagagct ctccgaagcc caggtgctgg atgcagccat ggaggaatcc 540
tccaccagcc tggcgcccac catgttcttt ctcaccacct ttgaggcagc acctgccaca 600
gaagagtccc tgatcctgcc cgtcacctcc ctgcggcccc agcaggcaca gcccaggtct 660
gacggggagg tgatgcccac gctggacatg gccttgttcg actggaccga ttatgaagac 720
ttaaaacctg atggttggcc ctctgcaaag aagaaagaga aacaccgcgg taaactctcc 780
agtgatggta acgaaacatc accagccgaa ggggaaccat gcgaccatca ccaagactgc 840
ctgccaggga cttgctgcga cctgcgggag catctctgca caccccacaa ccgaggcctc 900
aacaacaaat gcttcgatga ctgcatgtgt gtggaagggc tgcgctgcta tgccaaattc 960
caccggaacc gcagggttac acggaggaaa gggcgctgtg tggagcccga gacggccaac 1020
ggcgaccagg gatccttcat caacgtc 1047

<210> SEQ ID NO 19
<211> LENGTH: 1080
<212> TYPE: DNA
<213> ORGANISM: Danio rerio

<400> SEQUENCE: 19
atggtggctc ctggcttgtg tcaactcttc attctacttc ttataacact gtctcacact 60
ttgcacagct ctgaaatctc atctgacaat ttcaaacaga gtctgacccc ctccaccact 120
acctccaagg aacaccctga aacaggactt accggtggca gacaacaaaa gagacactgg 180
tcaggcaaag aacgggatag tgctgggctg ttttctcaaa ggcatatgga cagactggag 240
gatgatggga caagtatgga gggtctgagc cccgtaaggc tagagatggg acctggggac 300
actatgaagg cagaagttca cggtgaggtc agggcttctg ctcaaatgcg tcaaggaagt 360
catccagcag aaggagagtt aaatcgtaaa ggcagacgac atagtcacag gcttctggct 420
gagcacagaa agcatggagg caaaaaagac aaaggtcgag gtaaagggga tctcagcgac 480
cctgaaccag aattagactc cttgctgaag gacttaaatg catttgagga tggtctaaac 540
acttctccac ccaattacaa cagtgtccct ctcaatgaag ttccctcccc tctctcccct 600
attttggtaa ccacggcaat caaagggcat cccccaacac ttcccccagc ctccaccaaa 660
ccccagaagt caagccaagg caggactcaa ggtgaagtga tgcccactct ggacatgacc 720
ctctttgact ggactgatta tgaggatatg aagcctgcag acagttggcc atcaaacaaa 780

-continued

```
agaaaagata aacgtcgcag caaaaacaag agcaatggaa acacaacaac tgaggctgga    840

attgttgaac catgtgacca tcatcttgac tgcctttctg gttcctgttg tgacctcaga    900

gaatttgaat gtaaacctca caaccgtggc ctaaataaca agtgttttga tgactgcatg    960

tgtgaggagg gtctccgatg ttacgccaag ttccaccgca agcggagagt gacccgaaga   1020

cgtggccgct gtgtggaccc tgaatcagtc aacagcaacc aaggagcttt tattaccgtc   1080
```

<210> SEQ ID NO 20
<211> LENGTH: 1053
<212> TYPE: DNA
<213> ORGANISM: Danio rerio

<400> SEQUENCE: 20

```
atggcagttt cctgttggta ttttgcctta tttctcatct ttgacttgat gactatgaca     60

ctgggcacca acacccacca caattcacca atggaagtct tcagcgaaaa cataataatc    120

ccgcccaagc cagaggcatc catacatcat cacactcatc aaaggacaga cagaggacgc    180

aaggagagga tgacagccag tcagctcaga gaaagacccc gcattgccat cttccacacc    240

caaaatgaag ggccagacct ggagggcctc agtcccgttc gcttagagat ggaaccggca    300

gacaaacgtc gggtaatgac tcctagaaag aagaccttca tgggctctga ttccttaatt    360

caagaaaaaa tgaatatttc tcctggtgcc gagactccag agaaggcgat gaggcgtccc    420

actgttcgaa aagtgtttgg agggcacatc actagggctc ctcatgagga agagtctttg    480

gcatcaggga agaaacggag ggtttctttt gatcaaaggc tcaataaagc ctcctttggg    540

agtcccacag agccagtgct tcctgctgcc actgttggca ccttcatatt gcccataact    600

gcagcagtcg atgggaatcc aaacccctca agtgaaccgc aggtcagacg ttatttaggt    660

ggggatgtgg cgcccacttt taacatggcc ttatttgact ggacggatta tgaagatatg    720

aggcctggag ataaaaagca atattcgaaa aagcaaggtt ctgaaaaaca ggctacacaa    780

agcccaagca ctggacttgt gagacttaca tcagaaaaca atgtctgtaa acatcatctg    840

gattgtctgc caggttcctg ctgcaatctc agaaagcatg tgtgtgagct tcataaccgt    900

ggcttcaata acaagtgcta tgacagctgc atgtgtgagg aaggacttcg gtgctatgca    960

aaatcacaca gacattaccg catcacccgc aaaaagggac agtgtgttga tcctgaggac   1020

ctaaatcatg cagtcagcag atggatgcag atg                                1053
```

<210> SEQ ID NO 21
<211> LENGTH: 303
<212> TYPE: DNA
<213> ORGANISM: Danio rerio

<400> SEQUENCE: 21

```
atggtggctc ctggcttgtg tcaactcttc attctacttc ttataacact gtctcacact     60

ttgcacagct ctgaagggca tcccccaaca cttcccccag cctccaccaa accccagaag    120

tcaagccaag gcaggactca aggtgaagtg atgcccactc tggacatgac cctctttgac    180

tggactgatt atgaggatat gaagcctgca gacagttggc catcaaacaa aagaaaagat    240

aaacgtcgca gcaaaaacaa gagcaatgga aacacaacaa ctgaggctgg aattgttgaa    300

cca                                                                 303
```

<210> SEQ ID NO 22
<211> LENGTH: 101
<212> TYPE: PRT
<213> ORGANISM: Danio rerio

<400> SEQUENCE: 22

```
Met Val Ala Pro Gly Leu Cys Gln Leu Phe Ile Leu Leu Leu Ile Thr
1               5                   10                  15

Leu Ser His Thr Leu His Ser Ser Glu Gly His Pro Pro Thr Leu Pro
            20                  25                  30

Pro Ala Ser Thr Lys Pro Gln Lys Ser Ser Gln Gly Arg Thr Gln Gly
        35                  40                  45

Glu Val Met Pro Thr Leu Asp Met Thr Leu Phe Asp Trp Thr Asp Tyr
    50                  55                  60

Glu Asp Met Lys Pro Ala Asp Ser Trp Pro Ser Asn Lys Arg Lys Asp
65                  70                  75                  80

Lys Arg Arg Ser Lys Asn Lys Ser Asn Gly Asn Thr Thr Thr Glu Ala
                85                  90                  95

Gly Ile Val Glu Pro
            100
```

<210> SEQ ID NO 23
<211> LENGTH: 276
<212> TYPE: DNA
<213> ORGANISM: Danio rerio

<400> SEQUENCE: 23

```
atggtggctc ctggcttgtg tcaactcttc attctacttc ttataacact gtctcacact      60

ttgcacagct ctgaagggca tcccccaaca cttcccccag cctccaccaa accccagaag     120

tcaagccaag gcaggactca aggtgaagtg atgcccactc tggacatgac cctctttgac     180

tggactgatt atgaggatat gaagcctgca gacagttggc catcaaacaa aagaaaagat     240

aaacgtcgca gcaaaaacaa gagcaatgga aacaca                               276
```

<210> SEQ ID NO 24
<211> LENGTH: 92
<212> TYPE: PRT
<213> ORGANISM: Danio rerio

<400> SEQUENCE: 24

```
Met Val Ala Pro Gly Leu Cys Gln Leu Phe Ile Leu Leu Leu Ile Thr
1               5                   10                  15

Leu Ser His Thr Leu His Ser Ser Glu Gly His Pro Pro Thr Leu Pro
            20                  25                  30

Pro Ala Ser Thr Lys Pro Gln Lys Ser Ser Gln Gly Arg Thr Gln Gly
        35                  40                  45

Glu Val Met Pro Thr Leu Asp Met Thr Leu Phe Asp Trp Thr Asp Tyr
    50                  55                  60

Glu Asp Met Lys Pro Ala Asp Ser Trp Pro Ser Asn Lys Arg Lys Asp
65                  70                  75                  80

Lys Arg Arg Ser Lys Asn Lys Ser Asn Gly Asn Thr
                85                  90
```

<210> SEQ ID NO 25
<211> LENGTH: 222
<212> TYPE: DNA
<213> ORGANISM: Danio rerio

<400> SEQUENCE: 25

```
atggtggctc ctggcttgtg tcaactcttc attctacttc ttataacact gtctcacact      60

ttgcacagct ctgaagggca tcccccaaca cttcccccag cctccaccaa accccagaag     120
```

```
tcaagccaag gcaggactca aggtgaagtg atgcccactc tggacatgac cctctttgac    180

tggactgatt atgaggatat gaagcctgca gacagttggc ca                       222


<210> SEQ ID NO 26
<211> LENGTH: 74
<212> TYPE: PRT
<213> ORGANISM: Danio rerio

<400> SEQUENCE: 26

Met Val Ala Pro Gly Leu Cys Gln Leu Phe Ile Leu Leu Leu Ile Thr
1               5                   10                  15

Leu Ser His Thr Leu His Ser Ser Glu Gly His Pro Pro Thr Leu Pro
            20                  25                  30

Pro Ala Ser Thr Lys Pro Gln Lys Ser Ser Gln Gly Arg Thr Gln Gly
        35                  40                  45

Glu Val Met Pro Thr Leu Asp Met Thr Leu Phe Asp Trp Thr Asp Tyr
    50                  55                  60

Glu Asp Met Lys Pro Ala Asp Ser Trp Pro
65                  70


<210> SEQ ID NO 27
<211> LENGTH: 207
<212> TYPE: DNA
<213> ORGANISM: Danio rerio

<400> SEQUENCE: 27

atggtggctc ctggcttgtg tcaactcttc attctacttc ttataacact gtctcacact     60

ttgcacagct ctgaagggca tcccccaaca cttcccccag cctccaccaa accccagaag    120

tcaagccaag gcaggactca aggtgaagtg atgcccactc tggacatgac cctctttgac    180

tggactgatt atgaggatat gaagcct                                        207


<210> SEQ ID NO 28
<211> LENGTH: 69
<212> TYPE: PRT
<213> ORGANISM: Danio rerio

<400> SEQUENCE: 28

Met Val Ala Pro Gly Leu Cys Gln Leu Phe Ile Leu Leu Leu Ile Thr
1               5                   10                  15

Leu Ser His Thr Leu His Ser Ser Glu Gly His Pro Pro Thr Leu Pro
            20                  25                  30

Pro Ala Ser Thr Lys Pro Gln Lys Ser Ser Gln Gly Arg Thr Gln Gly
        35                  40                  45

Glu Val Met Pro Thr Leu Asp Met Thr Leu Phe Asp Trp Thr Asp Tyr
    50                  55                  60

Glu Asp Met Lys Pro
65


<210> SEQ ID NO 29
<211> LENGTH: 225
<212> TYPE: DNA
<213> ORGANISM: Danio rerio

<400> SEQUENCE: 29

atggtggctc ctggcttgtg tcaactcttc attctacttc ttataacact gtctcacact     60

ttgcacagct ctgaacaagg caggactcaa ggtgaagtga tgcccactct ggacatgacc    120
```

```
ctctttgact ggactgatta tgaggatatg aagcctgcag acagttggcc atcaaacaaa    180

agaaaagata aacgtcgcag caaaaacaag agcaatggaa acaca                    225


<210> SEQ ID NO 30
<211> LENGTH: 75
<212> TYPE: PRT
<213> ORGANISM: Danio rerio

<400> SEQUENCE: 30

Met Val Ala Pro Gly Leu Cys Gln Leu Phe Ile Leu Leu Leu Ile Thr
1               5                   10                  15

Leu Ser His Thr Leu His Ser Ser Glu Gln Gly Arg Thr Gln Gly Glu
            20                  25                  30

Val Met Pro Thr Leu Asp Met Thr Leu Phe Asp Trp Thr Asp Tyr Glu
        35                  40                  45

Asp Met Lys Pro Ala Asp Ser Trp Pro Ser Asn Lys Arg Lys Asp Lys
    50                  55                  60

Arg Arg Ser Lys Asn Lys Ser Asn Gly Asn Thr
65                  70                  75


<210> SEQ ID NO 31
<211> LENGTH: 171
<212> TYPE: DNA
<213> ORGANISM: Danio rerio

<400> SEQUENCE: 31

atggtggctc ctggcttgtg tcaactcttc attctacttc ttataacact gtctcacact     60

ttgcacagct ctgaacaagg caggactcaa ggtgaagtga tgcccactct ggacatgacc    120

ctctttgact ggactgatta tgaggatatg aagcctgcag acagttggcc a             171


<210> SEQ ID NO 32
<211> LENGTH: 57
<212> TYPE: PRT
<213> ORGANISM: Danio rerio

<400> SEQUENCE: 32

Met Val Ala Pro Gly Leu Cys Gln Leu Phe Ile Leu Leu Leu Ile Thr
1               5                   10                  15

Leu Ser His Thr Leu His Ser Ser Glu Gln Gly Arg Thr Gln Gly Glu
            20                  25                  30

Val Met Pro Thr Leu Asp Met Thr Leu Phe Asp Trp Thr Asp Tyr Glu
        35                  40                  45

Asp Met Lys Pro Ala Asp Ser Trp Pro
    50                  55


<210> SEQ ID NO 33
<211> LENGTH: 156
<212> TYPE: DNA
<213> ORGANISM: Danio rerio

<400> SEQUENCE: 33

atggtggctc ctggcttgtg tcaactcttc attctacttc ttataacact gtctcacact     60

ttgcacagct ctgaacaagg caggactcaa ggtgaagtga tgcccactct ggacatgacc    120

ctctttgact ggactgatta tgaggatatg aagcct                              156


<210> SEQ ID NO 34
<211> LENGTH: 52
<212> TYPE: PRT
```

<213> ORGANISM: Danio rerio

<400> SEQUENCE: 34

Met Val Ala Pro Gly Leu Cys Gln Leu Phe Ile Leu Leu Leu Ile Thr
1 5 10 15

Leu Ser His Thr Leu His Ser Ser Glu Gln Gly Arg Thr Gln Gly Glu
20 25 30

Val Met Pro Thr Leu Asp Met Thr Leu Phe Asp Trp Thr Asp Tyr Glu
35 40 45

Asp Met Lys Pro
50

<210> SEQ ID NO 35
<211> LENGTH: 141
<212> TYPE: DNA
<213> ORGANISM: Danio rerio

<400> SEQUENCE: 35
atggtggctc ctggcttgtg tcaactcttc attctacttc ttataacact gtctcacact 60
ttgcacagct ctgaaggtga agtgatgccc actctggaca tgaccctctt tgactggact 120
gattatgagg atatgaagcc t 141

<210> SEQ ID NO 36
<211> LENGTH: 47
<212> TYPE: PRT
<213> ORGANISM: Danio rerio

<400> SEQUENCE: 36

Met Val Ala Pro Gly Leu Cys Gln Leu Phe Ile Leu Leu Leu Ile Thr
1 5 10 15

Leu Ser His Thr Leu His Ser Ser Glu Gly Glu Val Met Pro Thr Leu
20 25 30

Asp Met Thr Leu Phe Asp Trp Thr Asp Tyr Glu Asp Met Lys Pro
35 40 45

<210> SEQ ID NO 37
<211> LENGTH: 1809
<212> TYPE: DNA
<213> ORGANISM: Danio rerio

<400> SEQUENCE: 37
atggtgagag tctctgatgc tttggtcact ttggtgactc tctgctgtgt gctcaaaggg 60
actgtcggcg gatatggaat gagcatgttc gccgctcaga cctccccgcc ggatccgtgt 120
tacgacgaga acggacaccc cagaagatgc atccccgact tcgtaaacgc ggcgttcggg 180
aaagaagtac gcgcgtccag cacctgcggc aaaacgccga gtcgttactg cgtggtgacc 240
gagaaagggg acgaaagaca cagaaactgc cacacgtgcg acgcgtcaga cccaaagaag 300
aatcacccac cagcttacct gaccgacctg aacaatcctc acaatctcac ctgctggcag 360
tcggacaatt acctccagta tcctcaaaac gtcactttaa ctttatcctt gggcaagaaa 420
tttgaggtga cctacgtgag tttgcagttc tgctcacctc gaccggagtc tatggcgatc 480
tttaaatcga tggactacgg aaagtcctgg gtgcctttcc agtactactc gacccagtgt 540
agaaagatgt acaacaagcc cagcaaagcc acgattacta agcagaacga gcaagaggcc 600
atctgcacag attctcacac cgacatgcat cctctctccg gcgggctgat cgcgttcagc 660
accctggacg ggcgaccctc cgcgcacgac tttgacaatt cacccgtact tcaggactgg 720

-continued

```
gtgaccgcca ctgacattaa ggtgactttc agccgcctgc acactttcgg agacgaaaac    780

gaggatgact cggagctggc cagagattcc tatttttacg cagtttccga cctgcaggtt    840

ggaggcagat gtaagtgtaa tggacacgca tcacggtgcg tcaaagaccg ggatggaaac    900

ctagtgtgcg agtgcaagca caacacagcc ggaccagagt gtgacagatg caaacctttt    960

cactatgacc gaccctggca gcgcgcaacc gccagagaag ccaacgaatg tgtcgcctgc   1020

aattgtaacc ttcatgcgag gcgctgtcgt ttcaacatgg agctttacaa actctctgga   1080

aggaaaagtg gaggagtctg tctgaactgc cgccacaata cagctggtcg ccactgccac   1140

tactgcaaag agggctacta tagagacatg tccaagccca tctcccacag aaaggcctgc   1200

aaagcctgtg attgccatcc tgtgggggcc gcgggcaaaa cctgtaacca aaccacaggc   1260

caatgcccct gtaaagacgg tgtgacgggt atcacatgca accgttgtgc taacggctac   1320

cagcagagcc gatcacccat tgccccctgc ataaaaattc ccatcgctcc gccaaccacc   1380

actgcaagca gcacagaaga gccatcagac tgtgaatcct actgcaaggc atccaaaggc   1440

aagctgaaga tcaatatgaa gaagtactgc aagaaagatt atgccgttca agtccacatc   1500

ctgaaagcag ataaagcagg agagtggtgg aagttcaccg tcaacatcat ctctgtttac   1560

aaacagggtg aaagccgaat tcgcagagga gaccagttcc tctgggtcag ggcaaaggat   1620

gtggcctgca agtgtccgaa gatcaagtcc ggcaagaaat accttctgct ggggaacgac   1680

gaggattcgc caggacaaag cggaatggtg gcggacaagg gcagtctggt cattcagtgg   1740

agagacactt gggctcggag actccggaag tttcagcaaa gggagaagaa aggaaaatgc   1800

aagaaagca                                                          1809
```

<210> SEQ ID NO 38
<211> LENGTH: 603
<212> TYPE: PRT
<213> ORGANISM: Danio rerio

<400> SEQUENCE: 38

```
Met Val Arg Val Ser Asp Ala Leu Val Thr Leu Val Thr Leu Cys Cys
1               5                   10                  15

Val Leu Lys Gly Thr Val Gly Gly Tyr Gly Met Ser Met Phe Ala Ala
            20                  25                  30

Gln Thr Ser Pro Pro Asp Pro Cys Tyr Asp Glu Asn Gly His Pro Arg
        35                  40                  45

Arg Cys Ile Pro Asp Phe Val Asn Ala Ala Phe Gly Lys Glu Val Arg
    50                  55                  60

Ala Ser Ser Thr Cys Gly Lys Thr Pro Ser Arg Tyr Cys Val Val Thr
65                  70                  75                  80

Glu Lys Gly Asp Glu Arg His Arg Asn Cys His Thr Cys Asp Ala Ser
                85                  90                  95

Asp Pro Lys Lys Asn His Pro Pro Ala Tyr Leu Thr Asp Leu Asn Asn
            100                 105                 110

Pro His Asn Leu Thr Cys Trp Gln Ser Asp Asn Tyr Leu Gln Tyr Pro
        115                 120                 125

Gln Asn Val Thr Leu Thr Leu Ser Leu Gly Lys Lys Phe Glu Val Thr
    130                 135                 140

Tyr Val Ser Leu Gln Phe Cys Ser Pro Arg Pro Glu Ser Met Ala Ile
145                 150                 155                 160

Phe Lys Ser Met Asp Tyr Gly Lys Ser Trp Val Pro Phe Gln Tyr Tyr
                165                 170                 175
```

-continued

```
Ser Thr Gln Cys Arg Lys Met Tyr Asn Lys Pro Ser Lys Ala Thr Ile
            180                 185                 190

Thr Lys Gln Asn Glu Gln Glu Ala Ile Cys Thr Asp Ser His Thr Asp
        195                 200                 205

Met His Pro Leu Ser Gly Gly Leu Ile Ala Phe Ser Thr Leu Asp Gly
    210                 215                 220

Arg Pro Ser Ala His Asp Phe Asp Asn Ser Pro Val Leu Gln Asp Trp
225                 230                 235                 240

Val Thr Ala Thr Asp Ile Lys Val Thr Phe Ser Arg Leu His Thr Phe
                245                 250                 255

Gly Asp Glu Asn Glu Asp Asp Ser Glu Leu Ala Arg Asp Ser Tyr Phe
            260                 265                 270

Tyr Ala Val Ser Asp Leu Gln Val Gly Gly Arg Cys Lys Cys Asn Gly
        275                 280                 285

His Ala Ser Arg Cys Val Lys Asp Arg Asp Gly Asn Leu Val Cys Glu
    290                 295                 300

Cys Lys His Asn Thr Ala Gly Pro Glu Cys Asp Arg Cys Lys Pro Phe
305                 310                 315                 320

His Tyr Asp Arg Pro Trp Gln Arg Ala Thr Ala Arg Glu Ala Asn Glu
                325                 330                 335

Cys Val Ala Cys Asn Cys Asn Leu His Ala Arg Arg Cys Arg Phe Asn
            340                 345                 350

Met Glu Leu Tyr Lys Leu Ser Gly Arg Lys Ser Gly Gly Val Cys Leu
        355                 360                 365

Asn Cys Arg His Asn Thr Ala Gly Arg His Cys His Tyr Cys Lys Glu
    370                 375                 380

Gly Tyr Tyr Arg Asp Met Ser Lys Pro Ile Ser His Arg Lys Ala Cys
385                 390                 395                 400

Lys Ala Cys Asp Cys His Pro Val Gly Ala Ala Gly Lys Thr Cys Asn
                405                 410                 415

Gln Thr Thr Gly Gln Cys Pro Cys Lys Asp Gly Val Thr Gly Ile Thr
            420                 425                 430

Cys Asn Arg Cys Ala Asn Gly Tyr Gln Gln Ser Arg Ser Pro Ile Ala
        435                 440                 445

Pro Cys Ile Lys Ile Pro Ile Ala Pro Pro Thr Thr Thr Ala Ser Ser
    450                 455                 460

Thr Glu Glu Pro Ser Asp Cys Glu Ser Tyr Cys Lys Ala Ser Lys Gly
465                 470                 475                 480

Lys Leu Lys Ile Asn Met Lys Lys Tyr Cys Lys Lys Asp Tyr Ala Val
                485                 490                 495

Gln Val His Ile Leu Lys Ala Asp Lys Ala Gly Glu Trp Trp Lys Phe
            500                 505                 510

Thr Val Asn Ile Ile Ser Val Tyr Lys Gln Gly Glu Ser Arg Ile Arg
        515                 520                 525

Arg Gly Asp Gln Phe Leu Trp Val Arg Ala Lys Asp Val Ala Cys Lys
    530                 535                 540

Cys Pro Lys Ile Lys Ser Gly Lys Lys Tyr Leu Leu Leu Gly Asn Asp
545                 550                 555                 560

Glu Asp Ser Pro Gly Gln Ser Gly Met Val Ala Asp Lys Gly Ser Leu
                565                 570                 575

Val Ile Gln Trp Arg Asp Thr Trp Ala Arg Arg Leu Arg Lys Phe Gln
            580                 585                 590

Gln Arg Glu Lys Lys Gly Lys Cys Lys Lys Ala
```

595 600

<210> SEQ ID NO 39
<211> LENGTH: 1374
<212> TYPE: DNA
<213> ORGANISM: Danio rerio

<400> SEQUENCE: 39
atggtaagga ttttggtaac gtgcgtctcc atggtgtcca tcacctcgat ggtgtccggt 60
gctcgcggtg gatacgggat gagcatgttc gcggctcagt cctctcctcc ggacccgtgc 120
tacgacgaga acgggaaccc cagacgctgc atccccgact tcgtgaactc cgctttcggg 180
aaggacgtgc gcgtgtccag cacctgcggc tctcctccgt cgcgctactg cgtggtgacc 240
gagaaaggcg aggagagatc gagggactgc aacatctgcg acgccacaga ccccaaaaag 300
acccatccgc ccgcatacct gacagacctc aacaaccctc ataacctcac ctgctggcag 360
tcggagaact acgtgcaata cccgcagaac gtgactctga ctctgtcttt ggggaagaag 420
tttgaagtga cttatgtgag cctccagttc tgctctcctc gccccgaatc catggccatc 480
ttcaaatcca tggactatgg gaaaacctgg gtgccttttc agttctactc aacccagtgc 540
aagaaaatgt acaacaagcc cagcaaagct gccatcacca agcagaacga gcaggaggcg 600
atctgcacgg actctcacac ggacatgcag ccgttaaccg gcggcctcat cgcgttcagc 660
acgctggatg gcagaccgtc cgcgcacgac ttcgacaact cgcccgtcct gcaggactgg 720
gtcacggcca ccgacatcaa agtgaccttc aaccggctgc acacgttcgg ggatgagaac 780
gaggacgatt cggagctcgc cagggactcg tatttttacg cggtgtctga cctgcaggtc 840
ggtggacggt gtaagtgtaa cggcacgcg tcgaagtgcg tgaaggaccg ggaaggaaac 900
ctagtgtgcg aatgcaagca caacactgcg ggaccagagt gtgacaggtg taaacccttc 960
cactacgacc ggccctggca gcgcgcgact gccagagagg cgaacgagtg tgtcgcttgt 1020
cactgtaacc tacatgcccg ccgctgccgc ttcaacatgg agctgtataa gttgtcaggc 1080
cgcaggagtg gaggagtctg cctgaactgc agacacaaca ccgccggacg ccactgccac 1140
tactgtaaag agggctacta cagagacatg agcaaggcta tatcacaccg acgtgcatgc 1200
aaagcctgcg attgtcatcc tgttggtgca gctggtaaga cctgtaacca gacaactgga 1260
cagtgtccat gtaaagatgg tgtgactggc atcacctgta atcgctgtgc taaaggatac 1320
cagcagagca gatcacccat cgccccctgt atcaaaattc cagttgctgc tccc 1374

<210> SEQ ID NO 40
<211> LENGTH: 458
<212> TYPE: PRT
<213> ORGANISM: Danio rerio

<400> SEQUENCE: 40

Met Val Arg Ile Leu Val Thr Cys Val Ser Met Val Ser Ile Thr Ser
1 5 10 15

Met Val Ser Gly Ala Arg Gly Gly Tyr Gly Met Ser Met Phe Ala Ala
20 25 30

Gln Ser Ser Pro Pro Asp Pro Cys Tyr Asp Glu Asn Gly Asn Pro Arg
35 40 45

Arg Cys Ile Pro Asp Phe Val Asn Ser Ala Phe Gly Lys Asp Val Arg
50 55 60

Val Ser Ser Thr Cys Gly Ser Pro Pro Ser Arg Tyr Cys Val Val Thr
65 70 75 80

-continued

```
Glu Lys Gly Glu Glu Arg Ser Arg Asp Cys Asn Ile Cys Asp Ala Thr
                85                  90                  95

Asp Pro Lys Lys Thr His Pro Pro Ala Tyr Leu Thr Asp Leu Asn Asn
                100                 105                 110

Pro His Asn Leu Thr Cys Trp Gln Ser Glu Asn Tyr Val Gln Tyr Pro
        115                 120                 125

Gln Asn Val Thr Leu Thr Leu Ser Leu Gly Lys Lys Phe Glu Val Thr
    130                 135                 140

Tyr Val Ser Leu Gln Phe Cys Ser Pro Arg Pro Glu Ser Met Ala Ile
145                 150                 155                 160

Phe Lys Ser Met Asp Tyr Gly Lys Thr Trp Val Pro Phe Gln Phe Tyr
                165                 170                 175

Ser Thr Gln Cys Lys Lys Met Tyr Asn Lys Pro Ser Lys Ala Ala Ile
                180                 185                 190

Thr Lys Gln Asn Glu Gln Glu Ala Ile Cys Thr Asp Ser His Thr Asp
        195                 200                 205

Met Gln Pro Leu Thr Gly Gly Leu Ile Ala Phe Ser Thr Leu Asp Gly
    210                 215                 220

Arg Pro Ser Ala His Asp Phe Asp Asn Ser Pro Val Leu Gln Asp Trp
225                 230                 235                 240

Val Thr Ala Thr Asp Ile Lys Val Thr Phe Asn Arg Leu His Thr Phe
                245                 250                 255

Gly Asp Glu Asn Glu Asp Asp Ser Glu Leu Ala Arg Asp Ser Tyr Phe
                260                 265                 270

Tyr Ala Val Ser Asp Leu Gln Val Gly Gly Arg Cys Lys Cys Asn Gly
        275                 280                 285

His Ala Ser Lys Cys Val Lys Asp Arg Glu Gly Asn Leu Val Cys Glu
    290                 295                 300

Cys Lys His Asn Thr Ala Gly Pro Glu Cys Asp Arg Cys Lys Pro Phe
305                 310                 315                 320

His Tyr Asp Arg Pro Trp Gln Arg Ala Thr Ala Arg Glu Ala Asn Glu
                325                 330                 335

Cys Val Ala Cys His Cys Asn Leu His Ala Arg Arg Cys Arg Phe Asn
                340                 345                 350

Met Glu Leu Tyr Lys Leu Ser Gly Arg Arg Ser Gly Gly Val Cys Leu
        355                 360                 365

Asn Cys Arg His Asn Thr Ala Gly Arg His Cys His Tyr Cys Lys Glu
    370                 375                 380

Gly Tyr Tyr Arg Asp Met Ser Lys Ala Ile Ser His Arg Arg Ala Cys
385                 390                 395                 400

Lys Ala Cys Asp Cys His Pro Val Gly Ala Ala Gly Lys Thr Cys Asn
                405                 410                 415

Gln Thr Thr Gly Gln Cys Pro Cys Lys Asp Gly Val Thr Gly Ile Thr
                420                 425                 430

Cys Asn Arg Cys Ala Lys Gly Tyr Gln Gln Ser Arg Ser Pro Ile Ala
        435                 440                 445

Pro Cys Ile Lys Ile Pro Val Ala Ala Pro
    450                 455
```

<210> SEQ ID NO 41
<211> LENGTH: 1374
<212> TYPE: DNA
<213> ORGANISM: Danio rerio

<400> SEQUENCE: 41

```
atggtgagag tctctgatgc tttggtcact ttggtgactc tctgctgtgt gctcaaaggg     60
actgtcggcg gatatggaat gagcatgttc gccgctcaga cctccccgcc ggatccgtgt    120
tacgacgaga acggacaccc cagaagatgc atccccgact tcgtaaacgc ggcgttcggg    180
aaagaagtac gcgcgtccag cacctgcggc aaaacgccga gtcgttactg cgtggtgacc    240
gagaaagggg acgaaagaca cagaaactgc cacacgtgcg acgcgtcaga cccaaagaag    300
aatcacccac cagcttacct gaccgacctg aacaatcctc acaatctcac ctgctggcag    360
tcggacaatt acctccagta tcctcaaaac gtcactttaa ctttatcctt gggcaagaaa    420
tttgaggtga cctacgtgag tttgcagttc tgctcacctc gaccggagtc tatggcgatc    480
tttaaatcga tggactacgg aaagtcctgg gtgcctttcc agtactactc gacccagtgt    540
agaaagatgt acaacaagcc cagcaaagcc acgattacta agcagaacga gcaagaggcc    600
atctgcacag attctcacac cgacatgcat cctctctccg gcgggctgat cgcgttcagc    660
accctggacg ggcgaccctc cgcgcacgac tttgacaatt cacccgtact tcaggactgg    720
gtgaccgcca ctgacattaa ggtgactttc agccgcctgc acactttcgg agacgaaaac    780
gaggatgact cggagctggc cagagattcc tatttttacg cagtttccga cctgcaggtt    840
ggaggcagat gtaagtgtaa tggacacgca tcacggtgcg tcaaagaccg ggatggaaac    900
ctagtgtgcg agtgcaagca caacacagcc ggaccagagt gtgacagatg caaacctttt    960
cactatgacc gaccctggca gcgcgcaacc gccagagaag ccaacgaatg tgtcgcctgc   1020
aattgtaacc ttcatgcgag gcgctgtcgt ttcaacatgg agctttacaa actctctgga   1080
aggaaaagtg gaggagtctg tctgaactgc cgccacaata cagctggtcg ccactgccac   1140
tactgcaaag agggctacta tagagacatg tccaagccca tctcccacag aaaggcctgc   1200
aaagcctgtg attgccatcc tgtgggggcc gcgggcaaaa cctgtaacca aaccacaggc   1260
caatgcccct gtaaagacgg tgtgacgggt atcacatgca accgttgtgc taacggctac   1320
cagcagagcc gatcacccat tgccccctgc ataaaaattc ccatcgctcc gcca         1374
```

<210> SEQ ID NO 42
<211> LENGTH: 458
<212> TYPE: PRT
<213> ORGANISM: Danio rerio

<400> SEQUENCE: 42

```
Met Val Arg Val Ser Asp Ala Leu Val Thr Leu Val Thr Leu Cys Cys
1               5                   10                  15

Val Leu Lys Gly Thr Val Gly Gly Tyr Gly Met Ser Met Phe Ala Ala
            20                  25                  30

Gln Thr Ser Pro Pro Asp Pro Cys Tyr Asp Glu Asn Gly His Pro Arg
        35                  40                  45

Arg Cys Ile Pro Asp Phe Val Asn Ala Ala Phe Gly Lys Glu Val Arg
    50                  55                  60

Ala Ser Ser Thr Cys Gly Lys Thr Pro Ser Arg Tyr Cys Val Val Thr
65                  70                  75                  80

Glu Lys Gly Asp Glu Arg His Arg Asn Cys His Thr Cys Asp Ala Ser
                85                  90                  95

Asp Pro Lys Lys Asn His Pro Pro Ala Tyr Leu Thr Asp Leu Asn Asn
            100                 105                 110

Pro His Asn Leu Thr Cys Trp Gln Ser Asp Asn Tyr Leu Gln Tyr Pro
        115                 120                 125
```

-continued

```
Gln Asn Val Thr Leu Thr Leu Ser Leu Gly Lys Lys Phe Glu Val Thr
    130                 135                 140

Tyr Val Ser Leu Gln Phe Cys Ser Pro Arg Pro Glu Ser Met Ala Ile
145                 150                 155                 160

Phe Lys Ser Met Asp Tyr Gly Lys Ser Trp Val Pro Phe Gln Tyr Tyr
                165                 170                 175

Ser Thr Gln Cys Arg Lys Met Tyr Asn Lys Pro Ser Lys Ala Thr Ile
            180                 185                 190

Thr Lys Gln Asn Glu Gln Glu Ala Ile Cys Thr Asp Ser His Thr Asp
        195                 200                 205

Met His Pro Leu Ser Gly Gly Leu Ile Ala Phe Ser Thr Leu Asp Gly
    210                 215                 220

Arg Pro Ser Ala His Asp Phe Asp Asn Ser Pro Val Leu Gln Asp Trp
225                 230                 235                 240

Val Thr Ala Thr Asp Ile Lys Val Thr Phe Ser Arg Leu His Thr Phe
                245                 250                 255

Gly Asp Glu Asn Glu Asp Asp Ser Glu Leu Ala Arg Asp Ser Tyr Phe
            260                 265                 270

Tyr Ala Val Ser Asp Leu Gln Val Gly Gly Arg Cys Lys Cys Asn Gly
        275                 280                 285

His Ala Ser Arg Cys Val Lys Asp Arg Asp Gly Asn Leu Val Cys Glu
    290                 295                 300

Cys Lys His Asn Thr Ala Gly Pro Glu Cys Asp Arg Cys Lys Pro Phe
305                 310                 315                 320

His Tyr Asp Arg Pro Trp Gln Arg Ala Thr Ala Arg Glu Ala Asn Glu
                325                 330                 335

Cys Val Ala Cys Asn Cys Asn Leu His Ala Arg Arg Cys Arg Phe Asn
            340                 345                 350

Met Glu Leu Tyr Lys Leu Ser Gly Arg Lys Ser Gly Gly Val Cys Leu
        355                 360                 365

Asn Cys Arg His Asn Thr Ala Gly Arg His Cys His Tyr Cys Lys Glu
    370                 375                 380

Gly Tyr Tyr Arg Asp Met Ser Lys Pro Ile Ser His Arg Lys Ala Cys
385                 390                 395                 400

Lys Ala Cys Asp Cys His Pro Val Gly Ala Ala Gly Lys Thr Cys Asn
                405                 410                 415

Gln Thr Thr Gly Gln Cys Pro Cys Lys Asp Gly Val Thr Gly Ile Thr
            420                 425                 430

Cys Asn Arg Cys Ala Asn Gly Tyr Gln Gln Ser Arg Ser Pro Ile Ala
        435                 440                 445

Pro Cys Ile Lys Ile Pro Ile Ala Pro Pro
    450                 455
```

<210> SEQ ID NO 43
<211> LENGTH: 684
<212> TYPE: DNA
<213> ORGANISM: Danio rerio

<400> SEQUENCE: 43

```
atggtgagag tctctgatgc tttggtcact ttggtgactc tctgctgtgt gctcaaaggg      60

actgtcggcg gatatggagg agacgaaaac gaggatgact cggagctggc cagagattcc     120

tatttttacg cagtttccga cctgcaggtt ggaggcagat gtaagtgtaa tggacacgca     180

tcacggtgcg tcaaagaccg ggatggaaac ctagtgtgcg agtgcaagca caacacagcc     240
```

```
ggaccagagt gtgacagatg caaacctttt cactatgacc gaccctggca gcgcgcaacc    300

gccagagaag ccaacgaatg tgtcgcctgc aattgtaacc ttcatgcgag gcgctgtcgt    360

ttcaacatgg agctttacaa actctctgga aggaaaagtg gaggagtctg tctgaactgc    420

cgccacaata cagctggtcg ccactgccac tactgcaaag agggctacta tagagacatg    480

tccaagccca tctcccacag aaaggcctgc aaagcctgtg attgccatcc tgtgggggcc    540

gcgggcaaaa cctgtaacca aaccacaggc caatgcccct gtaaagacgg tgtgacgggt    600

atcacatgca accgttgtgc taacggctac cagcagagcc gatcacccat tgccccctgc    660

ataaaaattc ccatcgctcc gcca                                           684


<210> SEQ ID NO 44
<211> LENGTH: 228
<212> TYPE: PRT
<213> ORGANISM: Danio rerio

<400> SEQUENCE: 44

Met Val Arg Val Ser Asp Ala Leu Val Thr Leu Val Thr Leu Cys Cys
1               5                   10                  15

Val Leu Lys Gly Thr Val Gly Gly Tyr Gly Gly Asp Glu Asn Glu Asp
            20                  25                  30

Asp Ser Glu Leu Ala Arg Asp Ser Tyr Phe Tyr Ala Val Ser Asp Leu
        35                  40                  45

Gln Val Gly Gly Arg Cys Lys Cys Asn Gly His Ala Ser Arg Cys Val
    50                  55                  60

Lys Asp Arg Asp Gly Asn Leu Val Cys Glu Cys Lys His Asn Thr Ala
65                  70                  75                  80

Gly Pro Glu Cys Asp Arg Cys Lys Pro Phe His Tyr Asp Arg Pro Trp
                85                  90                  95

Gln Arg Ala Thr Ala Arg Glu Ala Asn Glu Cys Val Ala Cys Asn Cys
            100                 105                 110

Asn Leu His Ala Arg Arg Cys Arg Phe Asn Met Glu Leu Tyr Lys Leu
        115                 120                 125

Ser Gly Arg Lys Ser Gly Gly Val Cys Leu Asn Cys Arg His Asn Thr
    130                 135                 140

Ala Gly Arg His Cys His Tyr Cys Lys Glu Gly Tyr Tyr Arg Asp Met
145                 150                 155                 160

Ser Lys Pro Ile Ser His Arg Lys Ala Cys Lys Ala Cys Asp Cys His
                165                 170                 175

Pro Val Gly Ala Ala Gly Lys Thr Cys Asn Gln Thr Thr Gly Gln Cys
            180                 185                 190

Pro Cys Lys Asp Gly Val Thr Gly Ile Thr Cys Asn Arg Cys Ala Asn
        195                 200                 205

Gly Tyr Gln Gln Ser Arg Ser Pro Ile Ala Pro Cys Ile Lys Ile Pro
    210                 215                 220

Ile Ala Pro Pro
225


<210> SEQ ID NO 45
<211> LENGTH: 202
<212> TYPE: PRT
<213> ORGANISM: Danio rerio

<400> SEQUENCE: 45

Gly Asp Glu Asn Glu Asp Asp Ser Glu Leu Ala Arg Asp Ser Tyr Phe
1               5                   10                  15
```

```
Tyr Ala Val Ser Asp Leu Gln Val Gly Gly Arg Cys Lys Cys Asn Gly
            20                  25                  30

His Ala Ser Arg Cys Val Lys Asp Arg Asp Gly Asn Leu Val Cys Glu
        35                  40                  45

Cys Lys His Asn Thr Ala Gly Pro Glu Cys Asp Arg Cys Lys Pro Phe
    50                  55                  60

His Tyr Asp Arg Pro Trp Gln Arg Ala Thr Ala Arg Glu Ala Asn Glu
65                  70                  75                  80

Cys Val Ala Cys Asn Cys Asn Leu His Ala Arg Arg Cys Arg Phe Asn
                85                  90                  95

Met Glu Leu Tyr Lys Leu Ser Gly Arg Lys Ser Gly Gly Val Cys Leu
            100                 105                 110

Asn Cys Arg His Asn Thr Ala Gly Arg His Cys His Tyr Cys Lys Glu
        115                 120                 125

Gly Tyr Tyr Arg Asp Met Ser Lys Pro Ile Ser His Arg Lys Ala Cys
    130                 135                 140

Lys Ala Cys Asp Cys His Pro Val Gly Ala Ala Gly Lys Thr Cys Asn
145                 150                 155                 160

Gln Thr Thr Gly Gln Cys Pro Cys Lys Asp Gly Val Thr Gly Ile Thr
                165                 170                 175

Cys Asn Arg Cys Ala Asn Gly Tyr Gln Gln Ser Arg Ser Pro Ile Ala
            180                 185                 190

Pro Cys Ile Lys Ile Pro Ile Ala Pro Pro
        195                 200
```

<210> SEQ ID NO 46
<211> LENGTH: 468
<212> TYPE: DNA
<213> ORGANISM: Danio rerio

<400> SEQUENCE: 46

```
atggtgagag tctctgatgc tttggtcact ttggtgactc tctgctgtgt gctcaaaggg     60

actgtcggcg gatatggacc tgcatcgcct gcctcacccg cttctgtcgc ctgcaattgt    120

aaccttcatg cgaggcgctg tcgtttcaac atggagcttt acaaactctc tggaaggaaa    180

agtggaggag tctgtctgaa ctgccgccac aatacagctg gtcgccactg ccactactgc    240

aaagagggct actatagaga catgtccaag cccatctccc acagaaaggc ctgcaaagcc    300

tgtgattgcc atcctgtggg ggccgcgggc aaaacctgta accaaaccac aggccaatgc    360

ccctgtaaag acggtgtgac gggtatcaca tgcaaccgtt gtgctaacgg ctaccagcag    420

agccgatcac ccattgcccc ctgcataaaa attcccatcg ctccgcca                 468
```

<210> SEQ ID NO 47
<211> LENGTH: 156
<212> TYPE: PRT
<213> ORGANISM: Danio rerio

<400> SEQUENCE: 47

```
Met Val Arg Val Ser Asp Ala Leu Val Thr Leu Val Thr Leu Cys Cys
1               5                   10                  15

Val Leu Lys Gly Thr Val Gly Gly Tyr Gly Pro Ala Ser Pro Ala Ser
            20                  25                  30

Pro Ala Ser Val Ala Cys Asn Cys Asn Leu His Ala Arg Arg Cys Arg
        35                  40                  45

Phe Asn Met Glu Leu Tyr Lys Leu Ser Gly Arg Lys Ser Gly Gly Val
```

```
    50                  55                  60

Cys Leu Asn Cys Arg His Asn Thr Ala Gly Arg His Cys His Tyr Cys
65                  70                  75                  80

Lys Glu Gly Tyr Tyr Arg Asp Met Ser Lys Pro Ile Ser His Arg Lys
                85                  90                  95

Ala Cys Lys Ala Cys Asp Cys His Pro Val Gly Ala Ala Gly Lys Thr
            100                 105                 110

Cys Asn Gln Thr Thr Gly Gln Cys Pro Cys Lys Asp Gly Val Thr Gly
        115                 120                 125

Ile Thr Cys Asn Arg Cys Ala Asn Gly Tyr Gln Gln Ser Arg Ser Pro
    130                 135                 140

Ile Ala Pro Cys Ile Lys Ile Pro Ile Ala Pro Pro
145                 150                 155


<210> SEQ ID NO 48
<211> LENGTH: 121
<212> TYPE: PRT
<213> ORGANISM: Danio rerio

<400> SEQUENCE: 48

Val Ala Cys Asn Cys Asn Leu His Ala Arg Arg Cys Arg Phe Asn Met
1               5                   10                  15

Glu Leu Tyr Lys Leu Ser Gly Arg Lys Ser Gly Gly Val Cys Leu Asn
            20                  25                  30

Cys Arg His Asn Thr Ala Gly Arg His Cys His Tyr Cys Lys Glu Gly
        35                  40                  45

Tyr Tyr Arg Asp Met Ser Lys Pro Ile Ser His Arg Lys Ala Cys Lys
    50                  55                  60

Ala Cys Asp Cys His Pro Val Gly Ala Ala Gly Lys Thr Cys Asn Gln
65                  70                  75                  80

Thr Thr Gly Gln Cys Pro Cys Lys Asp Gly Val Thr Gly Ile Thr Cys
                85                  90                  95

Asn Arg Cys Ala Asn Gly Tyr Gln Gln Ser Arg Ser Pro Ile Ala Pro
            100                 105                 110

Cys Ile Lys Ile Pro Ile Ala Pro Pro
        115                 120


<210> SEQ ID NO 49
<211> LENGTH: 279
<212> TYPE: DNA
<213> ORGANISM: Danio rerio

<400> SEQUENCE: 49

atggtgagag tctctgatgc tttggtcact ttggtgactc tctgctgtgt gctcaaaggg      60

actgtcggcg gatatggacc tgcatcgcct gcctcacccg cttctaaagc ctgtgattgc     120

catcctgtgg gggccgcggg caaaacctgt aaccaaacca caggccaatg cccctgtaaa     180

gacggtgtga cgggtatcac atgcaaccgt tgtgctaacg gctaccagca gagccgatca     240

cccattgccc cctgcataaa aattcccatc gctccgcca                           279


<210> SEQ ID NO 50
<211> LENGTH: 93
<212> TYPE: PRT
<213> ORGANISM: Danio rerio

<400> SEQUENCE: 50

Met Val Arg Val Ser Asp Ala Leu Val Thr Leu Val Thr Leu Cys Cys
```

```
1               5                   10                  15

Val Leu Lys Gly Thr Val Gly Gly Tyr Gly Pro Ala Ser Pro Ala Ser
            20                  25                  30

Pro Ala Ser Lys Ala Cys Asp Cys His Pro Val Gly Ala Ala Gly Lys
        35                  40                  45

Thr Cys Asn Gln Thr Thr Gly Gln Cys Pro Cys Lys Asp Gly Val Thr
    50                  55                  60

Gly Ile Thr Cys Asn Arg Cys Ala Asn Gly Tyr Gln Gln Ser Arg Ser
65                  70                  75                  80

Pro Ile Ala Pro Cys Ile Lys Ile Pro Ile Ala Pro Pro
                85                  90


<210> SEQ ID NO 51
<211> LENGTH: 58
<212> TYPE: PRT
<213> ORGANISM: Danio rerio

<400> SEQUENCE: 51

Lys Ala Cys Asp Cys His Pro Val Gly Ala Ala Gly Lys Thr Cys Asn
1               5                   10                  15

Gln Thr Thr Gly Gln Cys Pro Cys Lys Asp Gly Val Thr Gly Ile Thr
            20                  25                  30

Cys Asn Arg Cys Ala Asn Gly Tyr Gln Gln Ser Arg Ser Pro Ile Ala
        35                  40                  45

Pro Cys Ile Lys Ile Pro Ile Ala Pro Pro
    50                  55


<210> SEQ ID NO 52
<211> LENGTH: 343
<212> TYPE: PRT
<213> ORGANISM: Mus musculus

<400> SEQUENCE: 52

Met Ala Gly Cys Pro Val Leu Arg Val Pro Thr Leu Phe Leu Ile Leu
1               5                   10                  15

Leu Leu Phe Pro Glu Leu His Thr Ala Gly Thr Leu Ala Ser Gly Ser
            20                  25                  30

Ser Ala Arg Asn Leu Pro Glu Thr His Ser His Leu Pro Ser Ser Ala
        35                  40                  45

Leu Trp Val Ser Gln Ala Ser His His Gly Arg Arg Gly Leu Gly Lys
    50                  55                  60

Lys Asp Arg Gly Pro Gly Arg Pro Ser Arg Ala Gln Glu Gly Ala Val
65                  70                  75                  80

Val Thr Ala Thr Lys Gln Ala Ser Gln Met Thr Leu Gly Gln Pro Pro
                85                  90                  95

Ala Gly Leu Leu Gln Asn Lys Glu Leu Leu Leu Gly Leu Thr Leu Pro
            100                 105                 110

Tyr Pro Glu Lys Glu Ala Arg Ser Pro Ala Trp Glu Arg Val Lys Lys
        115                 120                 125

Arg Gly Arg Glu His Lys Arg Arg Arg Asp Arg Leu Arg Leu His Arg
    130                 135                 140

Gly Arg Ala Ala Ile Arg Gly Pro Ser Ser Leu Met Lys Lys Val Glu
145                 150                 155                 160

Pro Ser Glu Asp Arg Met Leu Glu Gly Thr Met Glu Glu Ser Ser Thr
                165                 170                 175

Ser Leu Ala Pro Thr Met Phe Phe Leu Thr Met Thr Asp Gly Ala Thr
```

```
            180                 185                 190

Pro Thr Thr Glu Glu Ser Arg Ile Leu Pro Val Thr Ser Leu Arg Pro
        195                 200                 205

Gln Thr Gln Pro Arg Ser Asp Gly Glu Val Met Pro Thr Leu Asp Met
    210                 215                 220

Ala Leu Phe Asp Trp Thr Asp Tyr Glu Asp Leu Lys Pro Glu Val Trp
225                 230                 235                 240

Pro Ser Ala Lys Lys Lys Glu Lys His Trp Ser His Phe Thr Ser Asp
                245                 250                 255

Gly Asn Glu Thr Ser Pro Ala Glu Gly Asp Pro Cys Asp His His Gln
            260                 265                 270

Asp Cys Leu Pro Gly Thr Cys Cys Asp Leu Arg Glu His Leu Cys Thr
        275                 280                 285

Pro His Asn Arg Gly Leu Asn Asn Lys Cys Phe Asp Asp Cys Met Cys
    290                 295                 300

Met Glu Gly Leu Arg Cys Tyr Ala Lys Phe His Arg Asn Arg Arg Val
305                 310                 315                 320

Thr Arg Arg Lys Gly Arg Cys Val Glu Pro Glu Thr Ala Asn Gly Asp
                325                 330                 335

Gln Gly Ser Phe Ile Asn Ile
            340


<210> SEQ ID NO 53
<211> LENGTH: 349
<212> TYPE: PRT
<213> ORGANISM: Gallus gallus

<400> SEQUENCE: 53

Met Ala Ala Ser Ser Thr Phe Phe Ser Pro Ser Leu Phe Leu Cys Val
1               5                   10                  15

Leu Val Leu Ile Asp Ile Thr Leu Ala Val Ser Leu Asp Thr Asp Met
            20                  25                  30

Lys Leu Lys Ser Glu Asn Asn Asn His Leu Gln Asn Gln Glu Thr Trp
        35                  40                  45

Pro Gln Gln Pro Arg Ser Gly His His His Lys His Gly Leu Ala Lys
    50                  55                  60

Lys Gly Arg Val Leu Ala Leu Pro Val Arg Gly Gln Pro Ala Gly Glu
65                  70                  75                  80

Glu Ala Leu Arg Val Gly Ser Gly Ala Pro Ala Met Glu Glu Leu Val
                85                  90                  95

Pro Leu Gly Gln Pro Ala Ala Leu Lys Gln Asp Lys Asp Lys Asp Val
            100                 105                 110

Phe Leu Gly Phe Glu Leu Pro His Ala Glu Arg Glu Asn Gln Ser Pro
        115                 120                 125

Gly Ser Glu Arg Gly Lys Lys Gln Asn Arg Glu Gln Arg Arg His Ser
    130                 135                 140

Arg Arg Asp Arg Leu Lys His His Arg Gly Lys Thr Ala Val Gly Pro
145                 150                 155                 160

Ser Ser Leu Tyr Lys Lys Pro Glu Ser Phe Glu Gln Gln Phe Gln Asn
                165                 170                 175

Leu Gln Ala Glu Glu Ala Thr Ser Pro Thr Pro Thr Val Leu Pro Phe
            180                 185                 190

Thr Ala Leu Asp Leu Val Val Ser Thr Glu Glu Pro Pro Val Leu Pro
        195                 200                 205
```

-continued

```
Ala Thr Ser Pro Arg Ser Gln Ala Arg Leu Arg Gln Asp Gly Asp Val
    210                 215                 220

Met Pro Thr Leu Asp Met Ala Leu Phe Asp Trp Thr Asp Tyr Glu Asp
225                 230                 235                 240

Leu Lys Pro Glu Met Trp Pro Ser Ala Lys Lys Lys Glu Lys Arg Arg
                245                 250                 255

Ser Lys Ser Ser Asn Gly Gly Asn Glu Thr Ser Ser Ala Glu Gly Glu
            260                 265                 270

Pro Cys Asp His His Leu Asp Cys Leu Pro Gly Ser Cys Cys Asp Leu
        275                 280                 285

Arg Glu His Leu Cys Lys Pro His Asn Arg Gly Leu Asn Asn Lys Cys
    290                 295                 300

Tyr Asp Asp Cys Met Cys Thr Glu Gly Leu Arg Cys Tyr Ala Lys Phe
305                 310                 315                 320

His Arg Asn Arg Arg Val Thr Arg Arg Lys Gly Arg Cys Val Glu Pro
                325                 330                 335

Glu Ser Ala Asn Gly Glu Gln Gly Ser Phe Ile Asn Val
            340                 345


<210> SEQ ID NO 54
<211> LENGTH: 21
<212> TYPE: PRT
<213> ORGANISM: Felis catus

<400> SEQUENCE: 54

Glu Val Met Pro Thr Leu Asp Met Ala Leu Phe Asp Trp Thr Asp Tyr
1               5                   10                  15

Glu Asp Leu Lys Pro
            20


<210> SEQ ID NO 55
<211> LENGTH: 21
<212> TYPE: PRT
<213> ORGANISM: Rattus norvegicus

<400> SEQUENCE: 55

Glu Val Met Pro Thr Leu Asp Met Ala Leu Phe Asp Trp Thr Asp Tyr
1               5                   10                  15

Glu Asp Leu Lys Pro
            20


<210> SEQ ID NO 56
<211> LENGTH: 21
<212> TYPE: PRT
<213> ORGANISM: Mus musculus

<400> SEQUENCE: 56

Glu Val Met Pro Thr Leu Asp Met Ala Leu Phe Asp Trp Thr Asp Tyr
1               5                   10                  15

Glu Asp Leu Lys Pro
            20


<210> SEQ ID NO 57
<211> LENGTH: 21
<212> TYPE: PRT
<213> ORGANISM: Equus caballus

<400> SEQUENCE: 57

Glu Val Met Pro Thr Leu Asp Met Ala Leu Phe Asp Trp Thr Asp Tyr
1               5                   10                  15
```

Glu Asp Leu Lys Pro
20

<210> SEQ ID NO 58
<211> LENGTH: 21
<212> TYPE: PRT
<213> ORGANISM: Bos taurus

<400> SEQUENCE: 58

Glu Val Met Pro Thr Leu Asp Met Ala Leu Phe Asp Trp Thr Asp Tyr
1 5 10 15

Glu Asp Leu Lys Pro
20

<210> SEQ ID NO 59
<211> LENGTH: 21
<212> TYPE: PRT
<213> ORGANISM: Sus scrofa

<400> SEQUENCE: 59

Glu Val Met Pro Thr Leu Asp Met Ala Leu Phe Asp Trp Thr Asp Tyr
1 5 10 15

Glu Asp Leu Lys Pro
20

<210> SEQ ID NO 60
<211> LENGTH: 21
<212> TYPE: PRT
<213> ORGANISM: Canis lupus

<400> SEQUENCE: 60

Glu Val Met Pro Thr Leu Asp Met Ala Leu Phe Asp Trp Thr Asp Tyr
1 5 10 15

Glu Asp Leu Arg Pro
20

<210> SEQ ID NO 61
<211> LENGTH: 21
<212> TYPE: PRT
<213> ORGANISM: Gallus gallus

<400> SEQUENCE: 61

Asp Val Met Pro Thr Leu Asp Met Ala Leu Phe Asp Trp Thr Asp Tyr
1 5 10 15

Glu Asp Leu Lys Pro
20

<210> SEQ ID NO 62
<211> LENGTH: 21
<212> TYPE: PRT
<213> ORGANISM: Takifugu rubripes

<400> SEQUENCE: 62

Glu Val Met Pro Thr Leu Asp Met Thr Leu Phe Asp Trp Thr Asp Tyr
1 5 10 15

Glu Asp Met Lys Pro
20

<210> SEQ ID NO 63
<211> LENGTH: 21
<212> TYPE: PRT
<213> ORGANISM: Xenopus tropicalis

<400> SEQUENCE: 63

Asp Val Met Pro Thr Leu Asp Met Thr Leu Phe Asp Trp Thr Asp Tyr
1 5 10 15

Glu Asp Met Lys Pro
20

<210> SEQ ID NO 64
<211> LENGTH: 48
<212> TYPE: PRT
<213> ORGANISM: Danio rerio

<400> SEQUENCE: 64

Cys Asp Cys His Pro Val Gly Ala Ala Gly Lys Thr Cys Asn Gln Thr
1 5 10 15

Thr Gly Gln Cys Pro Cys Lys Asp Gly Val Thr Gly Ile Thr Cys Asn
20 25 30

Arg Cys Ala Asn Gly Tyr Gln Gln Ser Arg Ser Pro Ile Ala Pro Cys
35 40 45

<210> SEQ ID NO 65
<211> LENGTH: 48
<212> TYPE: PRT
<213> ORGANISM: Homo sapiens

<400> SEQUENCE: 65

Cys Asp Cys His Pro Val Gly Ala Ala Gly Lys Thr Cys Asn Gln Thr
1 5 10 15

Thr Gly Gln Cys Pro Cys Lys Asp Gly Val Thr Gly Ile Thr Cys Asn
20 25 30

Arg Cys Ala Lys Gly Tyr Gln Gln Ser Arg Ser Pro Ile Ala Pro Cys
35 40 45

<210> SEQ ID NO 66
<211> LENGTH: 1029
<212> TYPE: DNA
<213> ORGANISM: Mus musculus

<400> SEQUENCE: 66
atggcagggt gccccgtcct cagggtcccc acgctgttcc tgatcctcct gctgtttcca 60
gagctccaca cggcaggcac ccttgcatct ggatcctctg cccggaacct gccggagacc 120
cactcccacc tccccagctc tgcactgtgg gtgtcccagg caagccatca tggccgtcgg 180
ggcctgggga agaaagacag gggcccagga aggcctagcc gggcccagga gggggctgtg 240
gtcactgcta ccaagcaggc ttcccagatg acactcggac agccccctgc tggccttctg 300
cagaataagg agctgcttct ggggctgact ttgccctacc ccgagaagga ggcccggtct 360
cccgcttggg agagggtgaa gaaacgtggc agagaacaca agagacgcag ggaccgtctg 420
cgactgcacc gaggccgagc tgccatccgt ggccccagct ccctcatgaa gaaggtggaa 480
ccctctgaag accggatgct ggagggtacc atggaggagt cttccactag cctggccccc 540
accatgttct tcctgaccat gacagacggt gccacgccta ctacagaaga gtcccggatc 600
ctgcctgtca cgtccttgcg gccccagaca cagcccaggt ctgacgggga ggtgatgccc 660
acactggaca tggccttatt tgactggacg gattatgaag acttaaagcc agaggtctgg 720
ccttctgcaa agaagaaaga gaaacactgg agtcatttta ccagtgatgg taacgagacc 780
tcgccagctg agggggatcc gtgtgaccat caccaggatt gcttgccagg aacttgctgt 840

-continued gacctccggg aacatctctg cacaccccac aaccgcggcc tcaacaacaa atgtttcgac 900
gactgcatgt gcatggaagg gctgcgttgc tatgccaaat tccaccggaa ccgcagggtc 960
actcggagga aggggcgctg cgtggaaccg gagacagcca acggggacca gggatctttc 1020
atcaacatc 1029

<210> SEQ ID NO 67
<211> LENGTH: 1047
<212> TYPE: DNA
<213> ORGANISM: Gallus gallus

<400> SEQUENCE: 67
atggcagctt cttccacctt cttctctccg tctcttttcc tgtgtgtgct ggttcttatt 60
gacatcaccc ttgccgtctc cctggacact gacatgaagc tcaaaagtga gaacaacaac 120
caccttcaaa accaagagac gtggcctcag cagcccagga gtgggcacca ccacaagcat 180
ggcttggcca agaaagggag ggtccttgcc ctgcctgtta gagggcagcc agctggggaa 240
gaggccctcc gagtgggcag tggagctcca gccatggaag agctggtgcc acttggccag 300
ccagcagcgc tgaaacagga taaggataag gatgtgttcc tgggctttga gctcccacac 360
gctgagcggg agaatcagtc ccctgggtct gagaggggaa agaagcagaa ccgagagcag 420
cgacggcaca gccgcaggga caggctgaaa caccacagag ggaagactgc cgttgggcca 480
agctccctgt ataagaaacc tgaaagcttc gagcaacagt ttcaaaacct ccaggcagag 540
gaagcaacca gcccgacccc caccgtgctt cccttcactg cactggatct ggtcgtttcc 600
acagaagagc ctcctgttct tccagccacg tcgccgcggt cacaggcccg cctcaggcaa 660
gatggggatg tgatgcccac cctagatatg gcactctttg actggacaga ttatgaggac 720
ctcaaaccag aaatgtggcc gtcagctaaa aagaaagaga aacgccgcag taagagctcc 780
aatggtggaa atgaaacctc atcggcagaa ggagagccgt gtgaccacca ccttgactgc 840
ctcccaggct cttgctgtga cttgcgtgag cacctctgca aaccacacaa tcgaggcctt 900
aacaacaaat gctacgatga ctgtatgtgc acagaagggc tacgctgtta tgccaaattc 960
caccggaacc gaagagtgac ccgaaggaaa gggcgctgtg tggagcctga gtcggccaat 1020
ggagagcagg gatcattcat taatgtt 1047

<210> SEQ ID NO 68
<211> LENGTH: 1338
<212> TYPE: DNA
<213> ORGANISM: Artificial Sequence
<220> FEATURE:
<223> OTHER INFORMATION: fusion protein (zebrafish signal sequence)-
(human Netrin1)

<400> SEQUENCE: 68
atggtggctc ctggcttgtg tcaactcttc attctacccg ggctcagcat gttcgcgggc 60
caggcggcgc agcccgatcc ctgctcggac gagaacggcc acccgcgccg ctgcatcccg 120
gactttgtca atgcggcctt cggcaaggac gtgcgcgtgt ccagcacctg cggccggccc 180
ccggcgcgct actgcgtggt gagcgagcgc ggcgaggagc ggctgcgctc gtgccacctc 240
tgcaacgcgt ccgaccccaa gaaggcgcac ccgcccgcct tcctcaccga cctcaacaac 300
ccgcacaacc tgacgtgctg gcagtccgag aactacctgc agttcccgca caacgtcacg 360
ctcacactgt ccctcggcaa gaagttcgaa gtgacctacg tgagcctgca gttctgctcg 420
ccgcggcccg agtccatggc catctacaag tccatggact acgggcgcac gtgggtgccc 480

-continued

```
ttccagttct actccacgca gtgccgcaag atgtacaacc ggccgcaccg cgcgcccatc    540

accaagcaga acgagcagga ggccgtgtgc accgactcgc acaccgacat gcgcccgctc    600

tcgggcggcc tcatcgcctt cagcacgctg gacgggcggc cctcggcgca cgacttcgac    660

aactcgcccg tgctgcagga ctgggtcacg gccacagaca tccgcgtggc cttcagccgc    720

ctgcacacgt tcggcgacga gaacgaggac gactcggagc tggcgcgcga ctcgtacttc    780

tacgcggtgt ccgacctgca ggtgggcggc cggtgcaagt gcaacggcca cgcggcccgc    840

tgcgtgcgcg accgcgacga cagcctggtg tgcgactgca ggcacaacac ggccggcccg    900

gagtgcgacc gctgcaagcc cttccactac gaccggccct ggcagcgcgc cacagcccgc    960

gaagccaacg agtgcgtggc ctgtaactgc aacctgcatg cccggcgctg ccgcttcaac   1020

atggagctct acaagctttc ggggcgcaag agcggaggtg tctgcctcaa ctgtcgccac   1080

aacaccgccg gccgccactg ccattactgc aaggagggct actaccgcga catgggcaag   1140

cccatcaccc accggaaggc ctgcaaagcc tgtgattgcc accctgtggg tgctgctggc   1200

aaaacctgca accaaaccac cggccagtgt ccctgcaagg acggcgtgac gggtatcacc   1260

tgcaaccgct gcgccaaagg ctaccagcag agccgctctc ccatcgcccc ctgcataaag   1320

atccctgtag cgccgccg                                                 1338


<210> SEQ ID NO 69
<211> LENGTH: 446
<212> TYPE: PRT
<213> ORGANISM: Artificial Sequence
<220> FEATURE:
<223> OTHER INFORMATION: fusion protein (zebrafish signal sequence)-
      (human Netrin1)

<400> SEQUENCE: 69

Met Val Ala Pro Gly Leu Cys Gln Leu Phe Ile Leu Pro Gly Leu Ser
1               5                   10                  15

Met Phe Ala Gly Gln Ala Ala Gln Pro Asp Pro Cys Ser Asp Glu Asn
            20                  25                  30

Gly His Pro Arg Arg Cys Ile Pro Asp Phe Val Asn Ala Ala Phe Gly
        35                  40                  45

Lys Asp Val Arg Val Ser Ser Thr Cys Gly Arg Pro Pro Ala Arg Tyr
    50                  55                  60

Cys Val Val Ser Glu Arg Gly Glu Glu Arg Leu Arg Ser Cys His Leu
65                  70                  75                  80

Cys Asn Ala Ser Asp Pro Lys Lys Ala His Pro Pro Ala Phe Leu Thr
                85                  90                  95

Asp Leu Asn Asn Pro His Asn Leu Thr Cys Trp Gln Ser Glu Asn Tyr
            100                 105                 110

Leu Gln Phe Pro His Asn Val Thr Leu Thr Leu Ser Leu Gly Lys Lys
        115                 120                 125

Phe Glu Val Thr Tyr Val Ser Leu Gln Phe Cys Ser Pro Arg Pro Glu
    130                 135                 140

Ser Met Ala Ile Tyr Lys Ser Met Asp Tyr Gly Arg Thr Trp Val Pro
145                 150                 155                 160

Phe Gln Phe Tyr Ser Thr Gln Cys Arg Lys Met Tyr Asn Arg Pro His
                165                 170                 175

Arg Ala Pro Ile Thr Lys Gln Asn Glu Gln Glu Ala Val Cys Thr Asp
            180                 185                 190

Ser His Thr Asp Met Arg Pro Leu Ser Gly Gly Leu Ile Ala Phe Ser
        195                 200                 205
```

Thr Leu Asp Gly Arg Pro Ser Ala His Asp Phe Asp Asn Ser Pro Val
    210                 215                 220

Leu Gln Asp Trp Val Thr Ala Thr Asp Ile Arg Val Ala Phe Ser Arg
225                 230                 235                 240

Leu His Thr Phe Gly Asp Glu Asn Glu Asp Asp Ser Glu Leu Ala Arg
                245                 250                 255

Asp Ser Tyr Phe Tyr Ala Val Ser Asp Leu Gln Val Gly Gly Arg Cys
            260                 265                 270

Lys Cys Asn Gly His Ala Ala Arg Cys Val Arg Asp Arg Asp Asp Ser
        275                 280                 285

Leu Val Cys Asp Cys Arg His Asn Thr Ala Gly Pro Glu Cys Asp Arg
    290                 295                 300

Cys Lys Pro Phe His Tyr Asp Arg Pro Trp Gln Arg Ala Thr Ala Arg
305                 310                 315                 320

Glu Ala Asn Glu Cys Val Ala Cys Asn Cys Asn Leu His Ala Arg Arg
                325                 330                 335

Cys Arg Phe Asn Met Glu Leu Tyr Lys Leu Ser Gly Arg Lys Ser Gly
            340                 345                 350

Gly Val Cys Leu Asn Cys Arg His Asn Thr Ala Gly Arg His Cys His
        355                 360                 365

Tyr Cys Lys Glu Gly Tyr Tyr Arg Asp Met Gly Lys Pro Ile Thr His
    370                 375                 380

Arg Lys Ala Cys Lys Ala Cys Asp Cys His Pro Val Gly Ala Ala Gly
385                 390                 395                 400

Lys Thr Cys Asn Gln Thr Thr Gly Gln Cys Pro Cys Lys Asp Gly Val
                405                 410                 415

Thr Gly Ile Thr Cys Asn Arg Cys Ala Lys Gly Tyr Gln Gln Ser Arg
            420                 425                 430

Ser Pro Ile Ala Pro Cys Ile Lys Ile Pro Val Ala Pro Pro
        435                 440                 445

<210> SEQ ID NO 70
<211> LENGTH: 26
<212> TYPE: PRT
<213> ORGANISM: Danio rerio

<400> SEQUENCE: 70

Met Val Ala Pro Gly Leu Cys Gln Leu Phe Ile Leu Leu Leu Ile Thr
1               5                   10                  15

Leu Ser His Thr Leu His Ser Ser Glu Gly
            20                  25

<210> SEQ ID NO 71
<211> LENGTH: 23
<212> TYPE: PRT
<213> ORGANISM: Danio rerio

<400> SEQUENCE: 71

Met Val Ala Pro Gly Leu Cys Gln Leu Phe Ile Leu Leu Leu Ile Thr
1               5                   10                  15

Leu Ser His Thr Leu His Ser
            20

<210> SEQ ID NO 72
<211> LENGTH: 1740
<212> TYPE: DNA
<213> ORGANISM: Homo sapiens

<400> SEQUENCE: 72
atgcctggct ggccctgggg gctgctgctg acggcaggca cgctcttcgc cgccctgagt 60
cctgggccgc cggcgcccgc cgacccctgc cacgatgagg ggggtgcgcc ccgcggctgc 120
gtgccaggac tggtgaacgc cgccctgggc cgcgaggtgc tggcttccag cacgtgcggg 180
cggccggcca ctcgggcctg cgacgcctcc gacccgcgac gggcacactc ccccgccctc 240
cttacttccc cagggggcac ggccagccct ctgtgctggc gctcggagtc cctgcctcgg 300
gcgcccctca acgtgactct cacggtgccc ctgggcaagg cttttgagct ggtcttcgtg 360
agcctgcgct tctgctcagc tcccccagcc tccgtggccc tgctcaagtc tcaggaccat 420
ggccgcagct gggccccgct gggcttcttc tcctcccact gtgacctgga ctatggccgt 480
ctgcctgccc ctgccaatgg cccagctggc ccagggcctg aggccctgtg cttccccgca 540
cccctggccc agcctgatgg cagcggcctt ctggccttca gcatgcagga cagcagcccc 600
ccaggcctgg acctggacag cagcccagtg ctccaagact gggtgaccgc caccgacgtc 660
cgtgtagtgc tcacaaggcc tagcacggca ggtgacccca gggacatgga ggccgtcgtc 720
ccttactcct acgcagccac cgacctccag gtgggcgggc gctgcaagtg caatggacat 780
gcctcacggt gcctgctgga cacacagggc cacctgatct gcgactgtcg gcatggcacc 840
gagggccctg actgcggccg ctgcaagccc ttctactgcg acaggccatg gcagcgggcc 900
actgcccggg aatcccacgc ctgcctcgct tgctcctgca acggccatgc ccgccgctgc 960
cgcttcaaca tggagctgta ccgactgtcc ggccgccgca gcgggggtgt ctgtctcaac 1020
tgccggcaca acaccgccgg ccgccactgc cactactgcc gggagggctt ctatcgagac 1080
cctggccgtg ccctgagtga ccgtcgggct tgcagggcct gcgactgtca cccggttggt 1140
gctgctggca agacctgcaa ccagaccaca ggccagtgtc cctgcaagga tggcgtcact 1200
ggcctcacct gcaaccgctg cgcgcctggc ttccagcaaa gccgctcccc agtggcgccc 1260
tgtgttaaga cccctatccc tggacccact gaggacagca gccctgtgca gccccaggac 1320
tgtgactcgc actgcaaacc tgcccgtggc agctaccgca tcagcctaaa gaagttctgc 1380
aagaaggact atgcggtgca ggtggcggtg ggtgcgcgcg gcgaggcgcg cggcgcgtgg 1440
acacgcttcc cggtggcggt gctcgccgtg ttccggagcg gagaggagcg cgcgcggcgc 1500
gggagtagcg cgctgtgggt gcccgccggg gatgcggcct gcggctgccc gcgcctgctc 1560
cccggccgcc gctacctcct gctgggggc gggcctggag ccgcggctgg gggcgcgggg 1620
ggccgggggc ccgggctcat cgccgcccgc ggaagcctcg tgctaccctg gagggacgcg 1680
tggacgcggc gcctgcggag gctgcagcga cgcgaacggc gggggcgctg cagcgccgcc 1740

<210> SEQ ID NO 73
<211> LENGTH: 577
<212> TYPE: PRT
<213> ORGANISM: Homo sapiens

<400> SEQUENCE: 73

Met Ser Met Phe Ala Ala Gln Thr Ser Pro Pro Asp Pro Cys Tyr Asp
1               5                   10                  15

Glu Asn Gly His Pro Arg Arg Cys Ile Pro Asp Phe Val Asn Ala Ala
            20                  25                  30

Phe Gly Lys Glu Val Arg Ala Ser Ser Thr Cys Gly Lys Thr Pro Ser
        35                  40                  45

Arg Tyr Cys Val Val Thr Glu Lys Gly Asp Glu Arg His Arg Asn Cys

-continued

```
    50                  55                  60

His Thr Cys Asp Ala Ser Asp Pro Lys Lys Asn His Pro Pro Ala Tyr
65                  70                  75                  80

Leu Thr Asp Leu Asn Asn Pro His Asn Leu Thr Cys Trp Gln Ser Asp
                85                  90                  95

Asn Tyr Leu Gln Tyr Pro Gln Asn Val Thr Leu Thr Leu Ser Leu Gly
            100                 105                 110

Lys Lys Phe Glu Val Thr Tyr Val Ser Leu Gln Phe Cys Ser Pro Arg
        115                 120                 125

Pro Glu Ser Met Ala Ile Phe Lys Ser Met Asp Tyr Gly Lys Ser Trp
    130                 135                 140

Val Pro Phe Gln Tyr Tyr Ser Thr Gln Cys Arg Lys Met Tyr Asn Lys
145                 150                 155                 160

Pro Ser Lys Ala Thr Ile Thr Lys Gln Asn Glu Gln Glu Ala Ile Cys
                165                 170                 175

Thr Asp Ser His Thr Asp Met His Pro Leu Ser Gly Gly Leu Ile Ala
            180                 185                 190

Phe Ser Thr Leu Asp Gly Arg Pro Ser Ala His Asp Phe Asp Asn Ser
        195                 200                 205

Pro Val Leu Gln Asp Trp Val Thr Ala Thr Asp Ile Lys Val Thr Phe
    210                 215                 220

Ser Arg Leu His Thr Phe Gly Asp Glu Asn Glu Asp Asp Ser Glu Leu
225                 230                 235                 240

Ala Arg Asp Ser Tyr Phe Tyr Ala Val Ser Asp Leu Gln Val Gly Gly
                245                 250                 255

Arg Cys Lys Cys Asn Gly His Ala Ser Arg Cys Val Lys Asp Arg Asp
            260                 265                 270

Gly Asn Leu Val Cys Glu Cys Lys His Asn Thr Ala Gly Pro Glu Cys
        275                 280                 285

Asp Arg Cys Lys Pro Phe His Tyr Asp Arg Pro Trp Gln Arg Ala Thr
    290                 295                 300

Ala Arg Glu Ala Asn Glu Cys Val Ala Cys Asn Cys Asn Leu His Ala
305                 310                 315                 320

Arg Arg Cys Arg Phe Asn Met Glu Leu Tyr Lys Leu Ser Gly Arg Lys
                325                 330                 335

Ser Gly Gly Val Cys Leu Asn Cys Arg His Asn Thr Ala Gly Arg His
            340                 345                 350

Cys His Tyr Cys Lys Glu Gly Tyr Tyr Arg Asp Met Ser Lys Pro Ile
        355                 360                 365

Ser His Arg Lys Ala Cys Lys Ala Cys Asp Cys His Pro Val Gly Ala
    370                 375                 380

Ala Gly Lys Thr Cys Asn Gln Thr Thr Gly Gln Cys Pro Cys Lys Asp
385                 390                 395                 400

Gly Val Thr Gly Ile Thr Cys Asn Arg Cys Ala Asn Gly Tyr Gln Gln
                405                 410                 415

Ser Arg Ser Pro Ile Ala Pro Cys Ile Lys Ile Pro Ile Ala Pro Pro
            420                 425                 430

Thr Thr Thr Ala Ser Ser Thr Glu Glu Pro Ser Asp Cys Glu Ser Tyr
        435                 440                 445

Cys Lys Ala Ser Lys Gly Lys Leu Lys Ile Asn Met Lys Lys Tyr Cys
    450                 455                 460

Lys Lys Asp Tyr Ala Val Gln Val His Ile Leu Lys Ala Asp Lys Ala
465                 470                 475                 480
```

```
Gly Glu Trp Trp Lys Phe Thr Val Asn Ile Ile Ser Val Tyr Lys Gln
                485                 490                 495

Gly Glu Ser Arg Ile Arg Arg Gly Asp Gln Phe Leu Trp Val Arg Ala
            500                 505                 510

Lys Asp Val Ala Cys Lys Cys Pro Lys Ile Lys Ser Gly Lys Lys Tyr
        515                 520                 525

Leu Leu Leu Gly Asn Asp Glu Asp Ser Pro Gly Gln Ser Gly Met Val
    530                 535                 540

Ala Asp Lys Gly Ser Leu Val Ile Gln Trp Arg Asp Thr Trp Ala Arg
545                 550                 555                 560

Arg Leu Arg Lys Phe Gln Gln Arg Glu Lys Lys Gly Lys Cys Lys Lys
                565                 570                 575

Ala


<210> SEQ ID NO 74
<211> LENGTH: 501
<212> TYPE: DNA
<213> ORGANISM: Homo sapiens

<400> SEQUENCE: 74

tgcaagtgca atggacatgc ctcacggtgc ctgctggaca cacagggcca cctgatctgc      60

gactgtcggc atggcaccga gggccctgac tgcggccgct gcaagccctt ctactgcgac     120

aggccatggc agcgggccac tgcccgggaa tcccacgcct gcctcgcttg ctcctgcaac     180

ggccatgccc gccgctgccg cttcaacatg gagctgtacc gactgtccgg ccgccgcagc     240

gggggtgtct gtctcaactg ccggcacaac accgccggcc gccactgcca ctactgccgg     300

gagggcttct atcgagaccc tggccgtgcc ctgagtgacc gtcgggcttg cagggcctgc     360

gactgtcacc cggttggtgc tgctggcaag acctgcaacc agaccacagg ccagtgtccc     420

tgcaaggatg gcgtcactgg cctcacctgc aaccgctgcg cgcctggctt ccagcaaagc     480

cgctccccag tggcgccctg t                                               501


<210> SEQ ID NO 75
<211> LENGTH: 167
<212> TYPE: PRT
<213> ORGANISM: Homo sapiens

<400> SEQUENCE: 75

Cys Lys Cys Asn Gly His Ala Ser Arg Cys Leu Leu Asp Thr Gln Gly
1               5                   10                  15

His Leu Ile Cys Asp Cys Arg His Gly Thr Glu Gly Pro Asp Cys Gly
            20                  25                  30

Arg Cys Lys Pro Phe Tyr Cys Asp Arg Pro Trp Gln Arg Ala Thr Ala
        35                  40                  45

Arg Glu Ser His Ala Cys Leu Ala Cys Ser Cys Asn Gly His Ala Arg
    50                  55                  60

Arg Cys Arg Phe Asn Met Glu Leu Tyr Arg Leu Ser Gly Arg Arg Ser
65                  70                  75                  80

Gly Gly Val Cys Leu Asn Cys Arg His Asn Thr Ala Gly Arg His Cys
                85                  90                  95

His Tyr Cys Arg Glu Gly Phe Tyr Arg Asp Pro Gly Arg Ala Leu Ser
            100                 105                 110

Asp Arg Arg Ala Cys Arg Ala Cys Asp Cys His Pro Val Gly Ala Ala
        115                 120                 125
```

-continued

```
Gly Lys Thr Cys Asn Gln Thr Thr Gly Gln Cys Pro Cys Lys Asp Gly
    130                 135                 140

Val Thr Gly Leu Thr Cys Asn Arg Cys Ala Pro Gly Phe Gln Gln Ser
145                 150                 155                 160

Arg Ser Pro Val Ala Pro Cys
                165


<210> SEQ ID NO 76
<211> LENGTH: 144
<212> TYPE: DNA
<213> ORGANISM: Homo sapiens

<400> SEQUENCE: 76

tgcgactgtc acccggttgg tgctgctggc aagacctgca accagaccac aggccagtgt      60

ccctgcaagg atggcgtcac tggcctcacc tgcaaccgct gcgcgcctgg cttccagcaa     120

agccgctccc cagtggcgcc ctgt                                            144


<210> SEQ ID NO 77
<211> LENGTH: 48
<212> TYPE: PRT
<213> ORGANISM: Homo sapiens

<400> SEQUENCE: 77

Cys Asp Cys His Pro Val Gly Ala Ala Gly Lys Thr Cys Asn Gln Thr
1               5                   10                  15

Thr Gly Gln Cys Pro Cys Lys Asp Gly Val Thr Gly Leu Thr Cys Asn
            20                  25                  30

Arg Cys Ala Pro Gly Phe Gln Gln Ser Arg Ser Pro Val Ala Pro Cys
        35                  40                  45


<210> SEQ ID NO 78
<211> LENGTH: 52
<212> TYPE: PRT
<213> ORGANISM: Homo sapiens

<400> SEQUENCE: 78

Cys Ser Cys His Pro Val Gly Ser Ala Val Leu Pro Ala Asn Ser Val
1               5                   10                  15

Thr Phe Cys Asp Pro Ser Asn Gly Asp Cys Pro Cys Lys Pro Gly Val
            20                  25                  30

Ala Gly Arg Arg Cys Asp Arg Cys Met Val Gly Tyr Trp Gly Phe Gly
        35                  40                  45

Asp Tyr Gly Cys
    50


<210> SEQ ID NO 79
<211> LENGTH: 48
<212> TYPE: PRT
<213> ORGANISM: Danio rerio

<400> SEQUENCE: 79

Cys Asp Cys His Pro Val Gly Ala Ala Gly Lys Thr Cys Asn Gln Thr
1               5                   10                  15

Thr Gly Gln Cys Pro Cys Lys Asp Gly Val Thr Gly Ile Thr Cys Asn
            20                  25                  30

Arg Cys Ala Lys Gly Tyr Gln Gln Ser Arg Ser Pro Ile Ala Pro Cys
        35                  40                  45


<210> SEQ ID NO 80
```

-continued

```
<211> LENGTH: 25
<212> TYPE: DNA
<213> ORGANISM: Artificial Sequence
<220> FEATURE:
<223> OTHER INFORMATION: ntn1a morpholino

<400> SEQUENCE: 80

atgatggact taccgacaca ttcgt                                   25


<210> SEQ ID NO 81
<211> LENGTH: 25
<212> TYPE: DNA
<213> ORGANISM: Artificial Sequence
<220> FEATURE:
<223> OTHER INFORMATION: ntn1b morpholino

<400> SEQUENCE: 81

cgcacgttac caaaatcctt atcat                                   25


<210> SEQ ID NO 82
<211> LENGTH: 5
<212> TYPE: PRT
<213> ORGANISM: Artificial Sequence
<220> FEATURE:
<223> OTHER INFORMATION: peptide linker

<400> SEQUENCE: 82

Ser Gly Gly Gly Gly
1               5
```